(12) United States Patent
Podobas et al.

(10) Patent No.: US 12,738,377 B2
(45) **Date of Patent: *Sep. 15, 2026**

(54) METHODS AND SYSTEMS FOR SECURELY COMMUNICATING OVER NETWORKS, IN REAL TIME, AND UTILIZING BIOMETRIC DATA

(71) Applicant: HeartCloud, Inc., Irvine, CA (US)

(72) Inventors: Alexander Michael Podobas, Los Angeles, CA (US); Ian Ainsworth Cook, Los Angeles, CA (US); Ross John Bollens, Los Angeles, CA (US); Derek Dariusz Podobas, Los Angeles, CA (US)

(73) Assignee: HeartCloud, Inc., Irvine, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 18/592,337

(22) Filed: Feb. 29, 2024

(65) Prior Publication Data

US 2024/0282445 A1 Aug. 22, 2024

Related U.S. Application Data

(63) Continuation of application No. 17/748,530, filed on May 19, 2022, now Pat. No. 11,948,682, which is a
(Continued)

(51) Int. Cl.
*G16H 40/67* (2018.01)
*G06F 3/0483* (2013.01)
(Continued)

(52) U.S. Cl.
CPC .......... *G16H 40/67* (2018.01); *G06F 3/0483* (2013.01); *G16H 10/60* (2018.01); *G16H 80/00* (2018.01)

(58) Field of Classification Search
CPC ........ G16H 40/67; G16H 10/60; G16H 80/00; G06F 3/0483
(Continued)

(56) References Cited

U.S. PATENT DOCUMENTS 11,270,795 B2 * 3/2022 Mason .................. G16H 20/30
11,342,075 B2 5/2022 Podobas et al.
(Continued)

FOREIGN PATENT DOCUMENTS

WO WO 2021/236839 11/2021

OTHER PUBLICATIONS

Search Report and Written Opinion received in International Application No. PCT/US2021/033257 dated Aug. 16, 2021, 14 pages.

*Primary Examiner* — Peter H Choi
*Assistant Examiner* — Rachael Stone
(74) *Attorney, Agent, or Firm* — Knobbe, Martens, Olson & Bear LLP

(57) ABSTRACT

Systems and methods described herein facilitate biometric, health, and activity data aggregation and visualization in order to provide improved physical performance tracking and medical monitoring. In some examples, the system can providing real time access to healthcare providers during telehealth sessions. In some examples, the system can include infectious disease monitoring, enabling a healthcare provider to monitor and provide healthcare to a group of patients outside of a clinical setting.

16 Claims, 45 Drawing Sheets

Related U.S. Application Data continuation of application No. 17/325,101, filed on May 19, 2021, now Pat. No. 11,342,075.

(60) Provisional application No. 63/029,093, filed on May 22, 2020.

(51) Int. Cl.
*G16H 10/60* (2018.01)
*G16H 80/00* (2018.01)

(58) Field of Classification Search
USPC .............................................................. 705/2
See application file for complete search history.

(56) References Cited

U.S. PATENT DOCUMENTS

| | | | |
|---|---|---|---|
| 11,490,228 B1 | 11/2022 | Baroudi et al. | |
| 11,948,682 B2 | 4/2024 | Podobas et al. | |
| 2020/0126593 A1 | 4/2020 | Rothschild et al. | |
| 2020/0152339 A1 | 5/2020 | Pulitzer et al. | |
| 2021/0169417 A1* | 6/2021 | Burton | A61B 5/4815 |
| 2021/0366608 A1 | 11/2021 | Podobas et al. | |
| 2022/0093230 A1 | 3/2022 | Gupta | |
| 2022/0310219 A1 | 9/2022 | Sanchez, Jr. et al. | |
| 2022/0341217 A1 | 10/2022 | Cristache | |
| 2023/0119461 A1 | 4/2023 | Mason | |

* cited by examiner

350

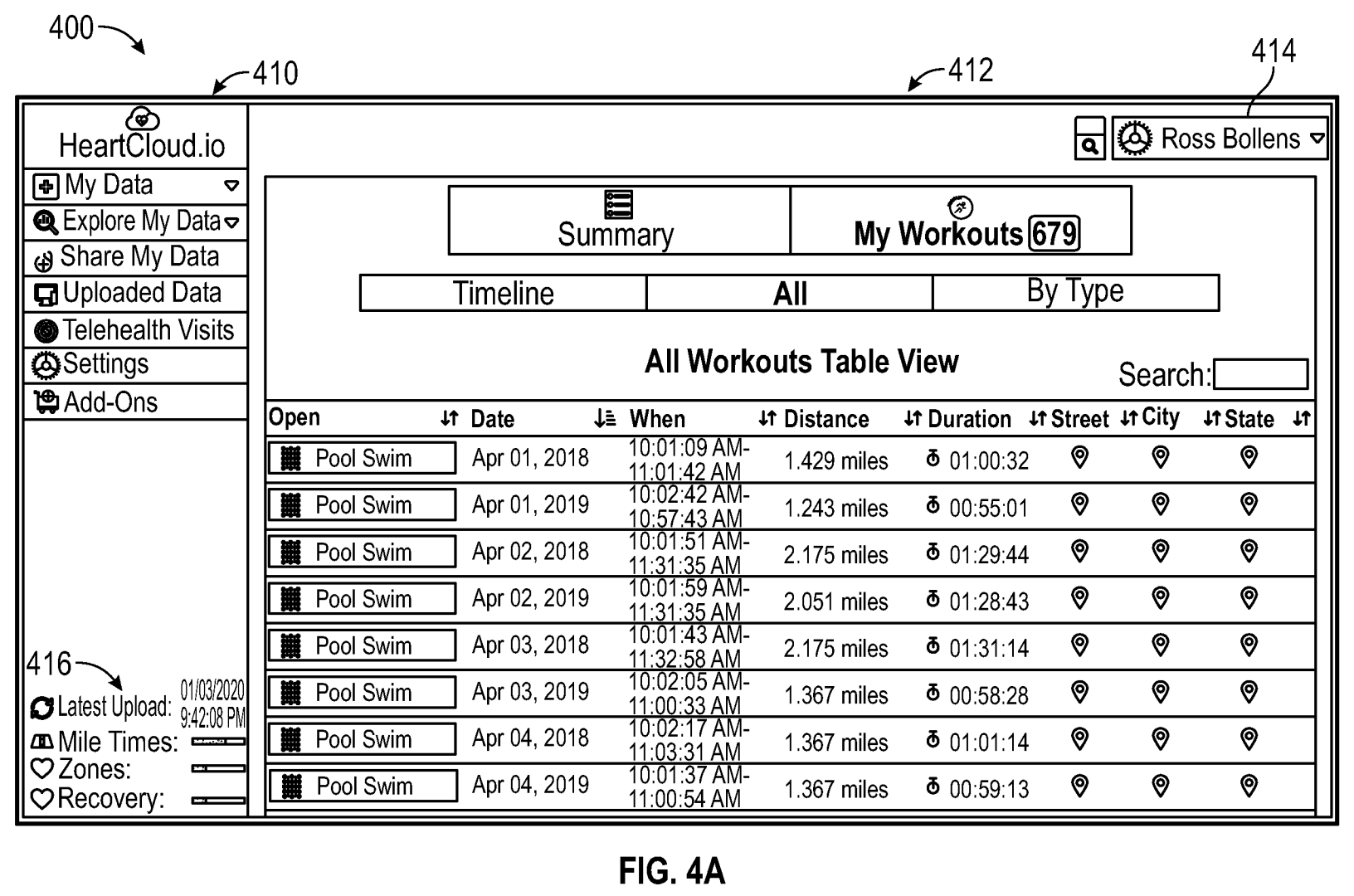

| Open | Date | When | Distance | Duration | Street | City | State |
|---|---|---|---|---|---|---|---|
| Pool Swim | Apr 01, 2018 | 10:01:09 AM-11:01:42 AM | 1.429 miles | 01:00:32 | | | |
| Pool Swim | Apr 01, 2019 | 10:02:42 AM-10:57:43 AM | 1.243 miles | 00:55:01 | | | |
| Pool Swim | Apr 02, 2018 | 10:01:51 AM-11:31:35 AM | 2.175 miles | 01:29:44 | | | |
| Pool Swim | Apr 02, 2019 | 10:01:59 AM-11:31:35 AM | 2.051 miles | 01:28:43 | | | |
| Pool Swim | Apr 03, 2018 | 10:01:43 AM-11:32:58 AM | 2.175 miles | 01:31:14 | | | |
| Pool Swim | Apr 03, 2019 | 10:02:05 AM-11:00:33 AM | 1.367 miles | 00:58:28 | | | |
| Pool Swim | Apr 04, 2018 | 10:02:17 AM-11:03:31 AM | 1.367 miles | 01:01:14 | | | |
| Pool Swim | Apr 04, 2019 | 10:01:37 AM-11:00:54 AM | 1.367 miles | 00:59:13 | | | |

FIG. 4A

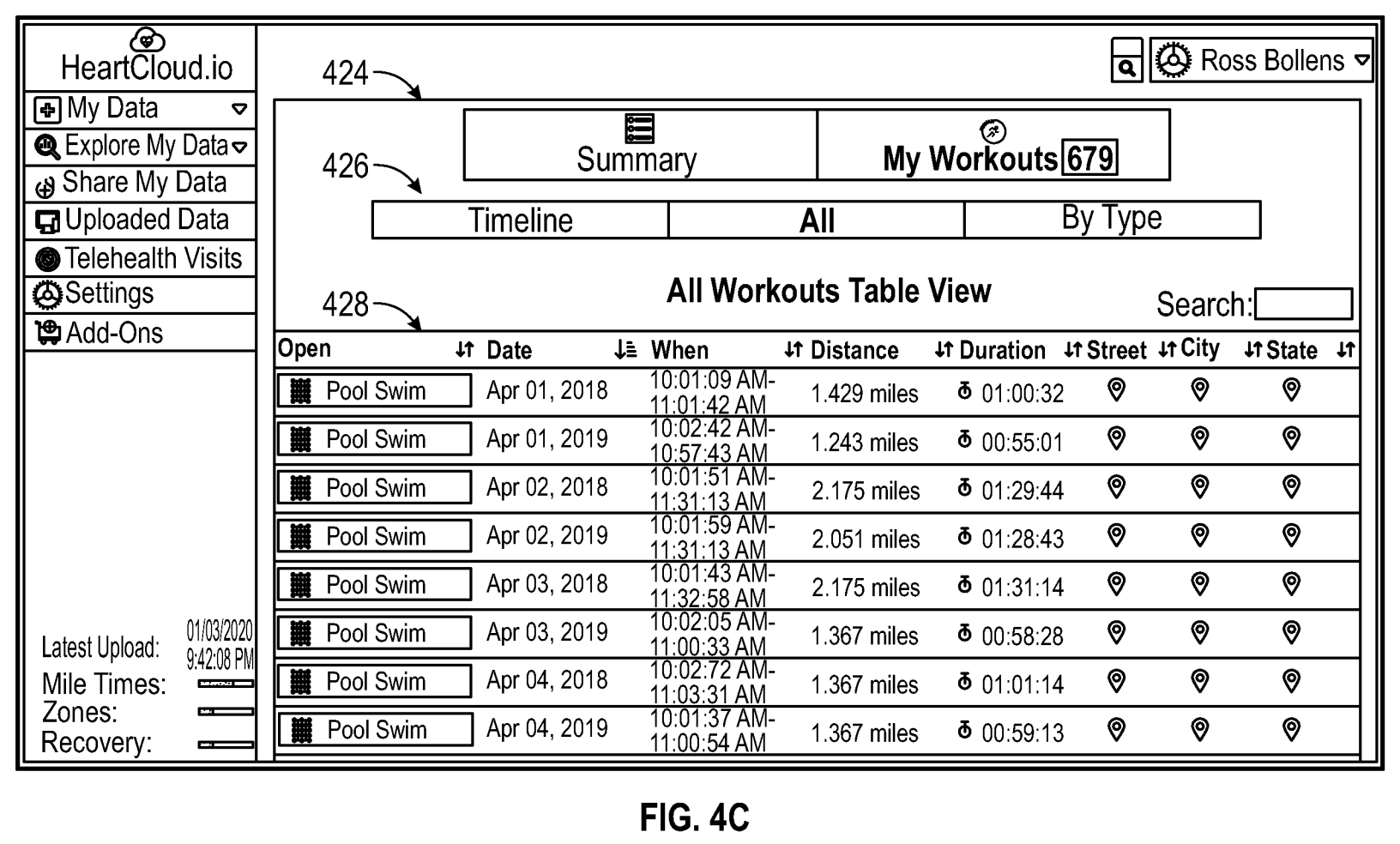

HeartCloud.io

My Data
Explore My Data
Share My Data
Uploaded Data
Telehealth Visits
Settings
Add-Ons Latest Upload: 01/03/2020 9:42:08 PM
Mile Times:
Zones:
Recovery:

Ross Bollens

424 Summary | My Workouts 679

426 Timeline | All | By Type

428 All Workouts Table View

Search:

| Open | Date | When | Distance | Duration | Street | City | State |
| --- | --- | --- | --- | --- | --- | --- | --- |
| Pool Swim | Apr 01, 2018 | 10:01:09 AM-11:01:42 AM | 1.429 miles | 01:00:32 | | | |
| Pool Swim | Apr 01, 2019 | 10:02:42 AM-10:57:43 AM | 1.243 miles | 00:55:01 | | | |
| Pool Swim | Apr 02, 2018 | 10:01:51 AM-11:31:13 AM | 2.175 miles | 01:29:44 | | | |
| Pool Swim | Apr 02, 2019 | 10:01:59 AM-11:31:13 AM | 2.051 miles | 01:28:43 | | | |
| Pool Swim | Apr 03, 2018 | 10:01:43 AM-11:32:58 AM | 2.175 miles | 01:31:14 | | | |
| Pool Swim | Apr 03, 2019 | 10:02:05 AM-11:00:33 AM | 1.367 miles | 00:58:28 | | | |
| Pool Swim | Apr 04, 2018 | 10:02:72 AM-11:03:31 AM | 1.367 miles | 01:01:14 | | | |
| Pool Swim | Apr 04, 2019 | 10:01:37 AM-11:00:54 AM | 1.367 miles | 00:59:13 | | | |

FIG. 4C

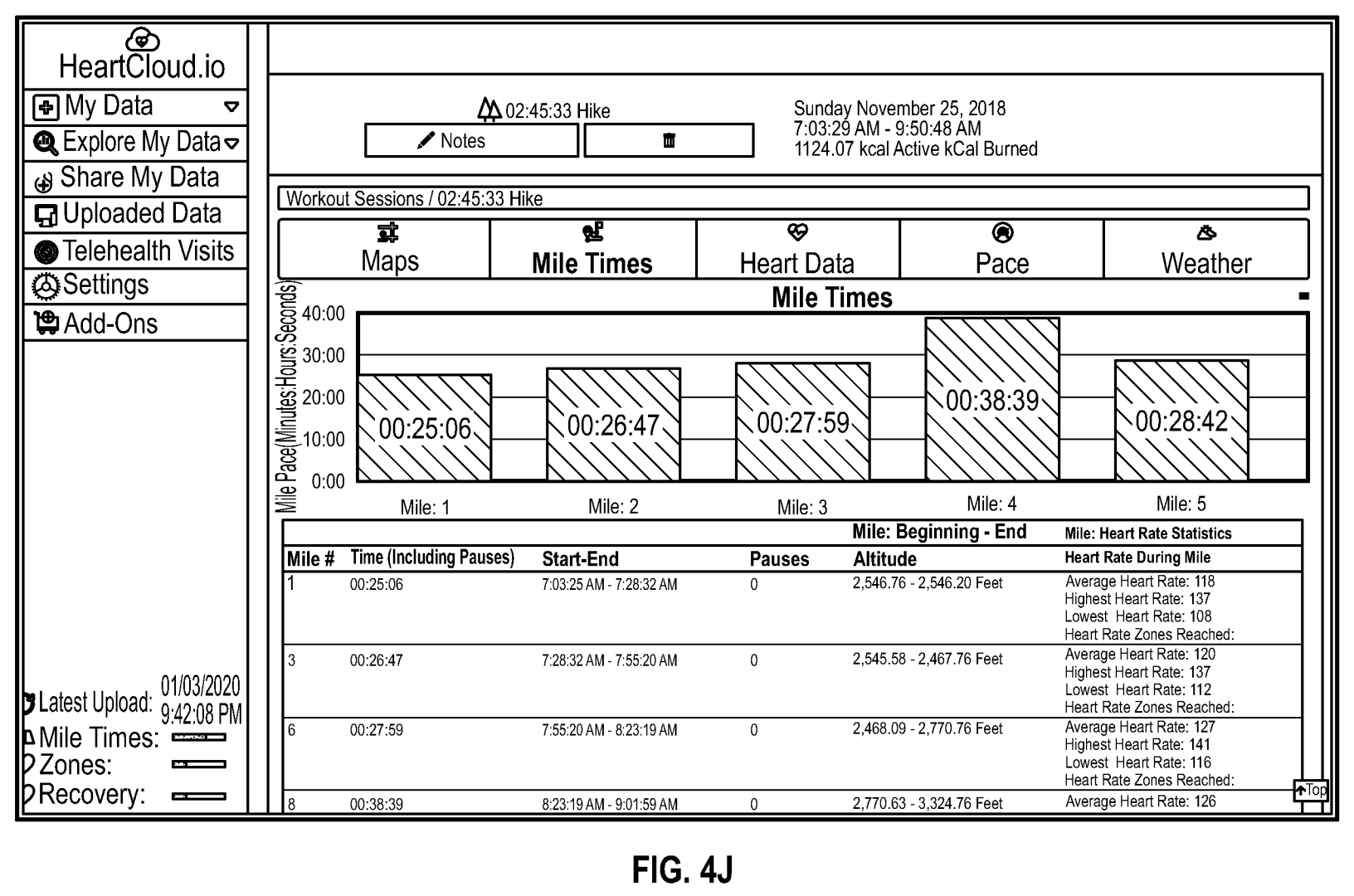

HeartCloud.io
My Data
Explore My Data
Share My Data
Uploaded Data
Telehealth Visits
Settings
Add-Ons Latest Upload: 01/03/2020 9:42:08 PM
Mile Times:
Zones:
Recovery:

02:45:33 Hike
Notes

Sunday November 25, 2018
7:03:29 AM - 9:50:48 AM
1124.07 kcal Active kCal Burned Workout Sessions / 02:45:33 Hike Maps | Mile Times | Heart Data | Pace | Weather

Mile Times

Mile Pace(Minutes:Hours:Seconds)
40:00
30:00
20:00
10:00
0:00

00:25:06 — Mile: 1
00:26:47 — Mile: 2
00:27:59 — Mile: 3
00:38:39 — Mile: 4
00:28:42 — Mile: 5

| | | | | Mile: Beginning - End | Mile: Heart Rate Statistics |
|---|---|---|---|---|---|
| **Mile #** | **Time (Including Pauses)** | **Start-End** | **Pauses** | **Altitude** | **Heart Rate During Mile** |
| 1 | 00:25:06 | 7:03:25 AM - 7:28:32 AM | 0 | 2,546.76 - 2,546.20 Feet | Average Heart Rate: 118<br>Highest Heart Rate: 137<br>Lowest Heart Rate: 108<br>Heart Rate Zones Reached: |
| 3 | 00:26:47 | 7:28:32 AM - 7:55:20 AM | 0 | 2,545.58 - 2,467.76 Feet | Average Heart Rate: 120<br>Highest Heart Rate: 137<br>Lowest Heart Rate: 112<br>Heart Rate Zones Reached: |
| 6 | 00:27:59 | 7:55:20 AM - 8:23:19 AM | 0 | 2,468.09 - 2,770.76 Feet | Average Heart Rate: 127<br>Highest Heart Rate: 141<br>Lowest Heart Rate: 116<br>Heart Rate Zones Reached: |
| 8 | 00:38:39 | 8:23:19 AM - 9:01:59 AM | 0 | 2,770.63 - 3,324.76 Feet | Average Heart Rate: 126 |

Top

FIG. 4J

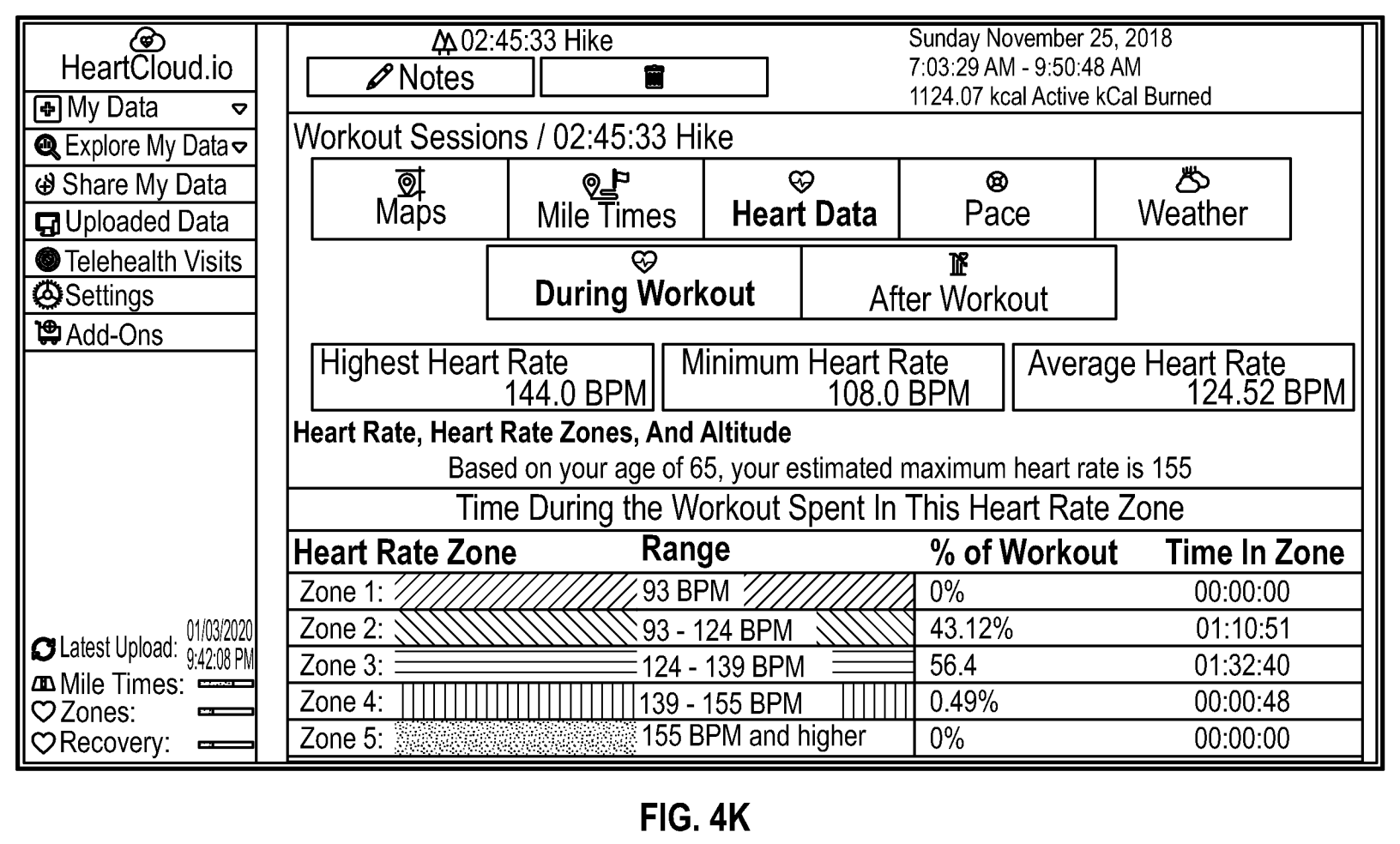

HeartCloud.io
My Data
Explore My Data
Share My Data
Uploaded Data
Telehealth Visits
Settings
Add-Ons Latest Upload: 01/03/2020 9:42:08 PM
Mile Times:
Zones:
Recovery:

02:45:33 Hike

Notes

Sunday November 25, 2018
7:03:29 AM - 9:50:48 AM
1124.07 kcal Active kCal Burned Workout Sessions / 02:45:33 Hike Maps | Mile Times | Heart Data | Pace | Weather

During Workout | After Workout

Highest Heart Rate 144.0 BPM

Minimum Heart Rate 108.0 BPM

Average Heart Rate 124.52 BPM

Heart Rate, Heart Rate Zones, And Altitude

Based on your age of 65, your estimated maximum heart rate is 155

Time During the Workout Spent In This Heart Rate Zone

| **Heart Rate Zone** | **Range** | **% of Workout** | **Time In Zone** |
|---|---|---|---|
| Zone 1: | 93 BPM | 0% | 00:00:00 |
| Zone 2: | 93 - 124 BPM | 43.12% | 01:10:51 |
| Zone 3: | 124 - 139 BPM | 56.4 | 01:32:40 |
| Zone 4: | 139 - 155 BPM | 0.49% | 00:00:48 |
| Zone 5: | 155 BPM and higher | 0% | 00:00:00 |

FIG. 4K

Advanced Clinical Care Associates | 1 | View Patient Data | $12.6 | Ian Cook, MD Patient | 00:04:43 | End Telehealth Visit | Medical Records | Health Data Showing available medical records from these patient portals: UC Irvine Health, Medications 5 | Clinical Notes | Immunizations | Diagnoses | Labs | Vital Signs SOAP Notes

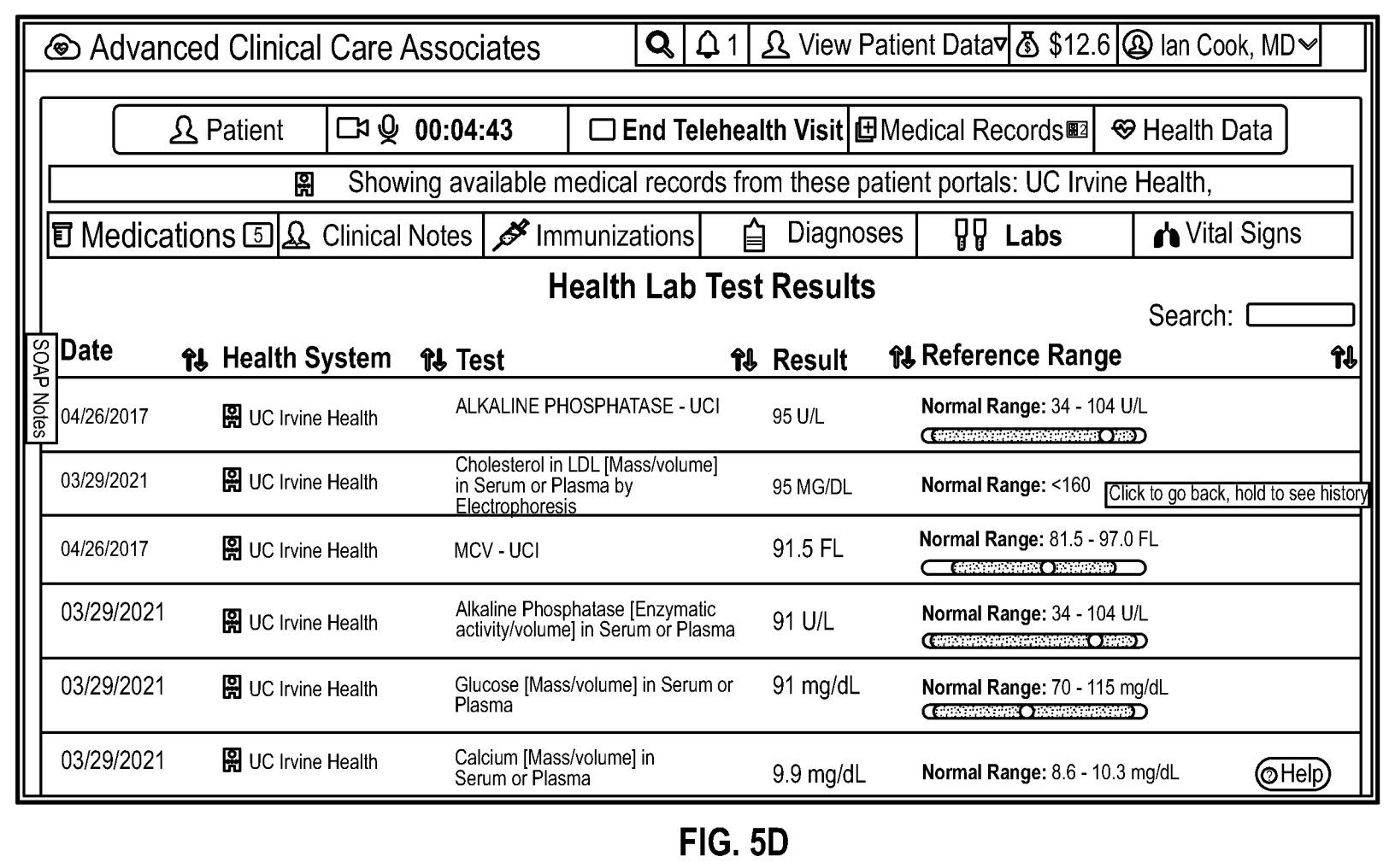

Health Lab Test Results

Search:

| Date | Health System | Test | Result | Reference Range |
|---|---|---|---|---|
| 04/26/2017 | UC Irvine Health | ALKALINE PHOSPHATASE - UCI | 95 U/L | **Normal Range:** 34 - 104 U/L |
| 03/29/2021 | UC Irvine Health | Cholesterol in LDL [Mass/volume] in Serum or Plasma by Electrophoresis | 95 MG/DL | **Normal Range:** <160 |
| 04/26/2017 | UC Irvine Health | MCV - UCI | 91.5 FL | **Normal Range:** 81.5 - 97.0 FL |
| 03/29/2021 | UC Irvine Health | Alkaline Phosphatase [Enzymatic activity/volume] in Serum or Plasma | 91 U/L | **Normal Range:** 34 - 104 U/L |
| 03/29/2021 | UC Irvine Health | Glucose [Mass/volume] in Serum or Plasma | 91 mg/dL | **Normal Range:** 70 - 115 mg/dL |
| 03/29/2021 | UC Irvine Health | Calcium [Mass/volume] in Serum or Plasma | 9.9 mg/dL | **Normal Range:** 8.6 - 10.3 mg/dL |

Click to go back, hold to see history

Help

FIG. 5D

| Medical Record # | Patient Status | Age | Sex |
|---|---|---|---|
| MRN-2114 | Established | 06/27/1956 (64) | |
| 1234567890 | New | 11/30/1982 (38) | Male |
| 987654321 | New | 12/31/1987 (33) | Other |
| 6784 | New | 12/04/1987 (33) | Male |

FIG. 5H

| View/Edit | Name | Title |
|---|---|---|
| Profile | Alex Podobas<br>alex+hchp@heartcloud.io | CTO |
| Profile | Bobby Sasson , MD<br>bsasson@hs.uci.edu | Internal Medicine Physician<br>Physician |
| Profile | Gerrit Van Hartogh<br>gerrit@heartcloud.io | Marketing & Sales |
| Profile | Ian Cook , MD<br>ian@heartcloud.io | Medical Director<br>Physician |
| Profile | Jay McNab<br>jay.hchp@jaymcnab.com | DB Administrator |

FIG. 5I

Practice-Generated Visit
Created By Jay McNab

| | | | |
|---|---|---|---|
| **Patient:** | Harry McNab | **Timed Duration:** | 00:06:46 |
| **Physician:** | Ian Cook, MD | **Session Connect:** | 02/13/2021 8:44:15 PM -08:00 |
| **Date:** | Saturday February 13, 2021<br>**Timezone**: 8:39 PM-8:59 PM (Pacific Standard Time) | **Session Disconnect:** | |
| **Scheduled Time:** | 8:39:00 PM - 8:59:00 PM | | |
| **Scheduled Duration:** | 20 Minutes | | |

| Date | Time | Who | Details | | |
|---|---|---|---|---|---|
| 02/14/2021 | 04:40:36.485000 | | Patient Requested Telehealth Visit | | |
| 02/14/2021 | 04:40:36.486000 | Ian Cook, MD | Connected | Video: On | Audio: On |
| 02/14/2021 | 04:42:19.117000 | Harry McNab, | Connected | Video: On | Audio: On |
| 02/14/2021 | 04:42:44.799000 | Ian Cook, MD | **Disconnected** | | |
| 02/14/2021 | 04:42:54.901000 | Ian Cook, MD | Connected | Video: On | Audio: On |
| 02/14/2021 | 04:42:59.285000 | Ian Cook, MD | **Disconnected** | | |
| 02/14/2021 | 04:43:14.548000 | Ian Cook, MD | Connected | Video: On | Audio: On |
| 02/14/2021 | 04:44:13.313000 | Ian Cook, MD | **Disconnected** | | |
| 02/14/2021 | 04:44:22.467000 | Ian Cook, MD | Connected | Video: On | Audio: On |
| 02/14/2021 | 04:47:14.581000 | Harry McNab, | **Disconnected** | | |
| 02/14/2021 | 04:47:22.509000 | Ian Cook, MD | **Disconnected** | **Telehealth Visit Ended** | |

FIG. 5J

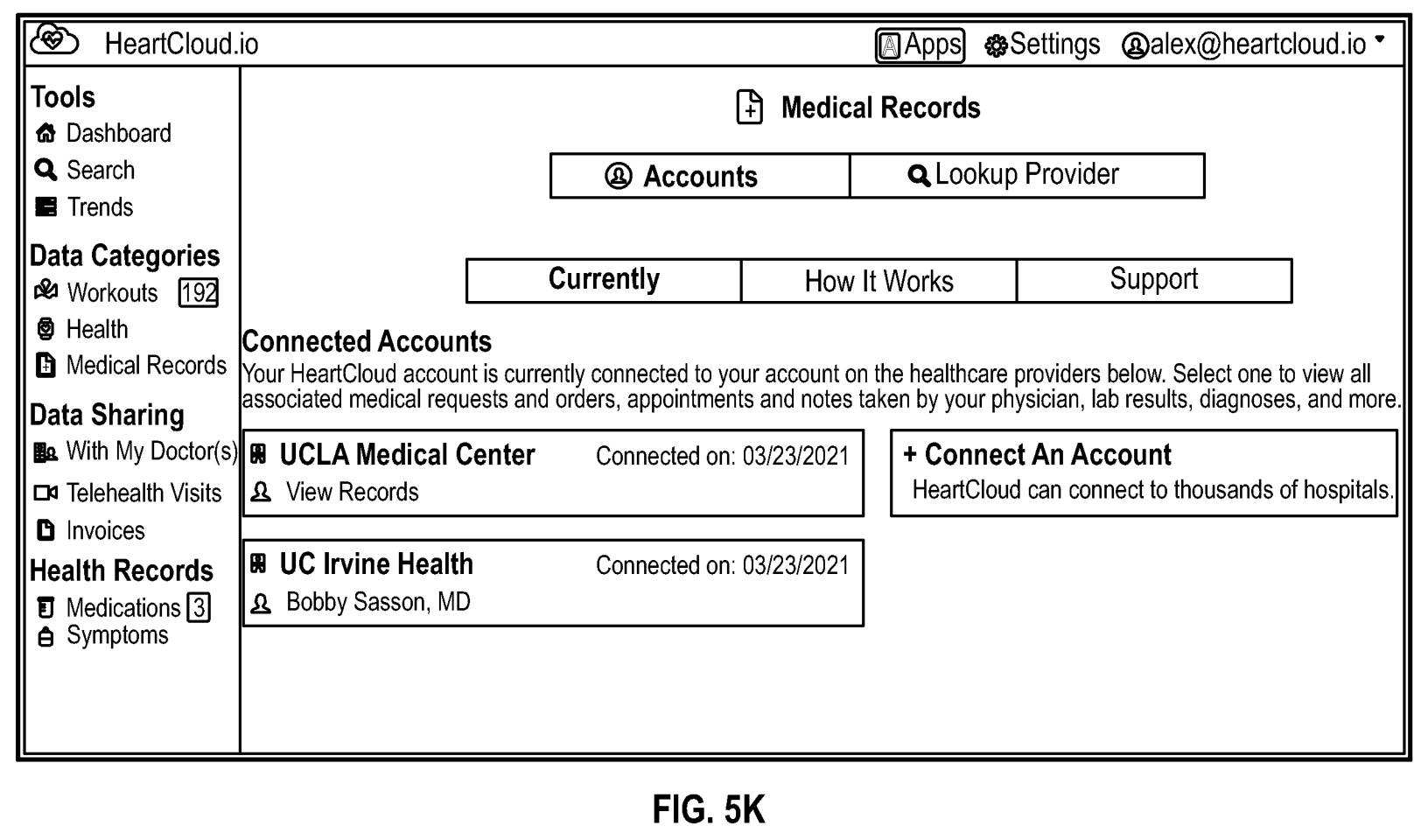

HeartCloud.io
Apps
Settings
alex@heartcloud.io

Tools
Dashboard
Search
Trends

Data Categories
Workouts 192
Health
Medical Records

Data Sharing
With My Doctor(s)
Telehealth Visits
Invoices

Health Records
Medications 3
Symptoms

Medical Records

Accounts | Lookup Provider

Currently | How It Works | Support

Connected Accounts
Your HeartCloud account is currently connected to your account on the healthcare providers below. Select one to view all associated medical requests and orders, appointments and notes taken by your physician, lab results, diagnoses, and more.

UCLA Medical Center
Connected on: 03/23/2021
View Records

+ Connect An Account
HeartCloud can connect to thousands of hospitals.

UC Irvine Health
Connected on: 03/23/2021
Bobby Sasson, MD

FIG. 5K

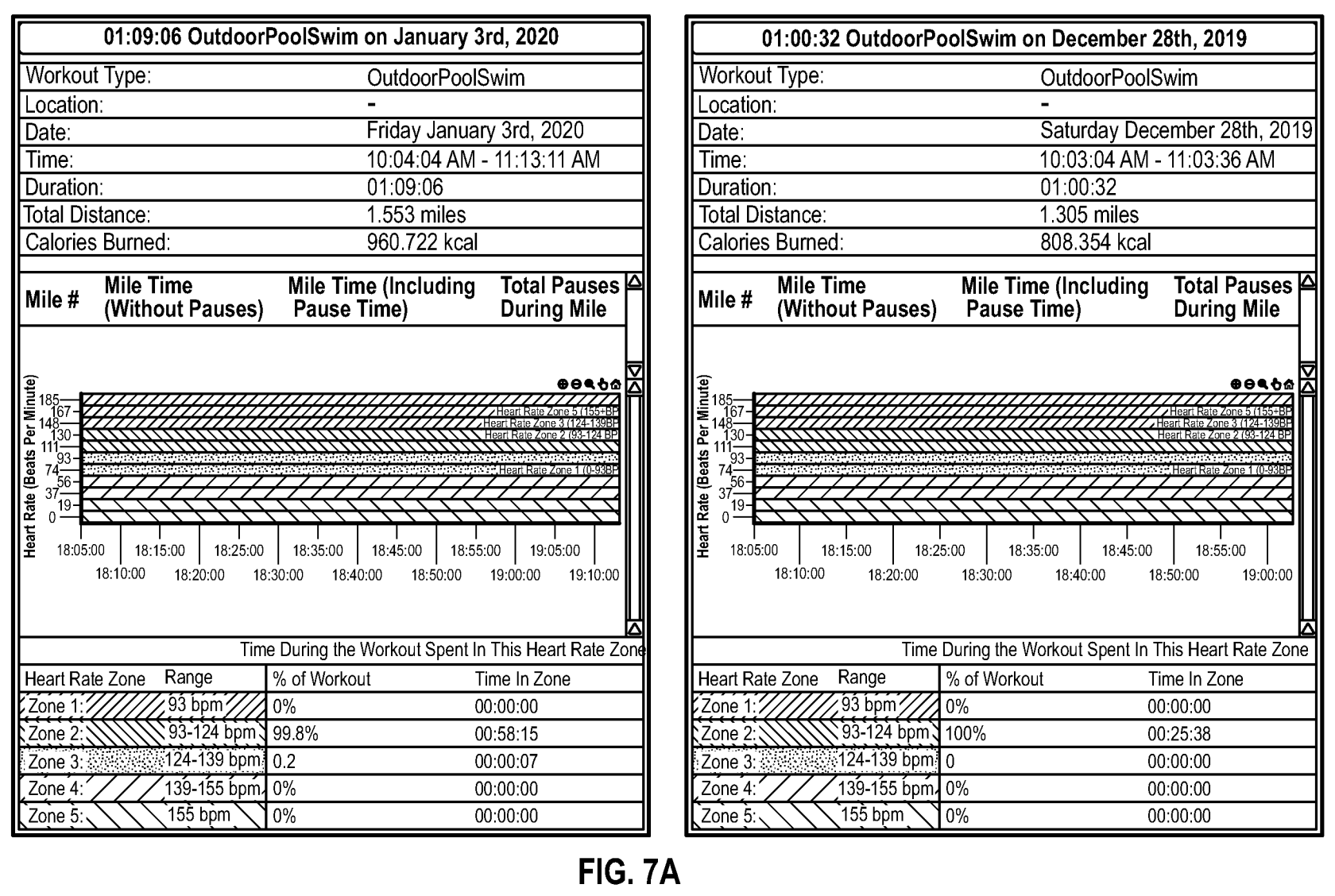

01:09:06 OutdoorPoolSwim on January 3rd, 2020

| Workout Type: | OutdoorPoolSwim |
|---|---|
| Location: | - |
| Date: | Friday January 3rd, 2020 |
| Time: | 10:04:04 AM - 11:13:11 AM |
| Duration: | 01:09:06 |
| Total Distance: | 1.553 miles |
| Calories Burned: | 960.722 kcal |

| Mile # | Mile Time (Without Pauses) | Mile Time (Including Pause Time) | Total Pauses During Mile |
|---|---|---|---|

Time During the Workout Spent In This Heart Rate Zone

| Heart Rate Zone | Range | % of Workout | Time In Zone |
|---|---|---|---|
| Zone 1: | 93 bpm | 0% | 00:00:00 |
| Zone 2: | 93-124 bpm | 99.8% | 00:58:15 |
| Zone 3: | 124-139 bpm | 0.2 | 00:00:07 |
| Zone 4: | 139-155 bpm | 0% | 00:00:00 |
| Zone 5: | 155 bpm | 0% | 00:00:00 |

01:00:32 OutdoorPoolSwim on December 28th, 2019

| Workout Type: | OutdoorPoolSwim |
|---|---|
| Location: | - |
| Date: | Saturday December 28th, 2019 |
| Time: | 10:03:04 AM - 11:03:36 AM |
| Duration: | 01:00:32 |
| Total Distance: | 1.305 miles |
| Calories Burned: | 808.354 kcal |

| Mile # | Mile Time (Without Pauses) | Mile Time (Including Pause Time) | Total Pauses During Mile |
|---|---|---|---|

Time During the Workout Spent In This Heart Rate Zone

| Heart Rate Zone | Range | % of Workout | Time In Zone |
|---|---|---|---|
| Zone 1: | 93 bpm | 0% | 00:00:00 |
| Zone 2: | 93-124 bpm | 100% | 00:25:38 |
| Zone 3: | 124-139 bpm | 0 | 00:00:00 |
| Zone 4: | 139-155 bpm | 0% | 00:00:00 |
| Zone 5: | 155 bpm | 0% | 00:00:00 |

FIG. 7A

Now Viewing: Trudy Podobas (Age: 63)

Exit Patient Record

Heart | ECGs | SBP/DBP | Glucose | Weight/BMI | VO2 Max | Fall Detection

Chart | Timeline | Readings

| Date | Time | Classification | Systolic | Diastolic | Unit | Device |
|---|---|---|---|---|---|---|
| November 26, 2019 | 10:47:01 AM | Hypertensive (Stage 1) | 135 | 69 | mmHg | |
| November 26, 2019 | 10:42:46 AM | Hypertensive (Stage 2) | 140 | 75 | mmHg | |
| November 20, 2019 | 9:01:19 AM | Normal | 100 | 57 | mmHg | |
| November 18, 2019 | 2:14:06 PM | Hypertensive (Stage 1) | 131 | 78 | mmHg | |
| November 17, 2019 | 9:09:44 AM | Hypertensive (Stage 1) | 134 | 71 | mmHg | |
| November 17, 2019 | 12:33:28 PM | Elevated | 124 | 63 | mmHg | |
| November 16, 2019 | 11:37:29 PM | Normal | 118 | 71 | mmHg | |
| November 15, 2019 | 10:12:09 PM | Hypertensive (Stage 1) | 134 | 82 | mmHg | |
| November 15, 2019 | 10:05:46 PM | Hypertensive (Stage 1) | 138 | 75 | mmHg | |
| November 14, 2019 | 9:41:31 PM | Hypertensive (Stage 1) | 130 | 71 | mmHg | |
| November 14, 2019 | 9:38:14 PM | Hypertensive (Stage 1) | 136 | 76 | mmHg | |
| November 14, 2019 | 9:36:50 PM | Hypertensive (Stage 2) | 144 | 75 | mmHg | |
| November 13, 2019 | 9:58:20 PM | Elevated | 126 | 65 | mmHg | |
| August 29, 2019 | 10:36:12 AM | Elevated | 112 | 81 | mmHg | |
| August 29, 2019 | 10:35:18 AM | Normal | 112 | 68 | mmHg | |
| August 25, 2019 | 10:53:53 PM | Normal | 119 | 73 | mmHg | |
| August 25, 2019 | 10:51:48 PM | Normal | 109 | 73 | mmHg | |
| August 03, 2019 | 2:51:54 PM | Normal | 98 | 66 | mmHg | |
| August 03, 2019 | 2:51:11 PM | Hypotensive | 83 | 56 | mmHg | |
| August 03, 2019 | 2:46:40 PM | Hypotensive | 89 | 52 | mmHg | |

FIG. 7I

METHODS AND SYSTEMS FOR SECURELY COMMUNICATING OVER NETWORKS, IN REAL TIME, AND UTILIZING BIOMETRIC DATA

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

This application generally relates to systems and methods for biometric data aggregation and visualization to facilitate physical performance tracking and medical monitoring.

BACKGROUND

Modern personal smart devices can collect a wide range of health and wellness related data, such as heart rate and blood pressure. These smart devices can include mobile devices with native sensors or devices with smart functionalities, such as a smart watch, an external blood pressure cuff, heart rate monitor, or the like, that are able to export collected data to a user's mobile device or the cloud. Accordingly, mobile devices are becoming increasingly important in tracking of health, activity, workout, and fitness data. However, the structure, format, storage, retrieval, and rendering of such data can be limited and not optimized for certain practical utilizations and applications of sensor data (e.g., searching within, comparing between, and displaying the data collected from multiple sources).

SUMMARY

Embodiments of the present disclosure are directed to devices, systems, and methods for secure, reliable, and efficient data communication, sensor data processing, data aggregation and visualization in order to help facilitate physical performance tracking and medical monitoring and to provide feedback which may impact the health of a user. The system described herein may have multiple purposes and capabilities, including but not limited to offering users new ways to explore their own data that may be stored and/or displayed in third party systems within a single interface.

Further details of features, objects, and advantages of the disclosure are described below in the detailed description, drawings, and claims. Both the foregoing general description and the following detailed description are exemplary and explanatory and are not intended to be limiting as to the scope of the disclosure.

An aspect of the disclosure relates to a system that may include: a non-transitory computer storage medium configured to at least store computer-readable instructions; and one or more hardware processors in communication with the non-transitory computer storage medium. The one or more hardware processors can be configured to execute the computer-readable instructions to at least: receive a plurality of user data from a plurality of different sensors, wherein at least one sensor of the plurality of different sensors is configured to measure one or more biometric parameters associated with a user; upload the plurality of user data to a remote server; receive processed data based on the uploaded plurality of user data; select data values from the processed data; determine a graphical representation of the selected data values, the graphical representation comprising a combination chart; determine a tabular representation of the selected data; and cause presentation of the graphical representation and the tabular representation within a graphical user interface on a computer screen. The selected data values can include: a first data value of a first parameter type at a first time, a second data value of the first parameter type at a second time, a third data value of a second parameter type at the first time, and a fourth data value of the second parameter type at the second time.

An aspect of the disclosure relates to a system that may include: a non-transitory computer storage medium configured to at least store computer-readable instructions; and one or more hardware processors in communication with the non-transitory computer storage medium. The one or more hardware processors can be configured to execute the computer-readable instructions to at least: receive a plurality of user data comprising at least one of: sensor data from a plurality of different sensors, wherein at least one sensor of the plurality of different sensors is configured to measure one or more biometric parameters associated with the user that is indicative of an infectious disorder; and input data from a device of the user, the input data comprising at least one of a presence or severity of symptoms associated with the infectious disorder; upload the plurality of user data to a remote server; receive processed data based on the uploaded plurality of user data; select data values from the processed data; determine a graphical representation of the selected data values, the graphical representation comprising a combination chart; determine a tabular representation of the selected data; and cause presentation of the graphical representation and the tabular representation within a graphical user interface on a computer screen. The selected data values can include: a first data value of a first parameter type at a first time, a second data value of the first parameter type at a second time, a third data value of a second parameter type at the first time, and a fourth data value of the second parameter type at the second time.

An aspect of the disclosure relates to a system that may include: a non-transitory computer storage medium configured to at least store computer-readable instructions; and one or more hardware processors in communication with the non-transitory computer storage medium. The one or more hardware processors can be configured to execute the computer-readable instructions to at least: receive a plurality of first patient data comprising: sensor data from a plurality of different sensors, wherein at least one sensor of the plurality of different sensors is configured to measure one or more biometric parameters associated with a first patient that is indicative of an infectious disorder; and patient input data from a device of the patient, the patient input data comprising at least one of a presence or severity of patient symptoms associated with the infectious disorder; process the plurality of first patient data for display within a graphical user interface on a computer screen; receive a request from a user to display at least some of the plurality of first patient data; determine a authentication access level associated with the user; and cause, based on the authentication access level, display of the at least some of the plurality of first patient data on a device of the user.

An aspect of the disclosure relates to a system that may include: a non-transitory computer storage medium configured to at least store computer-readable instructions; and one or more hardware processors in communication with the non-transitory computer storage medium. The one or more hardware processors configured to execute the computer-readable instructions to at least: receive a plurality of first patient data from a plurality of different sensors, wherein at least one sensor of the plurality of different sensors is configured to measure one or more biometric parameters associated with a first patient that is indicative of an infectious disorder; process the plurality of first patient data for display within a graphical user interface on a computer screen; receive a request from a user to display at least some of the plurality of first patient data; determine a authentication access level associated with the user; and cause, based on the authentication access level, display of the at least some of the plurality of first patient data on a device of the user.

BRIEF DESCRIPTION OF THE DRAWINGS

Throughout the drawings, reference numbers are re-used to indicate correspondence between referenced elements. The following drawings and the associated descriptions are provided to illustrate embodiments of the present disclosure and do not limit the scope of the claims.

The drawings illustrate the design and utility of various aspects of the present disclosure. It should be noted that the figures are not drawn to scale and that elements of similar structures or functions are represented by like reference numerals throughout the figures. In order to better appreciate how to obtain the above-recited and other advantages and objects of various embodiments of the disclosure, a more detailed description of the present disclosure briefly described above will be rendered by reference to specific embodiments thereof, which are illustrated in the accompanying drawings. Understanding that these drawings depict only typical embodiments of the disclosure and are not therefore to be considered limiting of its scope, the disclosure will be described and explained with additional specificity and detail through the use of the accompanying drawings in which:

FIGS. 4A-4D illustrate example aspects of a user facing graphical user interface associated with a system that may be displayed on a user device having a larger screen than a mobile device.

FIGS. 4E-4M illustrates example aspects of an interface associated with visualizing a single workout.

FIGS. 5A-5J illustrate example telehealth aspects of an interface.

FIG. 5K illustrates example medical records aspects of an interface.

FIGS. 7A-7I Illustrate aspects of an example healthcare provider facing interface.

DETAILED DESCRIPTION

A. Example Data Aggregation Environment

Figure 1:
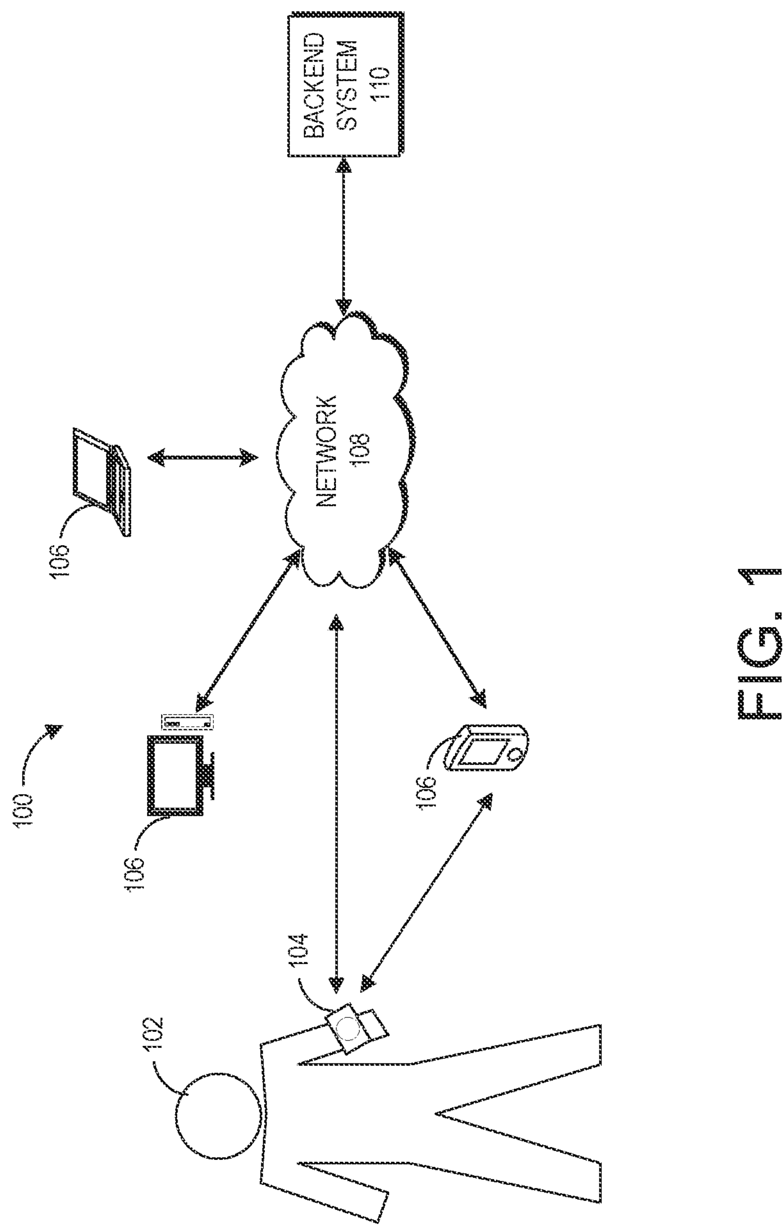
FIG. 1 illustrates a block diagram of an example data aggregation environment.

FIG. 1 illustrates an example data aggregation environment 100 that may make practical use of the data communication, sensor data processing, data utilization, data aggregation, data visualization systems and methods described herein. For example, in the illustrated environment 100, one or more data collection devices 104 may collect data associated with a user 102. The data collection devices 104 may include one or more sensors that may be used to monitor health and exercise conditions and parameters of the user. Example sensors may include optical heart rate sensors, electrical heart rate sensors (e.g., to take ECG readings), accelerometers and gyroscopes (e.g., to measure movement, walking, to detect falling), a GPS radio (e.g., to detect position and movement), and/or other sensors. The one or more data collection devices 104 may securely communicate with a backend system 110 through a network 108. Additionally or alternatively, the one or more data collection devices 104 may communicate with one or more user devices 106 (e.g., smart phones, tablet computers, laptop computers smart watches, other mobile and wearable devices, desktop computers, networked televisions, networked game consoles, and/or the like). The one or more user devices 106 may communicate with the backend system 110 through a network 108.

The data collected by the one or more data collection devices 104 can include a plurality of data associated with the user, including but not limited to health data, activity data, distance data, and workout data. In some examples, health data can include data obtained using one or more of the sensors described herein (and/or other sensors), such as heart rate, average heart rate while walking, resting heart rate, heart rate variability (including instantaneous beats per minute), blood pressure, glucose, VO2 maximum, number of times fallen, weight, body mass index, oxygen intake, oxygen volume, symptoms and their severity, the like or a combination thereof. In some examples, activity data can include a daily activity summary, number of active calories burned, number of resting calories burned, step count, flights of stairs climbed, minutes of time where the user was physically active, instances per hour where the user physically stood up, the like or a combination thereof. In some examples, distance data can include walking or running distance, cycling distance, swimming distance, the like or a combination thereof. In some examples, workout data can include workout type, workout duration, workout distance, workout calories burned, GPS data (including, for example, latitude and longitude), swimming strokes, style of swimming stroke (such as butterfly or freeform), number of laps, length of pool, workout route, workout events (such as pause and resume), the like or a combination thereof.

The one or more user devices 106 can include a device associated with the user 102 of the one or more data collection devices 104, a device associated with a health care provider, a third party user, a user's employer, the like or a combination thereof. In some examples, the one or more user devices 106 may upload (e.g., via an encrypted communication channel), download (e.g., via an encrypted communication channel), stream (e.g., via an encrypted communication channel), display, analyze, read, write, access, or otherwise interact with data associated with the user 102, such as the data collected by the one or more data collection devices 104, data stored in the backend system 110 or other remote, non-local storage location, or data locally stored on the user devices 106.

In some examples, the backend system 110 can include one or more hardware processors and/or storage systems capable of upload, download, display, analyze, read, write, access, or otherwise interact with the data or information associated with the user or other information associated with displaying and/or analyzing the data or information associated with the user. In some examples, data collected and/or processed within the data collection environment 100 may be from a plurality of sources (including disparate sources of different types) and have a plurality of data types. Advantageously, the backend system 110 may enable a user, such as the user 102, to aggregate, transform, and display data collected from multiple sources in a single application. Thus, a user device 106 may, for example, be configured to map data from different sources in order to recognize correlations and/or changes in biometric data that may not otherwise be apparent and which may not be perceptible to a human looking at the same data. Additionally or alternatively, such data may be aggregated and displayed in useful and efficient ways for different types of users (e.g., based on one or more user characteristics). For example, a user 102 may be a patient of a healthcare provider. The systems and methods described herein may provide display and provide access to the analyzed and aggregated data to both the patient and the healthcare provider such that the healthcare provider may be provided more detailed or different information than the patient in order to facilitate treatment of the patient. Such an approach reduces the amount of network bandwidth needed to transmit data to the user device 106 and the amount of display area needed to display data on the user device 106 (which is especially advantageous for small displays, such as may be found on a phone or wearable), thereby overcoming a technical hurdle in the efficient transmission of data and in the efficient utilization of display real estate.

Figure 2:
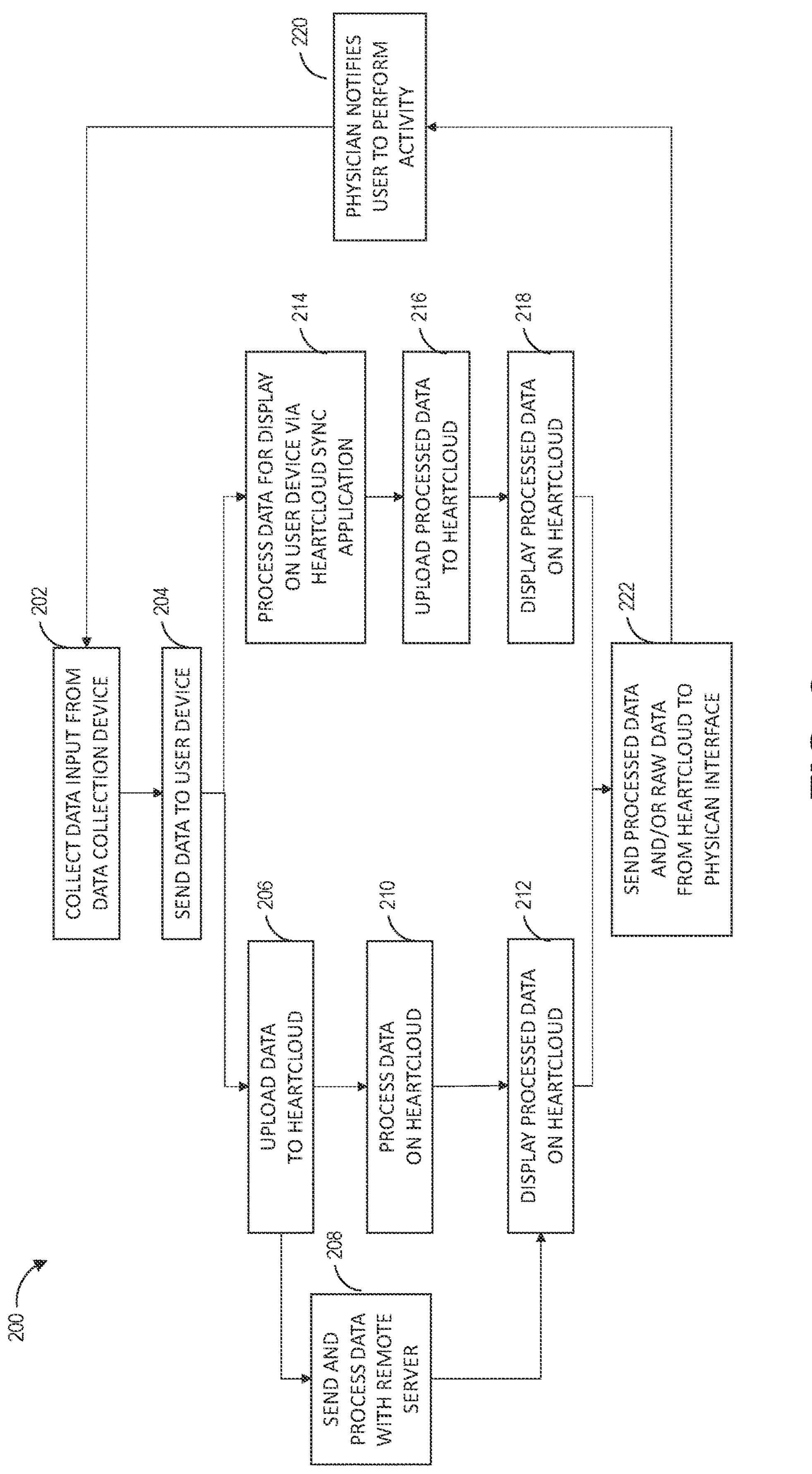
FIG. 2 illustrates an example data flow process.

FIG. 2 illustrates an example data processing, aggregation and visualization process 200 that may be part of a data collection environment 100. In the illustrated example, a system 110 may facilitate a healthcare provider or physician interaction with aggregated data in order to aid the healthcare provider with providing care to a user based on aggregated data associated with a user.

For example, at a block 202, one or more data collection devices 104 may collect data associated with a user, such as health data, activity data, distance data, and/or workout data described above. In some examples, the one or more data collection devices 104 can include smart devices capable of collecting activity information or biometric data, such as a smart watch, smart phone, step counter, glucose monitor, blood pressure cuff, the like or a combination thereof.

At a block 204, the one or more data collection devices 104 and/or the user may communicate the collected data to one or more user devices 106. The one or more user devices 106 may communicate different types of data in different or the same ways, such as over a wired connection or wirelessly (such as over Bluetooth, wireless network connection, NFC, or through other wireless communication). Advantageously, the data may be securely encrypted for communication and decrypted upon receipt. The data may be communicated and stored in a HIPPA (Health Insurance Portability and Accountability Act)-compliant manner and/or according to other legal requirements. In some examples, the user may communicate data to the user device via manual input. For example, the user may manually edit or add entries of data or data types collected by one or more data collection devices 104. In some examples, the user may communicate data to the user device not collected by one or more data collection devices 104.

At a block 206, the one or more user devices 106 may aggregate the data in local storage on a user device. In some examples, the data may be uploaded or streamed (e.g., via an encrypted communication channel) to a user device and/or application on a user device. The application may be configured to receive and/or pre-process data (e.g., perform normalization and/or unit conversions) from multiple data sources, such as multiple data collection devices 106. Advantageously, the application may act as a hub for collected data that may otherwise be received and processed by multiple applications or systems, thereby reducing network utilization and the number of computer and network devices that would other need to engage in the communication of such data to multiple systems and applications.

At a block 210, an application may process the aggregated data in real time or in batch mode (e.g., at scheduled time, or when the user device 106 processor utilization Cis below a threshold amount or percentage of maximum processor availability, thereby reducing peak processor loads). For example, the application may process the data for display. Processing the data for display may include applying one or more filters, selecting data, correlating or pairing data (for example, different types of data from different sources/sensors, but having certain common characteristics, such as heart rate and step count data from matching periods of time) or otherwise processing the data (which may reduce the amount of graphics processing unit resources needed to render data). The foregoing processing may be performed in response to one or more previously defined rules, such as rules defined by a user via a corresponding user interface. For example, a rule may define what types of data should be paired and what data filtering operations should be performed. It is understood that the phrase “pair” may include an association of more than two types of data or data from two different sources.

Additionally or alternatively to block 206 and/or block 210, at a block 208, the one or more user devices 106 may communicate data to a backend system 110 through a network (e.g., via an encrypted communication channel). In some examples, the data may first be pre-processed (e.g., by performing data normalization and/or unit conversions) on a user device prior to communication. In some examples, the data may be transmitted at regular intervals of time. For example, the data may be automatically transmitted every few minutes or hours, or every day. The transmission period may optionally be selected so as to reduce battery power utilization of the user device 106, while still ensuring that data is transmitted to the backend system 110 before being overwritten in the user device by additional sensor or other data. Additionally or alternatively, data may be transmitted upon request by the backend system 110, the user, or the healthcare provider, thereby ensuring that the most recent data is available when needed. Optionally, the data may be automatically transmitted in substantially real time from a user device 106 to a backend system 110.

At a block 212, an application may display processed data from block 208 and/or 210 on a display of the user device. For example, the application may display data in graphical display and/or tabular display. In some examples, the data may be formatted to display differences or changes in data over a period of time, such as before and after a workout regimen or a treatment plan has been implemented. Advantageously, the data may be displayed to illustrate performance differences or other types of progress, such as contrasting calories expended during a particular type of workout or performance differences during different conditions (such as on a cool or hot day).

Additionally or alternatively, at a block 214, aggregated data may be processed for display locally on a user device through a sync application associated with a display application. In some examples, the sync application may preprocess the data for display on the display application by, for example, applying one or more filters, selecting data, correlating or paring data (for example, heart rate and step count data from matching periods of time) or otherwise processing the data.

At a block 216, the sync application may communicate with the display application to upload data for display and/or access. At a block 218, an application may display processed data from block 216 on a display of the user device. The display of data may be similar to the display described with reference to block 212 described above.

At a block 222, an application and/or backend system may send processed data and/or raw data to a physician or healthcare provider device. In some examples, an application and/or backend system in communication with the application or physician device may process and/or display the aggregated data in a manner useful to the physician and/or healthcare provider in providing treatment to the user. For example, a physician may prescribe a diet and exercise regime in order to lower a user's blood pressure. Data may be aggregated and processed relevant to the effectiveness of the diet and exercise regime on blood pressure data. For example, a system may display blood pressure data before and after an implementation of the treatment regimen, which may in turn affect the implementation of a future treatment regimin. In some examples, the displayed data may be the same or different than the displayed data for the user.

At a block 220, an application on a physician or healthcare device may notify the physician or healthcare provider of one or more flagged issues (such as trends or conditions) in the processed data. For example, the processed data may provide that the treatment regimen is not being followed or is proving ineffective. The application may notify the healthcare provider, optionally in real time, of the flagged issue (e.g., via a browser interface, a short messaging service/multimedia messaging service notification, via email, and/or other communication channels). The healthcare provider may then notify the user to update the treatment regimen or otherwise change their behavior in order to provide a more effective treatment.

B. Example Data Sources

As referenced above, data collection devices 104 can include wearable data collection devices (for example, a smart watch, a blood pressure measuring cuff, pulse oximeters, accelerometers, gyroscopes, glucose monitoring devices, the like or a combination thereof) and non-wearable data collection devices (for example, a smart scale, smart phone with a step counter, the like or a combination thereof), to collect user data such as heart rate, average heart rate while walking, resting heart rate, heart rate variability (including instantaneous beats per minute), EKG readings, blood pressure (e.g. systolic and/or diastolic), glucose, insulin, blood sodium level, chemical concentration levels [e.g. iron], VO2 max, fall data, weight, BMI, oxygen intake and volume, DNA, finger prints, palm prints, facial recognition data, voice data, retina or iris recognition data, gait data, balance data, drug level concentration, blood CO2, blood O2, blood Hb levels, other types of measurable or recordable medical data such as symptoms of a disorder, and the like or a combination thereof) and other collectable data measurements (e.g. GPS data, speed, temperature, humidity, weather conditions, latitude, longitude, altitude, course, and/or the like).

In some examples, data collection devices use sensors to collect information associated with user activities beyond biometric data for purposes of data collection for health, workout, or activity tracking. For example, these data collection device can collect activity data related to daily activity summaries, active calories burned, resting calories burned, step count, flights of stairs climbed, minutes of time where the user was physically active, instances per hour where the user physically stood up, and the like or a combination thereof. For example, these data collection devices can use sensors to collect data showing whether a user is walking, running, cycling, swimming, and the like or a combination thereof. For example, these data collection devices can collect data according to workout types (e.g., walking, running, rowing, stair stepping, yoga, swimming, cycling, high intensity interval training, wheelchair rolling, hiking, elliptical running, the like or a combination thereof) and/or workout duration, distance, calories burned, and other types of relating to specific types of workout, swimming stroke type, the number of swimming strokes, laps traveled, length of distance travelled, workout routes, and other workout events (for example, pause, resume, uphill, downhill, the like or a combination thereof).

The data collection devices can utilize wireless methods such as Bluetooth and/or Wi-Fi, or wired connections (for example USB, micro USB, the like or a combination thereof) to transmit readings taken from the biometric collection devices and transfer the data to a user device, computer, or cloud, for data processing and/or storage. Data can then be stored in data storage API layers on a user device. These data storage API's can define and enforce how health, workout, and activity data is structured, formatted, stored, and retrieved. The data transmission may optionally be performed using data channels employing symmetric encryption (where the same secret, private key is exchanged and used for both encryption and decryption) or asymmetric encryption (where the sender uses the public key of the recipient to encrypt the message, and recipient uses its private key to decrypt the message).

However, not every data collection device utilizes the same type of data storage API. Thus, conventionally, users may be forced to utilize multiple applications to keep track of their biometric and activity tracking data, which in addition to be inconvenient, such multiple applications may utilize a significant amount of a device's non-volatile memory for application storage. For example, a smart watch may collect much of the data above relating to physical activity of a user. However, a glucose monitor used by a diabetic patient may not write to the same device data storage API, thus forcing a user to utilize two different applications for tracking of health-related data. This separation can be burdensome for users and may significantly load a device's hardware resources. The systems and methods described herein can allow a user to aggregate data from multiple sources that may otherwise require different tracking applications due to separate device data storage APIs to a single application. Advantageously, this aggregation may allow a user to view and identify a broader picture of their health and activity data in a single hub or location, while reducing computer and network loading. Additionally, this aggregation can be shared with a third party, such as a healthcare provider, in order to aid in treatment programs of a patient. Additionally or alternatively, such data aggregation may advantageously allow for early detection of infectious disease through the sharing of information relating to changes in a user's temperature, blood oxygenation, heart activity, or the presence or absence of symptoms, and hence the quick and resource-efficient treatment of such disease.

Advantageously, systems and methods described herein utilize distributed computing that may reduce computational load on a server and the amount of data being transmitted to a server through preprocessing of data. For example, the system may perform a certain amount of processing of collected data on a user's mobile device before the data is transmitted to a server or a backend system. Advantageously, this preprocessing may, for example, lessen the size of data packets transmitted to a server and improve user experience by facilitating faster retrieval, searching, and analysis of potentially large amounts of data. Further, data compression techniques may be used to further reduce the amount of memory needed to store and/or the network bandwidth utilization needed to communicate such data. For example, media compression (e.g., lossy data compression) may be used for images, and file compression (e.g., lossless data compression) may be used for other types of data. Thus, the type of compression may be selected based on the type of data being compressed and/or depending on whether lossless compression is needed to ensure no data is lost, or whether lossy compression may be utilized to further reduce memory and/or network loading.

C. Example Data Search Functionality

A system can include a search engine that may be free of involvement of a backend system. Advantageously, this may allow a user to search, process, and retrieve data locally for any number of data categories within any number of date and time ranges or within any number of other search parameters, advantageously even in the absence of network availability to communicate with the backend system. Local retrieval of data may allow a user to access and analyze their data offline and without reliance on the speed and availability of a third party system. This technique overcomes the technical challenge of enabling data to be searched for and retrieved even when the user is in an area where wired or wireless computer networks are unavailable, such as when a user may be hiking, camping, or boating in a remote location. For example, due to the sheer amount of potential data inputs, a number of operations can be performed by a system or a backend system to ease and enable future use and access (for example redisplay, search, manipulation) of massive volumes of high-density data (i.e. data with a high number of recorded samples) much more efficiently and quicker than may be otherwise available. This can contribute to a better user experience because the application can operate faster. For example, by saving data that has been pre-processed and aggregated by the system or backend system, the user-driven search query can be performed much more rapidly than other data search alternatives. The search query is more rapid in part because the crunching of the voluminous raw data is done once and saved in various useful formats, and therefore does not have to be crunched each time a query happens. Conventional search systems perform queries in real time, while the user is waiting, and so this pre-processing/digestion/aggregation step allows for a much superior user experience by reducing wait times.

In some examples, a system may utilize a date, time, or time zone provided by another system from which it is retrieving data (for example, "2019-07-01 23:21:48-0700") of one or more readings to extract the data based on this full date, time, and time zone format: year-month-day ("2019-07-01"), year-month ("2019-07"), year (2019), year-WeekIn Year ("2019-27"). When inserted as a database row, the original reading from the user device is optionally unaltered, but can include additional information derived from its original content, such as biometric data, UNIX time stamps, time zone information, or derivations that would convert "2019-07-01 23:21:48-0700" into week-year (27-2019), a year-month-day (2019-07-01), a year-month-day-hour (2019-07-01-23), or year-month (2019-07) based on standard formatting (such as International Standard ISO 8601), the like or a combination thereof. In the foregoing examples, a hyphen separates elements of different date and/or time periods (such as month[hyphen]year), but this method is not restricted to the use of a hyphenation character. A purpose of this processing step prior to insertion into a database or other storage system is that queries across large-scale time periods for high-density data, such as heart rate or step count need not convert the column containing the value of the full startDate or endDate date, time, and timezone into other formats (such as a week-year, year-month-day, year-month-day-hour, or year-month). Voice, text, or other queries by a user to retrieve data (for example, in a particular format from a database or other storage system) across relatively large time periods (for example, months or years, such as "the last 7 months of heart rate data grouped by day for this year") can use pre-formatted values instead of needing to consider the impact of dates, times, and time zones. In another example, a physician may wish to know, for one or more patients, information such as "the total quantity of heart rate measurements each day that exceeded 140 beats per minute, grouped by the total number of instances within each of the 24 hours within a day, over a number of days between two calendar dates.". Such a query can use the year-month-day-hour, year-month-day, and week-year columns to provide the requested information in a chart, data table, or other visualization medium. Advantageously, these and other processing steps may yield performance gains, such as reduced processing time, improved performance of single or multi-column database indices, reduced system crashes, and can mitigate against performance risks inherent in database-driven web applications (such as increased waiting times for pages or elements within pages to load, session or page timeouts, among other performance bottlenecks) caused by multiple users authenticated into separate accounts within a single application making simultaneous or near-simultaneous queries to a database or other persistent storage layer to return information across large time periods.

In some examples, high-density data can be collected and inserted into tables that track daily aggregated statistics. For example, useful daily heart rate statistics include the maximum, minimum, and average beat per minute value. If a user imports data from their weekend hiking in a national park with no internet connection, they could conceivably upload a batch containing 2800 heart rate readings measured across 3 days. But the user's next upload after they just return to an area with improved internet coverage might contain 172 heart rate readings from within only the last few hours. The system seamlessly can address these scenarios to aggregate statistics per batch of uploaded data. Therefore, when a user or their physician (or other authorized medical service provider), requests via their devices daily heart rate statistics over the past year, the application may use pre-calculated values to return results instead of reading through hundreds or thousands of rows of data thereby improving application functionality and speed.

D. Example Data Visualization Functionality

A system can include one or more charts or display formats for user data that is unavailable in a proprietary data tracking system associated with a data collection device.

Advantageously, the system can generate and provide for display more intuitive and interactive charts than conventionally available. Additionally, the one or more charts or display formats may facilitate a much faster and easier navigation of large amounts of aggregated data on a limited display, such as a mobile device screen or web browser. In particular, the data visualizations disclosed herein improve data display, comparison, and navigation on small screens (e.g., less than 8 inches in the diagonal for smart phones, less than 2 inches in the diagonal or in diameter for a smart watch) by allowing a user to quickly access and understand aggregated information on a single chart and/or table. For example, in some visualizations described herein, such as FIG. 4M described below, a plurality of collected parameters may be displayed in a graphical format so as to facilitate day to day comparison between each parameter within a single screen. The system is also configured to generate interfaces showing different data across longer periods of time for purposes of comparing and contrasting various information, such as comparing two or more health, activity, or workout data types over a minute-to-minute, hour-to-hour, week-to-week, month-to-month, or year-to-year basis. Other examples of improved data visualizations are also described herein.

In some examples, the one or more charts or other display formats may display multiple categories of data on a single graph. The source of this data visualization may optionally be from commercial, open-source, or partially open-source data visualization libraries. Advantageously, this may allow for a user to visualize relationships between multiple different categories of data that may otherwise not be possible without the data aggregation. For example, a system may chart the relationship between exercise minutes per day, resting heart rate, and quantity of workouts per day. It is particularly useful to display data that reflect complementary aspects of health, such as exercise and heart rate or another pairing of data that may have a relationship. For example, the system may be configured to display average daily resting heart rate along with daily duration of exercise (both on y-axis, with x-axis being date) to permit the user to see how resting HR improves (for example, is on a lowering trajectory) as the amount of time spent exercising accumulates.

In some examples, the system may display representative values for a display period. The representative values can include an averaged value, weighted average, a selected value, or other representative value of a data type over a desired period of time, such as one or more days, hours, weeks, months, years, or other period. For example, a system may display daily averages instead of every-data-point (which could be hundreds per day) making it easier to see the information on a smaller screen. A visualization may change in relation to the time frame being displayed. For example, a system may be configured to display one value per day when looking at a plurality of days of data or to display every data point if only looking at a two-hour or other smaller window of time.

In some examples, graphs may be overlayed. In some examples, graphs may not be overlayed. For example, one or more graphs may be displayed separately. The separate graphs may be displayed in a vertical or other stack so that one or more axes of the graph align. For example, the graphs may be displayed in a vertical stack so that the time axis lines up. In this way, a user may be advantageously be able to scroll through or otherwise view a number of graphs without having to modify the scaling of the graph. This may facilitate easier comparison of data.

The present system is capable of displaying data in at least four formats: all readings between two distinct pairs of dates, times, and timezones or trend-based visualizations in three aggregated timeframes: day-to-day, week-to-week, and month-to-month data. The data that can be shown may be selected by a user or the system from data types, such as heart rate, heart rate variability, resting heart rate, metabolic equivalents (METs), heart rate zones, blood pressure, glucose, exercise and other activity levels. Some of this data may be captured by a smart watch or fitness tracker and other data may be captured by specialized digital health devices or medical devices (which may or may not require a prescription).

Physicians practice across a wide range of specialties and medical knowledge is constantly being produced and re-assessed. Therefore, the system disclosed herein may allow clinicians, whether generalists or specialists, to arbitrarily select one or more of various types of health, activity, workout data, or other health information in order to help clinicians view and analyze data they deem relevant (which may or may not be standardized or changed based on clinician or other user preference). The system may allow a clinician to choose, at least in part, how selected data is organized.

The system may organize data that is uploaded or otherwise made available to the system by a patient. The organization of data may include displaying selected or queried results or rendering the same by day-to-day, week-to-week, or month-to-month averages, minimum, and maximum values. This flexibility is facilitated by how the data aggregation's systems software applications convert the month, day, year, hour minute, second, milliseconds, and timezone offset of original measurements by "year-month-day," "year-month," "ISOweek-year," and "year". This enables clinicians to search for and visualize patient data across long periods of time because database queries are capable of organizing daily, weekly, and monthly trends across voluminous heart rate, exercise time, glucose, blood pressure, and other data categories if pre-formatted "year-month-day," "year-month," "ISOweek-year," and "year" representations are stored alongside original measurement data. It may be particularly useful in some clinical circumstances to display data that reflect complementary aspects of health; for example, a clinician might wish to display average daily resting heart rate along with daily duration of exercise (both on the y-axis, with x-axis being date) to reveal how resting heart rate changes as the amount of time spent exercising accumulates over the span of several weeks.

Additionally or alternatively, the system may display data in multiple ways. For example, a system may both graphically chart and present a tabular presentation of the same chart within a single screen or on interconnected screens. In some examples, a system may blend graphical display and tabular data to support users in their efforts to deeply understand their health and wellness. Thus, the system may allow users to use predefined analyses as well as on-the-fly queries and present the findings in a clear, concise, and compelling visual display. Such displays may then be visible online or on the user's device or saved as image files, as PDFs, or in other formats for future accessibility.

In some examples, the system may have visualization functionalities that generate user interfaces that facilitate comparison of data between two conditions, whether that is performance before and after instituting a new workout regimen, contrasting calories expended on a run vs a swim workout, heart rate recovery between the same workout type (for example, comparing two or more runs) or between different types of workouts (for example, comparing a run with a swim or a run, walk, and a swim) swims, or cycling performance differences on a cool day vs a hot day (since the system is configured to retrieve and present a wide range of environmental conditions that may have occurred between the start and end of a workout, including, but not limited to, barometric air pressure, wind speed and direction, temperature, and ultraviolet (UV) index and ozone levels). Similarly, the same or other visualization functionalities can be used to apply to a clinical context and generate corresponding user interfaces: resting heart rate and blood pressure before and after a medication adjustment, activity levels day-by-day after a surgical procedure, and METS (metabolic equivalents) before and after a preoperative optimization change in treatment plan.

Advantageously, when there is a comparison of two different states (for example, blood pressure before a medication is added and after it is added) the visualization functionality can show a clear demarcation of the before and after an event (or dividing line). In an example of a comparison of heart rate (HR) during a swim workout and a cycling workout, then the HR values are clearly distinguished for swim as opposed to cycling. When a data visualization is a temporal comparison, (for example, an average speed when running on January 1, 2, and 3), then the data can be shown continuously rather than with clear demarcations or other visual cues that different states are being compared.

As referenced above, conventional applications specific to data collection devices may not allow such aggregation and analysis, such as the search capabilities described herein, leaving users to stare at data points in isolation, whip out paper and pencil to record the numbers, or show screenshots to their physicians to decipher in providing treatment programs to the user. In contrast, using the disclosed systems and processes, a physician or healthcare provider (or their systems and devices) may be able to access, filter, compare, and analyze user data easily for use in generating treatment options, monitoring patients, or for other uses. For example, these improved data summary interfaces can quickly allow a user to access and study data entries of an individual based upon searching for measured clinical context data (e.g., heart rate, temperature, elevation glucose level, etc.). In one example, using the disclosed systems and processes, if a physician suspects a user has a certain disease, the physician can use an aggregate of clinical context filtering data that represents symptoms of the diseases to quickly review all similar data entries to see if there indeed a pertinent pattern of data. Similarly, if the physician would like to add or remove symptom related data, the summary interfaces are configured to easily and quickly enable the physician to alter the clinical context data. The physician can then instruct the system to automatically identify and report similar occurrences when the user outputs similar data. Thus, the system may be trained to learn what sets of data are significant and are to be identified.

In another application, processing, aggregation and real time access of user and/or patient data may facilitate improved healthcare treatment and monitoring by providing cased access to real time and real world health data. This is an improvement over traditional patient data collection and access options, in which a healthcare provider may have to order tests in a controlled environment or review potentially outdated information stored in a user's medical history. For example, traditionally, data collection of a patient is done in a controlled lab setting where the physician applies a battery of stress tests to the user (e.g. treadmill running to gather heart rate). However, these tests are usually conducted in controlled settings and the data produced can be unrepresentative of actual real world situations. Advantageously, using the summary interface feature, a physician or healthcare provider can use real time data (such as that disclosed herein) of a user in a real life setting. The healthcare professional can then have multiple sets of real world data to properly diagnose the user rather than relying on data collected from a single lab control setting. Utilizing real world and real time data can also facilitate more accurate results in testing and make it less likely to obtain skewed results due to a controlled setting. Additionally, utilizing real world and real time data can save both patient and healthcare provider time in treatment of health conditions as patients and healthcare facilities may no longer be required to put time aside for performance of laboratory tests in a clinical care setting.

E. Example Telehealth Functionality

The systems and methods described herein can facilitate telehealth solutions to user healthcare. For example, systems and methods can advantageously offer participatory and real time interaction with user data for a user and/or a user's physician (or other healthcare professional). In some examples, the disclosed systems and processes enable a physician to engage with at least one individual person using real-time audio and video protocols. Advantageously over other telemedicine solutions, the disclosed systems and processes enable a clinician to simultaneously view a live visual image and audio of a patient and a vast amount of data sourced from a combination of sources. Additionally, patient data (such as physiologic data but also clinical data from their medical records, such as lists of medications, allergies, diagnoses) is generally not available in other telehealth systems. Advantageously, the present system makes it easy for a clinician to search and visualize patient data while engaged in the conversation with the patient during a telehealth session (or over an audio visual link).

The combination of sources can include, but is not limited to non-prescribed wearable devices (such as an Apple Watch), prescribed wearable devices (such as a glucometer, continuous analyte monitor, or insulin pump), non-wearable non-prescribed digital health devices (such as a portable blood pressure cuff), data stored in external electronic health records systems including, but not limited to Epic, AllScripts, Cerner, eClinicalWorks, Medicare, and Medicaid, and/or other sources of health related information. In some examples, data available to a physician can encompass notes taken by clinicians other than the one conducting a present telehealth session or visit, past laboratory test results, past diagnostic tests, medications prescribed, the like or a combination thereof. The access of audio, visual, and patient data can be simultaneous or synchronous. Additionally, each capability can operate independently to provide its respective function and does not rely upon the other capabilities to operate.

In some implementations, a user and a healthcare professional can participate in a real-time audio-visual telehealth call through one or more graphical user interfaces while, simultaneously, the healthcare provider can review and interact with graphically visualized data from collected data utilizing the disclosed systems and methods. The user interfaces may be configured to reduce the need of users to navigate via large numbers of interfaces and may efficiently present data suitable for a relatively small display, such as a phone display, a watch display, or the like.

In day to day medical practice, many patients will contact their physicians about a past bodily event or sensation that might have one or more deleterious health implications. However, it can often be difficult for a healthcare provider to establish a diagnosis or provide treatment for such ailments as patients may communicate with their physicians using subjective diction that lacks standard meaning or quantifiable metrics (for example, how much pain, how much did your heart rate fluctuate and in what way(s)). Additionally, patient complaints are often unaccompanied by data to support claims that the patient makes, making it more difficult to formulate a treatment plan. Furthermore, a medical professional may have difficulty determining, specifically, the date(s) and time(s) of one or more past medical events that a patient claims to have experienced. In contrast to other telehealth software applications, the systems and methods described herein allow a clinician to visualize data from wearable devices that the patient has uploaded to their user account and data from medical records that the patient has linked to their account using external patient portals.

The systems and methods described herein improve upon traditional telehealth and in person medical treatment by facilitating real time access to patient activity and health data that may be relevant to a past patient complaint and may otherwise not have been easily accessible by the healthcare provider. Additionally, the systems and methods described herein may enable a healthcare provider to access real world and real time data associated with a patient. For example, a healthcare provider may be able to communicate a request (via an application hosted on a user device or otherwise) that a patient perform basic tests, such as walking up and down stairs, during a telehealth call and simultaneously, in real time, read biometric data collected by a patient's data collection device. This may facilitate better and more targeted health care as a healthcare provider may be able to rule out or identify issues in real time.

To provide even more information for a clinician to evaluate during a telehealth visit, the system described herein may be configured to display, to a clinician user or other authorized user, medical records for a specific patient. Advantageously, the system may be configured to format data for display from a plurality of medical record sources. For example, a single individual may see one physician for primary care and another for specialty care in one or more areas. These healthcare providers may use different medical records software from different companies, resulting in fragmentation of the medical record's information. To address this practical problem, the current system may allow individual users the ability to sign into one or more patient portals offered by healthcare providers from which the patient has previously received healthcare services. Upon the patient authorizing the current platform to access data from a specific patient portal, the authorized data from the healthcare provider that provides the patient portal becomes available to the patient and to each healthcare practice that the patient is currently sharing their wearables data with.

In order to facilitate access, a patient user of the present system may request a telehealth visit with a physician, and list one or more complaints associated with the reason they are requesting a telehealth visit. The information that comprises the telehealth visit request may be stored in a single database table while the information that comprises the complaints associated with the telehealth visit request are stored in a second table. By way of example, each telehealth visit request may be stored in a single database table row while each complaint associated with the telehealth visit request is stored in a single row in the second table. In relational database management system terms, a "one-too-many" relationship exists between the telehealth visit requests table row and each row (at least one) of each complaint. Each complaint contains a start date, start time, end date, end time, a data category (e.g., fluctuating heart rate or "lightheadedness") selected by the patient, and a freeform text field for the patient to provide a subjective description of the complaint. The foregoing technique overcomes the technical challenge of enabling data to be stored efficiently and allow data and data records to be quickly identified in response to a health-related query.

Once an audio-visual telehealth call has been joined by both patient and physician, the physician may be presented with each of a patient's complaints (including the data category, start to end dates and times, and any description of that particular complaint that they have written). The system may supplement the visit with data visualizations in the form of JavaScript, HTML, and CSS charts that are sourced from data that the patient has uploaded to the system or connected from one or more medical records from a third party healthcare provider. These visualizations may be presented as interactive charts and/or be facilitated by open-source technologies including, but not limited to, JavaScript (including jQuery, Vue, React, and other JavaScript libraries), HTML, CSS, and AJAX (which enables a user to query arbitrary date ranges during the telehealth visit and display data responsive to their search inquiry).

In order to provide privacy, an initial scope of access to user data may be restricted to the time period between the start time and end time of each complaint. Thus, a healthcare provider may only have access to overlapping or non-contiguous data between each complaint. However, a user may authorize increased access (by, for example, selecting an option to authorize in a graphical user interface associated with the system before, during, or after the audio-visual telehealth call). The increase access may authorize the physician to examine digital health data beyond the scope of the date and time restrictions bounded by one or more of their complaints submitted as part of the telehealth visit request.

In some examples, user data that the physician is given access to interact with is live and simultaneous with the audio-visual call. This live interaction may be accomplished by means of AJAX calls that advantageously do not require a refresh of data to be made through a standard HTTP method call like GET, POST, or PATCH. That allows the physician to interact with a patient's data simultaneous to physically perceiving the patient's appearance, movement, and speech while also interactively communicating with them by video, audio, and/or text. Additionally or alternatively, the physician may be given access to historical or real time user data before, during, or after the audio-visual call. This data may be sourced from whatever health, activity, or workout data that the patient uploaded to the system or made available from other data sources to their account on the system (for example, connecting a third party health data source by means of an API and authentication token).

In some examples, live data provided remotely via the disclosed systems and processes may advantageously enable a physician or healthcare provider to perform basic physical exams in a manner that could not be performed conventionally in the absence of the physical presence of the patient. For example, the system may facilitate evaluation of a patient based on a real time walk test to test patient impairment in either an inpatient or outpatient setting.

F. Automated Billing

As part of a telehealth functionality, a system may automatically select at least one billing code associated with a telehealth or telemedicine visit or session. The system may apply the selected at least one billing code to an invoice associated with the telehealth visit.

A billing code may be selected from a database of billing codes. Current procedural terminology (CPT) and HCPCS levels 1, 2, 3 are the predominant resources for classifying the provision of medical services and durable medical equipment to patients. These codes are routinely included in bills sent to a patient's health insurance provider. Table 1 illustrates 6 CPT codes and the minimum requirements that must be met to obtain reimbursement from an insurance provider. FIGS. 5B-5F also illustrate aspects of data and/or an interface that may be used to help automate billing for a telehealth session.

TABLE 1

Example billing codes and requirements for reimbursement from an insurance provider

| CPT Code | Required License | Duration | Patient Relationship |
|---|---|---|---|
| 97802 | Physician | First 15 minutes of first (initial) visit | Established or New Patient |
| 97803 | Physician | Subsequent 15 minutes | Established or New Patient |
| 99202 | Physician | 15-29 Minutes | New Patient |
| 99203 | Physician | 30-44 Minutes | New Patient |
| 99204 | Physician | 45-59 Minutes | New Patient |
| 99205 | Physician | 60-74 Minutes | New Patient |

During a telehealth visit or session, the system may automatically operate one or more functionalities to help automate billing. In some examples, the system may facilitate automated or semi-automated billing related to a healthcare provider viewing or analyzing patient data. For example, each time that a practitioner opens a patient's file or record in the system, a timer may begin. When the healthcare provider leave the patient's record, the timer may end. Additionally or alternatively, each page that they visit, each date and time range, or event that they peruse may be recorded.

This functionality may apply in the context of a telehealth visit, where information associated with the telehealth visit is recorded. Information may include the date, time, and timezone of each successful or failed connection or disconnection to the telehealth visit, the duration of each connection or times between connections where a participant is not connected, the duration that each participant's camera and microphone are active or are not, and/or, the name and position of the health practice participant (e.g., physician, nurse, psychologist, social worker, etc.) is automatically logged by the present system. The resulting data is a true and accurate reflection of who participated in a telehealth visit or who spent time reviewing a patient's digital health data, and for how long.

A requirement for many CPT and HCPCS procedure codes involving medical services in the form of evaluating digital health data or providing remote care services (such as telehealth) is that the clinician must spend some number of minutes at or exceeding a numeric threshold or between a minimum and maximum range of minutes. Another requirement is that only certain types of credentialed medical professionals (e.g., a physician) can submit a claim using a procedure code that other clinicians cannot employ. Since the present system has a record of which user is a physician, a nurse, etc. and has a record of how much time was spent on remote monitoring and telehealth services, it can perform a logical evaluation of logged data and automatically select a correct procedure code. That information may be automatically collected and formatted such that it can be added to an invoice item on a health insurance billing record. Automated billing may invoice items consistent with the form fields of the UB-4 and CMS-1500 Medicare, Medicaid, 1976 black lung health program, and other documentation generated by private health insurance providers.

In some examples, the system may automatically store time and date information. For example, during the entirety of a telehealth appointment between a clinician and a patient for one or more of audio (or microphone) based communication, video based communication, or other components of the synchronous communication stream, the system can store date, time, and time zone information. In some examples, when a clinician or a patient connects to the same telehealth visit or session, the system may record and store date, time/timestamp, and time zone information associated with the telehealth visit. Time zone information may be stored in a form such as a localized IP address of each participate and/or standardized as if each participant were present in the UTC time zone during a connection or disconnection attempt, regardless of whether the outcome of the intended operation (such as a connect or disconnect) was successful.

Additionally or alternatively, data may be stored upon conclusion of a telehealth visit. For example, information associated with a billing code, such as a CPT code, may be stored and recorded for applying to an invoice or invoice item.

G. Example Infectious Disease Monitoring Functionality

The systems and methods described herein can be used to identify individuals in the early phases of an infectious illness, based on changes in physiologic measures as measured by the user data uploaded to the system. In some examples, a remote monitoring aspect of the system may enable health surveillance of large groups of people so that individuals can be selected for more intensive evaluation and testing, thereby protecting the health of the group as well as the individual. For example, the COVID-19 epidemic placed a strain on in person healthcare and telehealth providers due to the large numbers of patients who either contracted or suspected contraction of COVID-19 and required or desired evaluation by a healthcare professional, including diagnostic testing for the presence of the coronavirus or serum antibodies. Under epidemic or pandemic conditions, traditional telehealth providers may not be able to keep up with patient demand for communications, tests, or other medical services due to the widespread nature of a disease. The systems and methods described herein may case strain on telehealth and in-person healthcare providers (and their computer resources) by facilitating surveillance of large groups of people without individual check-in appointments that may not be necessary if a patient is improving or stable. Thus, a healthcare provider may be able to treat more patients in a more targeted approach and save on limited resources, such as healthcare provider time or testing facilities.

In the management of epidemics by infectious agents, it is useful to identify individuals who may be able to transmit the illness so that they can be treated and can be isolated so as to contain the spread of the illness, the physical locations of such individuals, and concentrations of such individuals.

In recent years, measurement of body temperature elevation has been examined as a mass screening tool, for example during the 2003 SARS coronavirus pandemic and the 2014 Ebola outbreak, particularly as people arrived at airports or other transportation hubs (e.g., Chiang et al., J Formos Med Assoc. 2008). Thermal imaging technology has been employed but has limitations due to factors which can alter the body temperature values, such as evaporation of perspiration, wearing of layers of clothing, and medication effects. More reliable methods, such as checking body temperature with a non-contact or an oral thermometer require an individual-by-individual assessment, which is time consuming and impractical in many settings. Passive data collection from wearable sensors is a more practical approach to surveillance of the large numbers of people who must be monitored for protecting the public health.

Heart rate and heart rate variability (HR and HRV respectively) have been examined in seriously ill individuals in the Intensive Care Units (ICUs) and Emergency Departments (EDs) of major medical centers, and have been found to be altered in those individuals who are likely to suffer severe cases of infectious illnesses such as sepsis (reviewed by Ferrer and Artigas, Crit Care Clin, 2011). Elevated HR (tachycardia) can be an important sign of infection, and can be measured easily via wearable sensors. HRV has been observed to decrease before clinical diagnosis of severe infection has been made (Ahmand et al., PLOS 2009, Arbo et al., Am J Emerg Med. 2020) and be unchanged in those patients who remained well, so can serve as a leading predictor of an infection that has not yet become clinically apparent based on symptom changes. Similarly, pulmonary changes that impair the absorption of oxygen from the lungs may result in decreased levels of oxygen molecules bound to hemoglobin in the red blood cells in an individual's blood. This is measured practically by a pulse oximeter, which estimates the percentage of hemoglobin in the blood that is carrying oxygen from the lungs to body tissues. Healthy saturation levels are ordinarily approximately 95-100%.

To determine whether an individual's HR, HRV, oxygenation, and body temperature are changing in ways that may indicate the presence of an infectious illness, an algorithm may compare past values of these measures with more recent values, and when these changes exceed appropriate thresholds for deviation from the past ("baseline") values, these changes are automatically flagged for examination by a human monitor, for example, an Occupational Health nurse or doctor. Similarly, a user may enter data about the presence and severity of symptoms (for example, cough, loss of sense of smell) and these data may also be flagged for examination by a human monitor. For example, a corresponding notification may be provided to a medical service provider via a medical service provider device or system by an application notification, messaging service notification, email, automatic voice call, or otherwise. When more than one value exceeds a threshold, or a single value exceeds a threshold by a large deviation, then the nurse or doctor may take that individual aside an implement a more complete diagnostic evaluation with lab testing.

Advantageously, certain patient data may be obtained via sensors already being worn by a patient (e.g., a smart watch with various sensing functions), thereby reducing the need to separately manufacture and supply such sensors. Commonly used wearable sensors may include wrist-worn heart rate monitors. These can be made to communicate their measurements wirelessly to cloud-based computational platforms. For example, a wristwatch-like monitor can relay measurements on heart rate and beat-to-beat variability to a mobile device, and the data can be transmitted to a cloud-based system, such as described herein. Advantageously, because this transmittal of data can be automated, it becomes a passive experience for the user and thus does not suffer reliability issues if an individual forgets to send data. Further, if it is determined that a network is not available to transmit such data, the mobile device may be configured to retry transmission once a network is detected and available, thereby ensuring the data is transmitted as soon as practical, and further ensuring data is not lost.

Uploaded data may then be visualized by the patient for self-monitoring and/or a healthcare provider for professional monitoring. In some examples, the system may visualize and/or provide access to data associated with multiple patients or users. Advantageously, this type of access may enable a healthcare provider to monitor a plurality of patients quickly and efficiently and/or flag patients who may develop symptoms or worsen for further treatment. Additionally, using monitoring systems such as these enable greater granular review of tracking individuals' movements and symptoms in order to monitor the spread of a disease in order to allow decision makers to better tailor quarantine policies, travel policies, etc.

Optionally, a map may be generated such the locations of specific individuals that are being monitored, that have been flagged as potentially having a given disease, and/or that have been confirmed to have a given disease. Optionally, heat maps may be generated that show concentrations of people, by location, that are being monitored, that have been flagged as potentially having a given disease, and/or that have been confirmed to have a given disease. For example, the heat map may show the magnitude of the foregoing phenomena as color gradations in two or three dimensions.

Optionally, the location of an individual that has been flagged as potentially having a given disease, and/or that has been confirmed to have a given disease may be continuously tracked and monitored to determine if the individual is following applicable quarantine or safe distancing rules or recommendations. Optionally, in response to detecting that the individual is not complying with quarantine or safe distancing rules or recommendations (e.g., the individual has been detected as leaving their residence, as being less than 6 feet from an individual that has not been determined to have the disease, etc.), a corresponding notification may be transmitted to the individual and/or one or more other destinations (e.g., medical personnel or quarantine enforcement authorities).

H. Example Activity Monitoring Functionality

In some examples, a system may be configured to communicate with physiological monitor(s) or other devices associated with a patient. In some examples, the system may be configured to receive and transmit information to and from a physiological monitor(s). For example, a system may receive one or more signals or other information from a physiological monitor, such as a wearable device. The system may determine, based on the received information, the occurrence of an alert event. The system may then transmit a signal to a physiological monitor, a user, or a third party (such as emergency services) or otherwise cause a physiological monitor, a user, or a third party to change a state of a device based on detection of the alert event. The detection of an alert event may occur when a system detects a parameter failing to pass a threshold value of the parameter (such as falls below a safe threshold or is greater than a maximum safe threshold). In some examples, the alert event may include an event of medical concern, such as detected irregularity in heart rate, a fall detection, a spike in fever, a difficulty in breathing, the like or a combination thereof.

In some examples, a system may be configured to cause the output of an alert. The alert may include, but is not limited to, a control signal configured to cause a device of a user to draw attention of a user. For example, the alert may include a signal configured to cause a mobile phone or wearable smartwatch to emit an audible noise to alert the user of a problem. In some examples, the alert may include a textual alert to a device of a user. In some examples, the alert may include a call to or contact with a user or a third party that may be identified by the system as a likely source of help for the user experiencing the alert event. Other alerts are also possible.

In some examples, a transmitted signal may include a control signal to cause a change in the functioning of a device associated with the user experiencing the alert event. For example, if a user's heart rate has increased enough to pass an alert threshold, a system may cause a physiological monitor configured to monitor heart rate to increase a sampling rate in order to capture more information.

I. Example User Facing Graphical User Interfaces

FIGS. 3A-3D illustrate example aspects of a user facing graphical user interface associated with a system that may be displayed on a user device, such as a mobile device. As discussed above, the data visualizations disclosed herein improve data display and comparison on small screens, such as on a mobile device, by allowing a user to quickly access and understand aggregated information on a single chart and/or table. For example, in some visualizations described herein, such as FIG. 4M described below, a plurality of collected parameters may be displayed in a graphical format so as to facilitate day to day comparison between each parameter within a single screen.

The graphical displays discussed below can alternatively plot and use other measureable biometric data or other measureable data such as heart rate, average heart rate while walking, resting heart rate, heart rate variability (including instantaneous beats per minute), blood pressure, glucose, VO2 maximum, number of times fallen, weight, body mass index, oxygen intake, oxygen volume, a daily activity summary, number of active calories burned, number of resting calories burned, step count, flights of stairs climbed, minutes of time where the user was physically active, instances per hour where the user physically stood up, distance data such as walking or running distance, cycling distance, swimming distance, the like or a combination thereof. In some examples, workout data such as, but not limited to, workout type, workout duration, workout distance, workout calories burned, GPS data (including, for example, latitude and longitude), swimming strokes, style of swimming stroke (such as butterfly or freeform), number of laps, length of pool, workout route, workout events (such as pause and resume), can also be used.

Figure 3A:
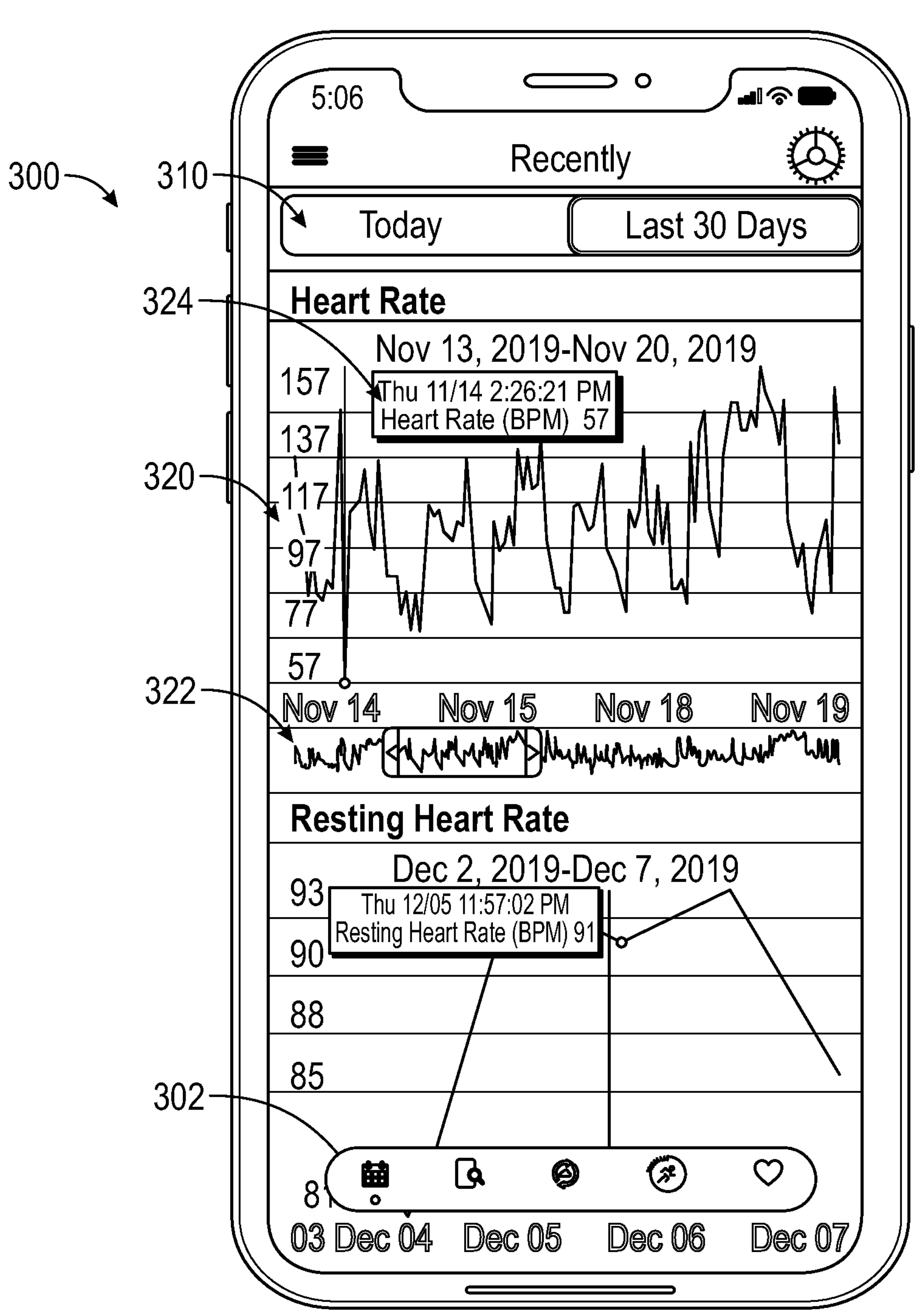
FIGS. 3A-3D illustrate example aspects of a user facing graphical user interface associated with the display of aggregated data that may be displayed on a mobile device.

FIG. 3A illustrates an example graphical display of recent biometric data. The graphical display can include one or more filter selections 310, such as a time filter. In the illustrated example, the filter includes a simplified selection of data from the current day (such as the past 24 hours) or the last 30 days. However, other values or selections are possible. A graphical display can include one or more graphs 320 associated with a biometric parameter or other user parameter. For example, a graph can include a line graph of heart rate values or other relevant user parameters that meet the selected filter parameter, such as the selected period of time. In some examples, a graphical interface can additionally include an illustration of where the displayed data fits within a larger portion of collected data that is not displayed, such as a smaller graph 322 highlighting the data currently displayed in context of data not currently displayed in detail. In some examples, a textual display 324 may pop up or otherwise display as a result of a user interaction with the graphical display 320. For example, if a user clicks on or hovers over a part of the data in the display 320, the system may show the textual display 324 overlaying the graph. The textual display 324 may include information associated with the parameter being displayed in the graph 320, such as specific date and time a parameter was recorded and value of the parameter. Additionally or alternatively, other related values may be displayed on the same interface screen. For example, a resting heart rate, instant heart rate, and heart rate variability may be displayed as a series of graphs on a single interface screen.

As illustrated in FIG. 3A, a graphical user interface 300 can include one or more control functions 302 associated with the aggregation and visualization of collected user data or the interface 300. For example, control functions 300 may include interactable portions of the display that facilitate user access to calendar functions, search functions, upload or sync functions, analysis or visualization functions, settings functions, the like or a combination thereof.

Figure 3B:
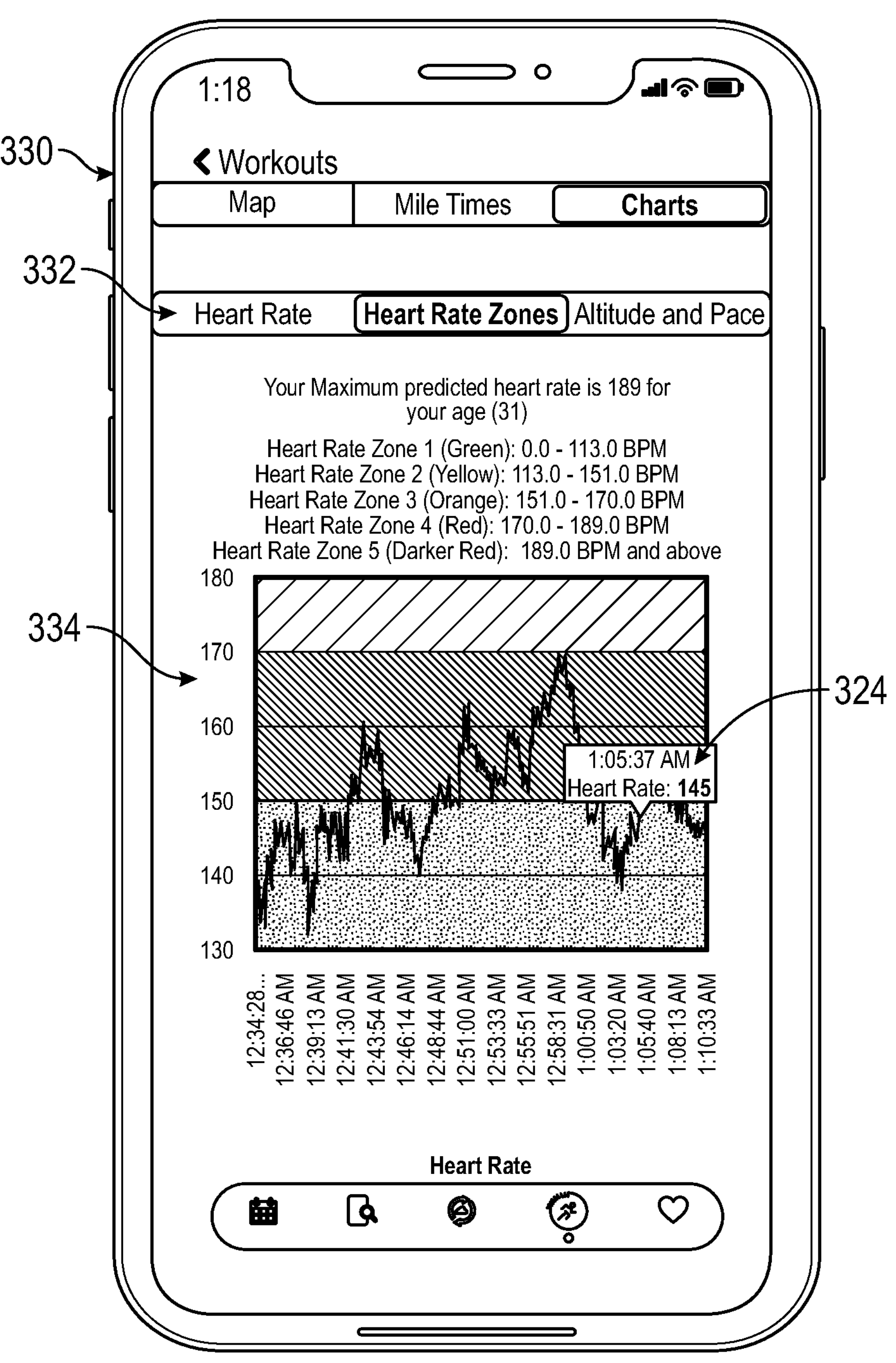

FIG. 3B illustrates an example workout screen 330 of a graphical user interface that may be part of a graphical user interface 300. The workout interface screen 330 can include one or more options to display workout data based on workout type, in reference to biometric data, or in reference to other user data. In the illustrated example, a workout may be displayed in one or more chart forms 334. For example, one or more charts can map a tracked user data during a recorded workout, such as a heart rate, hear rate zones, altitude and pace, the like or a combination thereof. In the illustrated example, heart rate in reference to heart rate zones may be graphically displayed in a chart 334. In some examples, a textual display 324 may pop up or otherwise display as a result of a user interaction with the graphical display 334. For example, if a user clicks on or hovers over a part of the data in the chart 334, the system may show the textual display 324 overlaying the graph. The textual display 324 may include information associated with the parameter being displayed in the chart 334, such as specific date and time a parameter was recorded and value of the parameter. In some examples, heart rate zones may be calculated by the application or backend system or imported by the application or backend system based on a user's predicted heart rate for their age and/or fitness level. In other examples, a workout may be displayed in other forms relevant to the type of workout. For example, a running workout may display a map illustrating GPS location of the user during their run, a tabular display of mile times, the like or a combination thereof. While workout data is described with reference to the workout interface screen 330, it will be appreciated by one or ordinary skill in the art based on the disclosure herein that other types of workouts and workout data may be displayed according to a manner appropriate to the workout type. For example, a swim workout may correlate with a display of lap times as opposed to mile times or GPS data in addition to heart rate data, such as is illustrated with respect to a running workout.

Figure 3C:
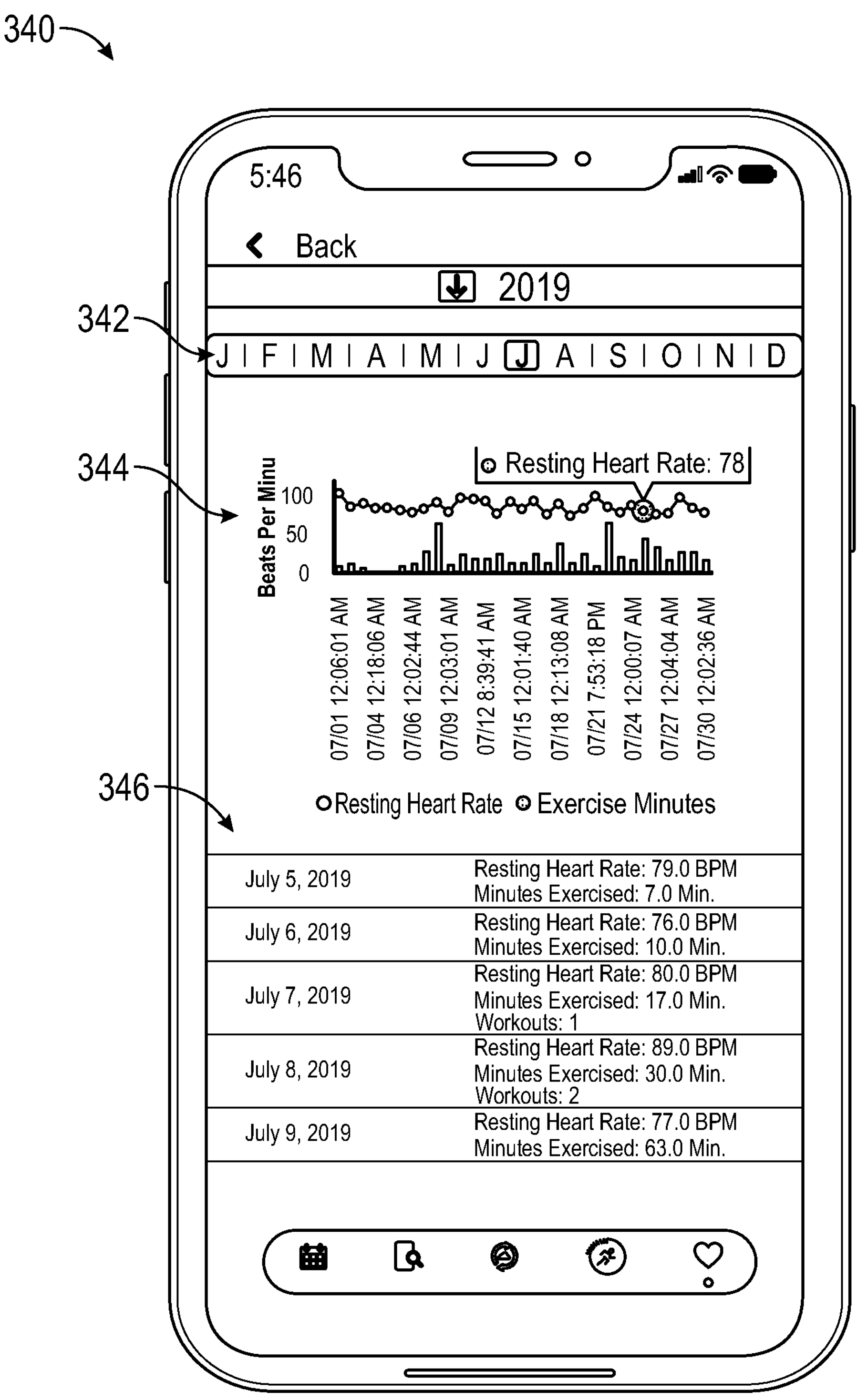

FIG. 3C illustrates an example search display screen 340 of an example graphical user interface. A search display screen 340 may display data graphically (such as in a graph 344 similar to the one or more graphs described above with reference to FIGS. 3A and 3B) and/or tabularly (such as in a table 346) that is searched for by the user that fits a set of search parameters. In some examples, search parameters, such as month, date, or year can be graphically displayed 342 to enable a user to quickly and easily navigate their data. For example, the search display screen 340 may receive input relating to searching for data between two or more dates, by certain events, by data source, other parameter relating to collected data, or a combination thereof.

Figure 3D:
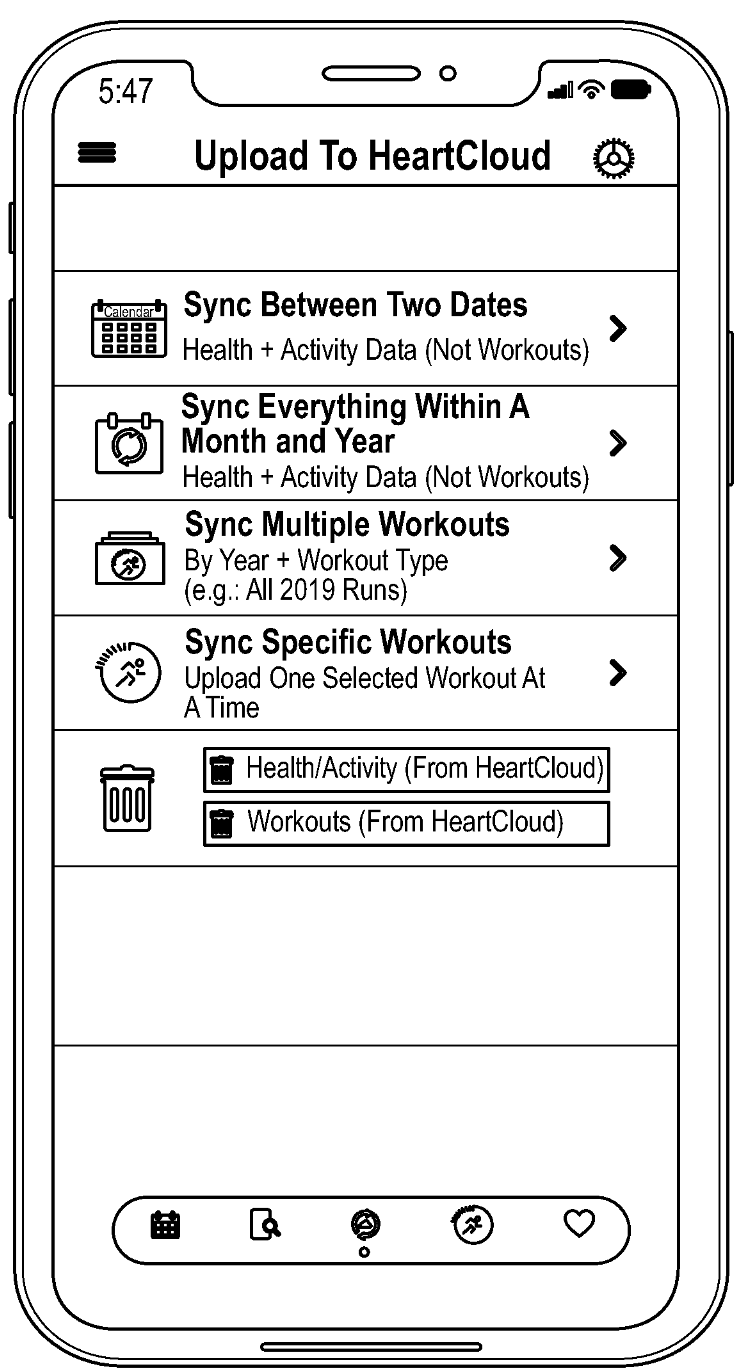

FIG. 3D illustrates an example upload screen 350 of an example graphical user interface. The upload screen 350 can include one or more options to upload, access, edit, delete, or otherwise interact with aggregated user data. For example, an upload screen 350 can include one or more options to sync data between one or more points in time (such as between a first calendar data and a second calendar date or during a designated date, month, or year). In some examples, an upload screen 350 can include one or more options to sync data by type, such as workouts by type during a period of type. In some examples, an upload screen 350 can include one or more options to sync parameters one at a time or by manual selection. In some examples, an upload screen 350 can include one or more options to link or unlink a connected data collection device from the application. In some examples, an upload screen 350 can include one or more options to delete, move, or edit uploaded data.

FIGS. 4A-4M illustrate example aspects of a user facing graphical user interface associated with a system that may be displayed on a user device with a larger screen than a mobile device, such as a desktop device.

FIG. 4A illustrates an example graphical user interface that a user may be able to access through, for example, a web portal. In the illustrated example, a graphical user interface 400 can include one or more panels for displaying and accessing functionalities of the system. For example, an interface 400 can include a control panel 410 and a display panel 412. In some examples, the interface 400 can include one or more interactive portions 414 configured to facilitate a user's access to account information, search functions, other functionalities, the like or a combination thereof. In some examples, an interface 400 can include a quick display portion 416 configured to display recent or aggregated data associated with the user, such as a time of latest upload, data related to mile times, data related to heart zones, data related to heart recovery, the like or a combination thereof.

Figure 4B:
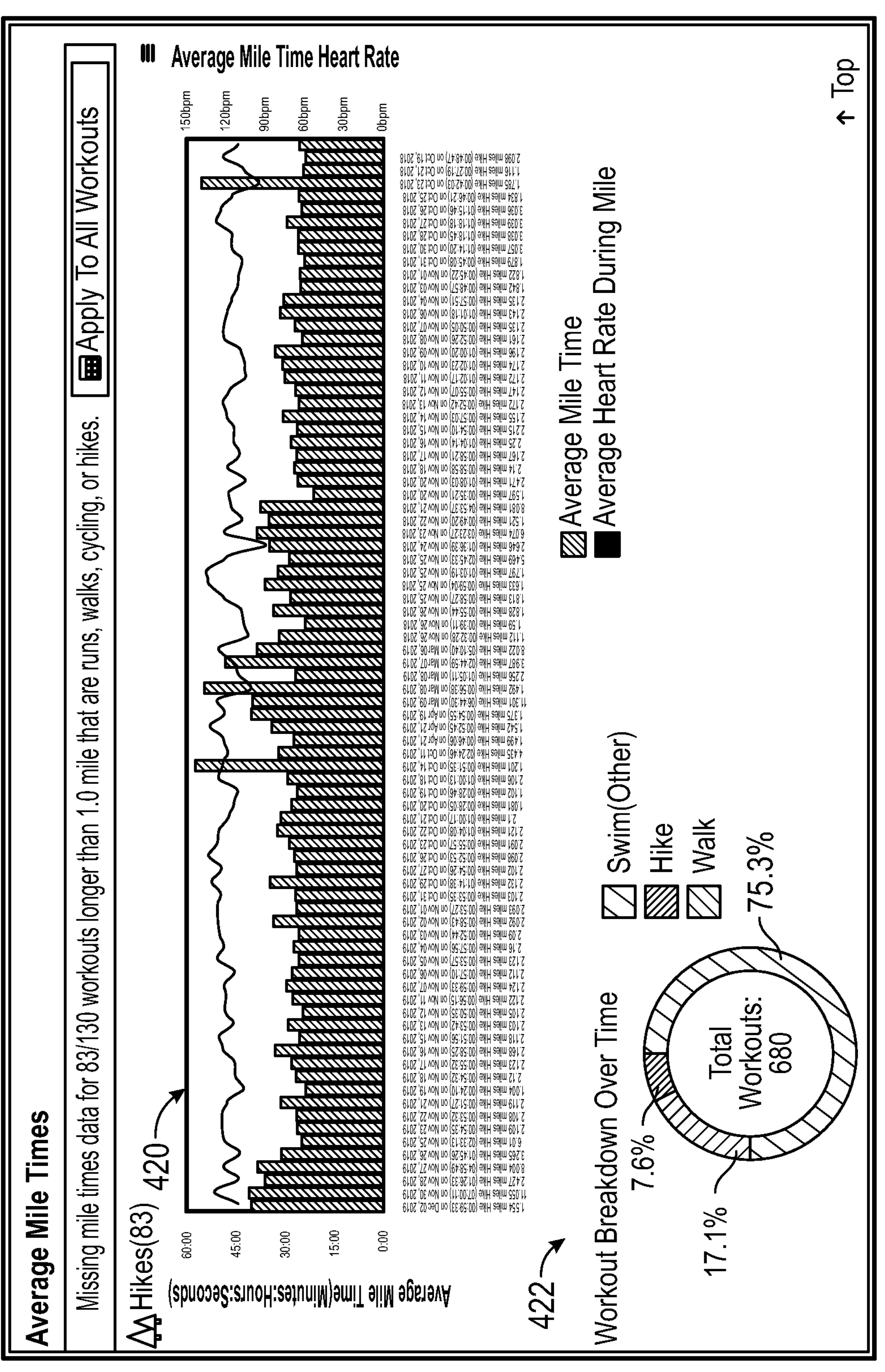

FIG. 4B illustrates an example aspect of a data visualization that may be part of a graphical user interface related to collected user data. For example, workout data relating to a type of workout may be displayed in relation to a relevant workout parameter and biometric parameter over time. For example, the illustrated graph 420 illustrates data relating to an average mile time and average rate during the mile over the course of time for the total number of hikes recorded. In another example, the system may display aggregated workout data to show workout by type or other filter parameter. In the illustrated example, a pie chart 422 illustrates a percentage of types of workout per the total.

Figure 4D:
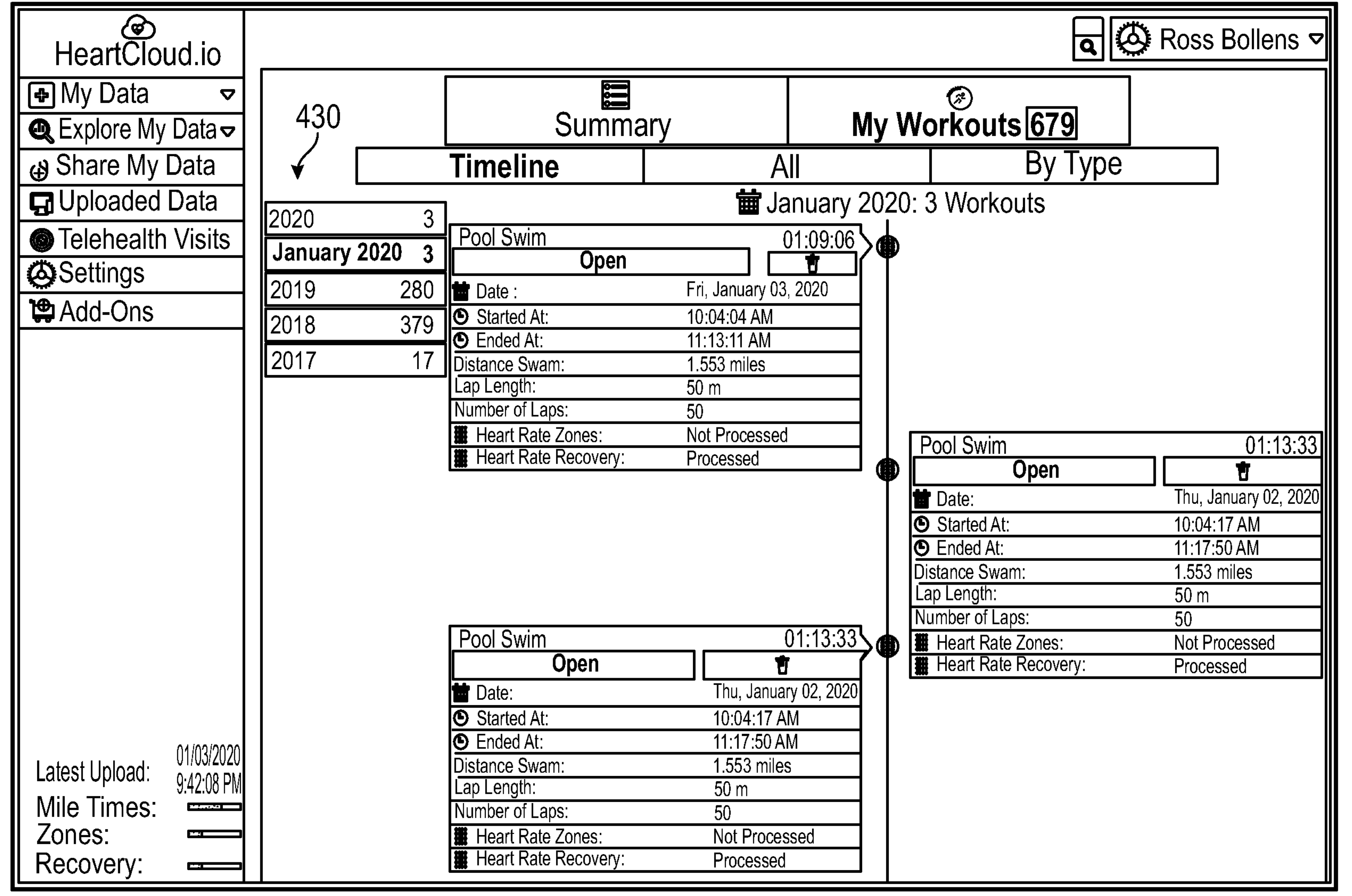

FIGS. 4C and 4D illustrate further example aspects of visualization of collected workout data. For example, as illustrated in FIG. 4C, workout data may be organized to show a tabular illustration of workouts and relevant parameters associated with those workouts. For example, an interface 400 can include options 424 to select a summary form of workouts (such as illustrated in FIG. 4B) or a list form of workouts. However, other options for display may also be possible. In some examples, an interface enables a user to display to tabular form in different ways. For example an interface 400 can include one or more selections 426 for view types, such as timeline view, full list view, or grouped view. FIG. 4D illustrates an example timeline view 430 associated with a set of workout events occurring during a selected period of time. A full list view may show a table of workout events. A grouped view may show a table of workout events grouped by workout type or other categorization. The one or more view types can include information associated with workouts, such as date recorded, start and end time of workout, distance, number of laps, lap length, heart rate zones, heart rate recovery, GPS information, mile times, the like or a combination thereof.

Figure 4E:
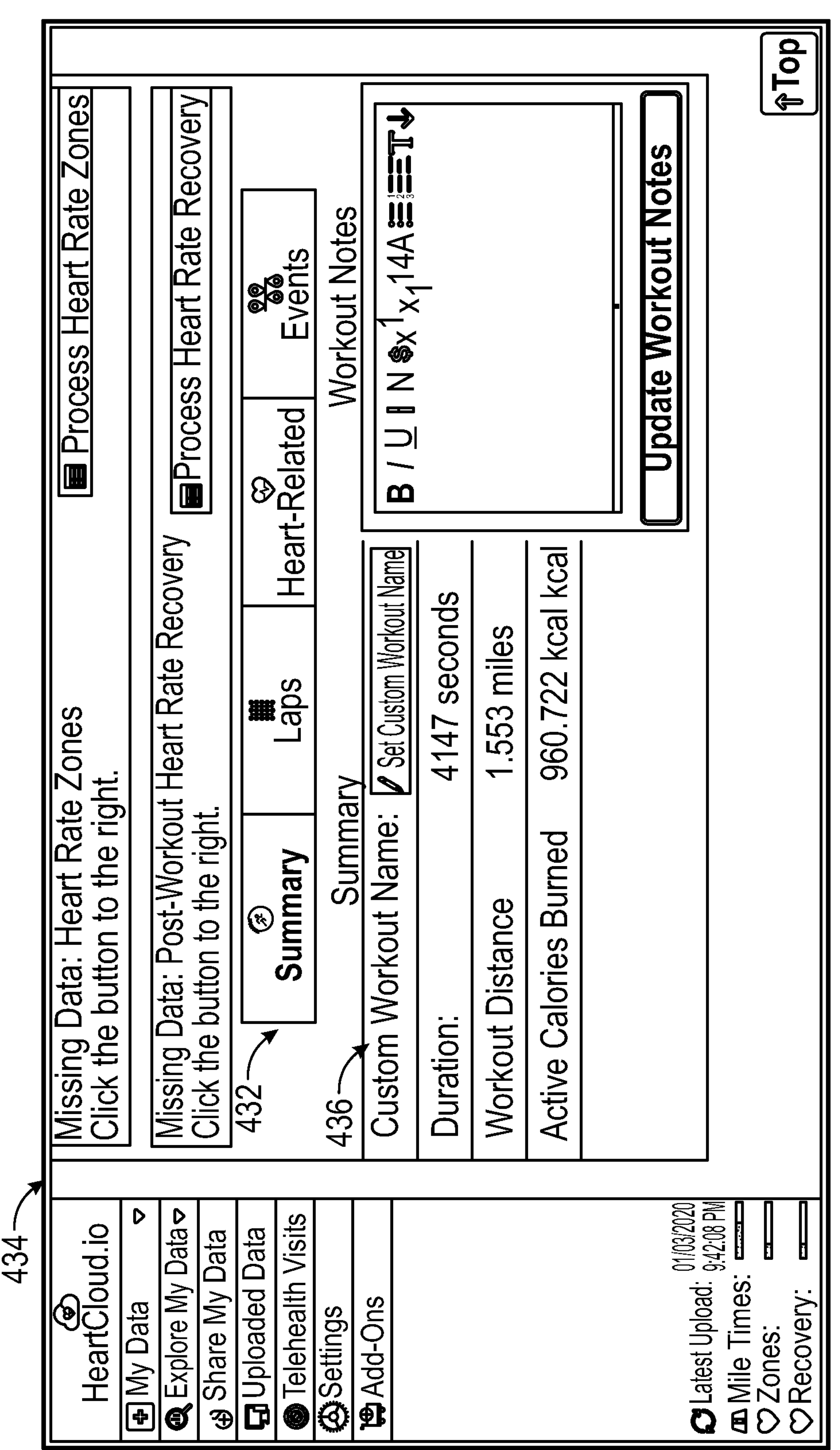

FIGS. 4E-4M illustrates example aspects of an interface 400 associated with visualizing a single workout. For example, as illustrated in FIG. 4E, an interface 400 can include one or more interactive selections 432 for accessing data associated with a workout. For example, a selection 432 can include a summary, a review of workout specific parameter types (such as lap information), heart related data, workout related events (such as start and stop times, pause times, or other events). Once a user selects a selection 432, the system may display information associated with the selection in a display portion 436. In some examples, the display portion 436 may have one or more portions configured to enable a user to edit or input data associated with the selection. This input can include information not collected by one or more data collection devices, such as a workout name or workout notes. In some examples, an interface can include one or more prompts 434 to edit, upload, or input data that the system has identified as missing. For example, the system may identify that heart rate data is missing and prompt the user to process, upload, or input heart rate data. In some examples, an interface may additionally include an overview summary of the workout in one or more areas of the interface (such as overview 450 illustrated in FIG. 4I).

Figure 4F:
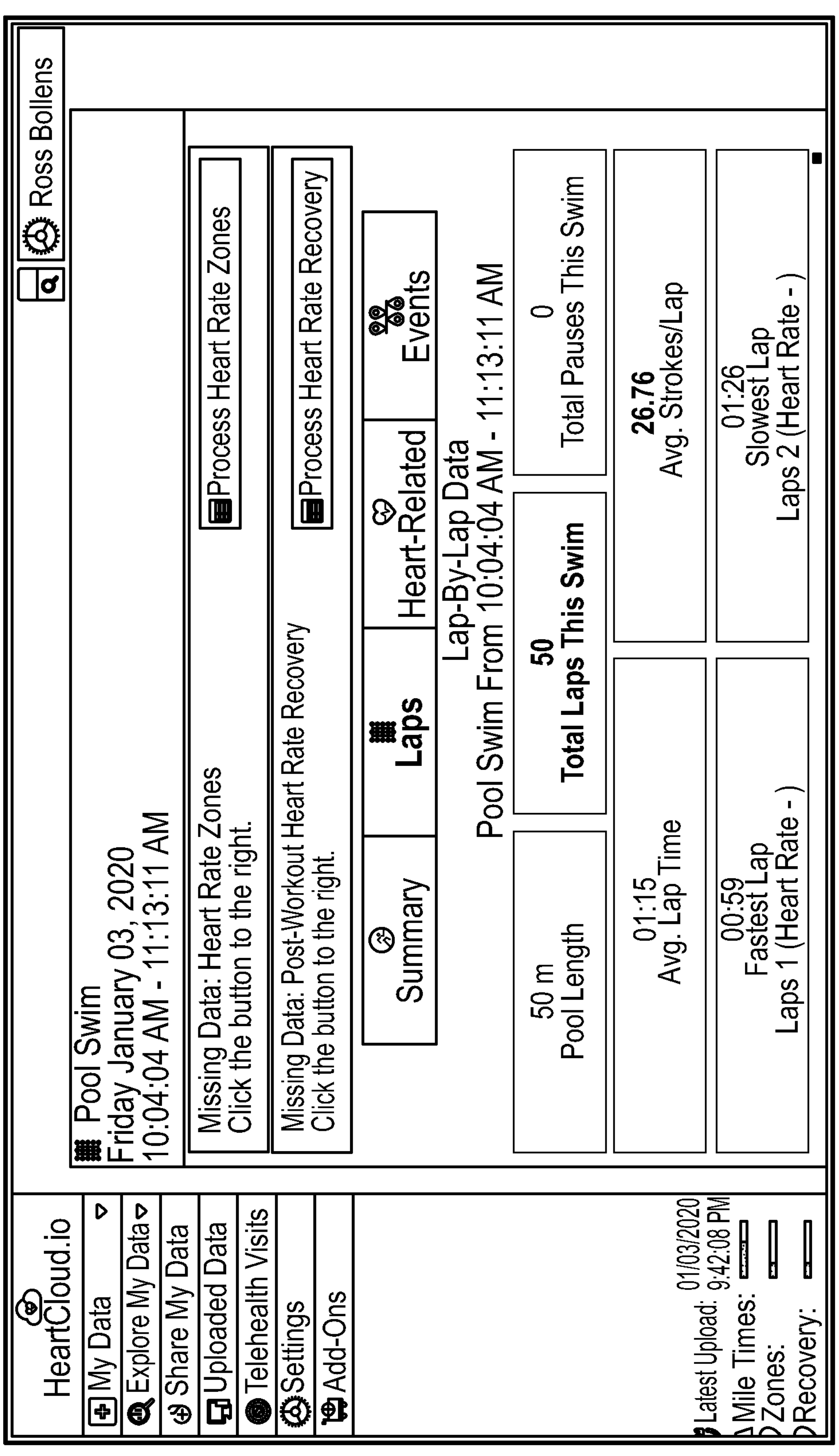
Figure 4G:
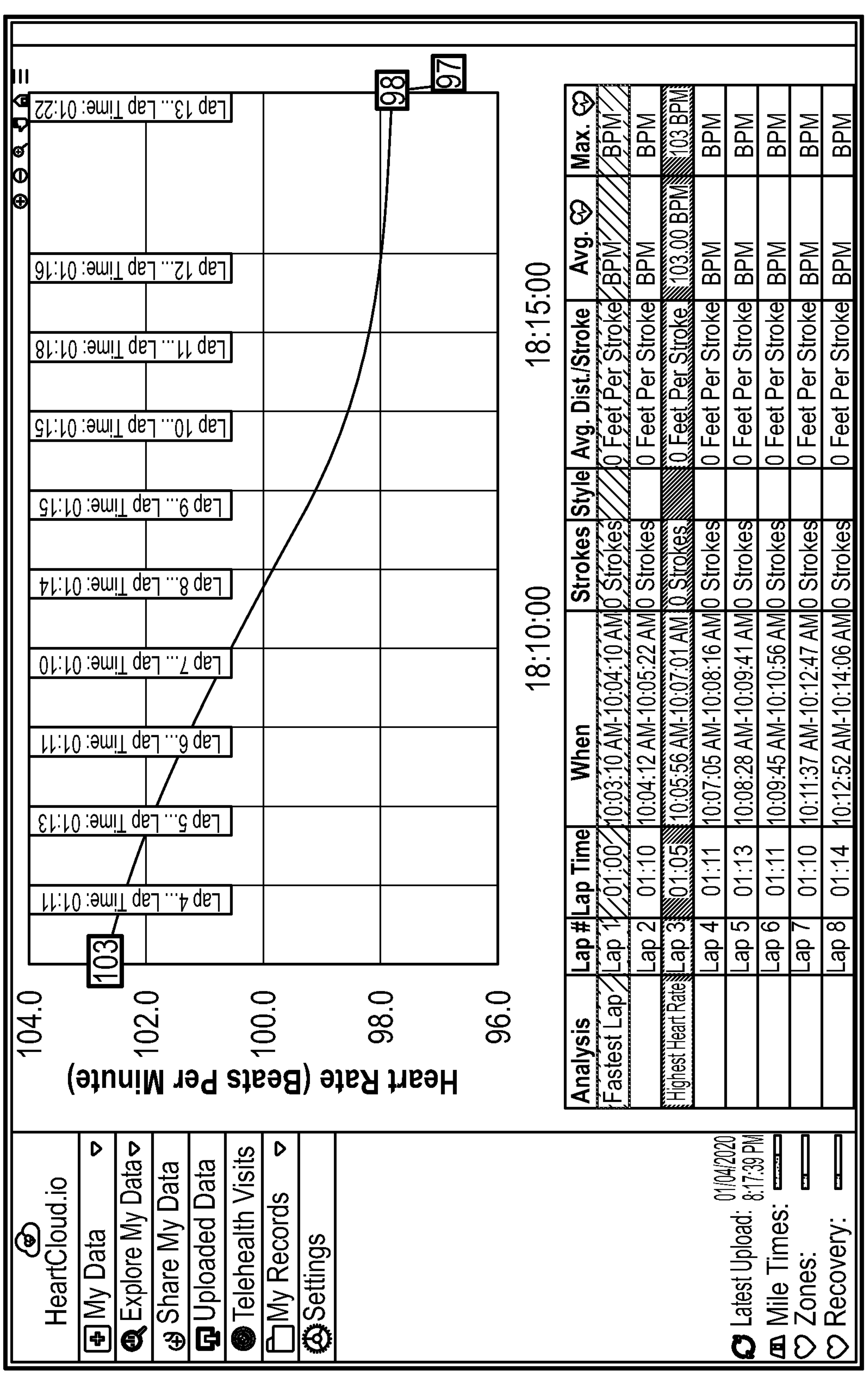
Figure 4H:
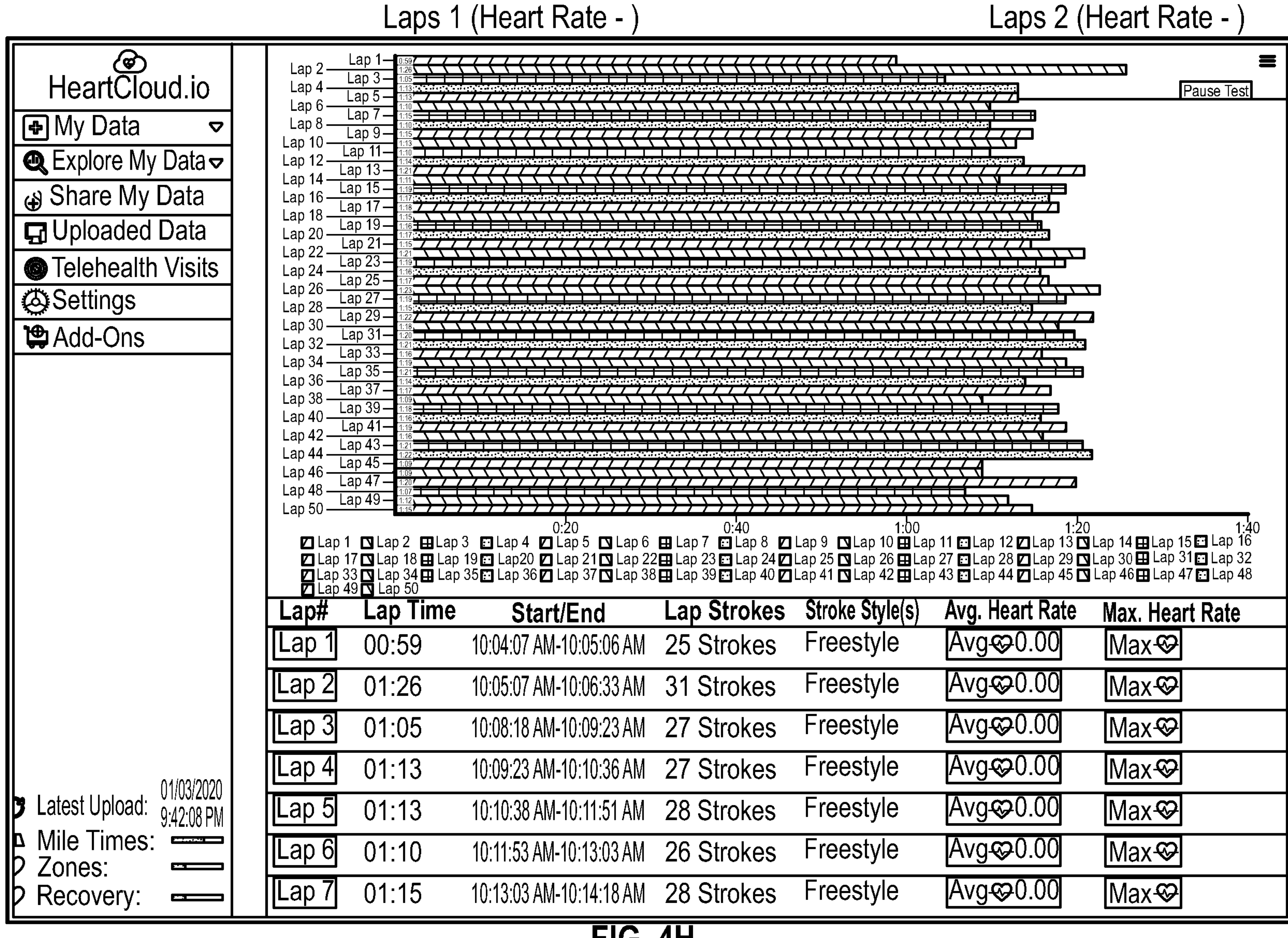

FIGS. 4F-4L illustrate example aspects of an interface 400 related to visualization of a swim workout. As illustrated in FIG. 4F, a selection of lap by lap visualization may cause the system to display information relating to swim laps, such as pool length, total laps during the selected swim workout, total pauses during the selected swim workout, average lap time, average stroke and lap time, fastest lap time, slowest lap time, the like, or a combination thereof. As illustrated in FIG. 4G, laps may additionally or alternatively be visualized in a graph and/or tabular form by, for example, graphic lap times and heart rate in a single graph or tabularly displaying lap times and other workout data, such as heart rate. In some examples, the system may highlight different events, such as highest heart rate or fastest lap time in the chart or graph for ease of use for the user in analyzing their data. FIG. 4H illustrates an additional visualization option related to a swim type workout illustrating a bar graph of lap times over the course of a workout and/or a tabular display of lap and heart rate data. However, while certain visualizations and/or combinations of data are illustrated, other visualizations and combinations are possible.

Figure 4I:
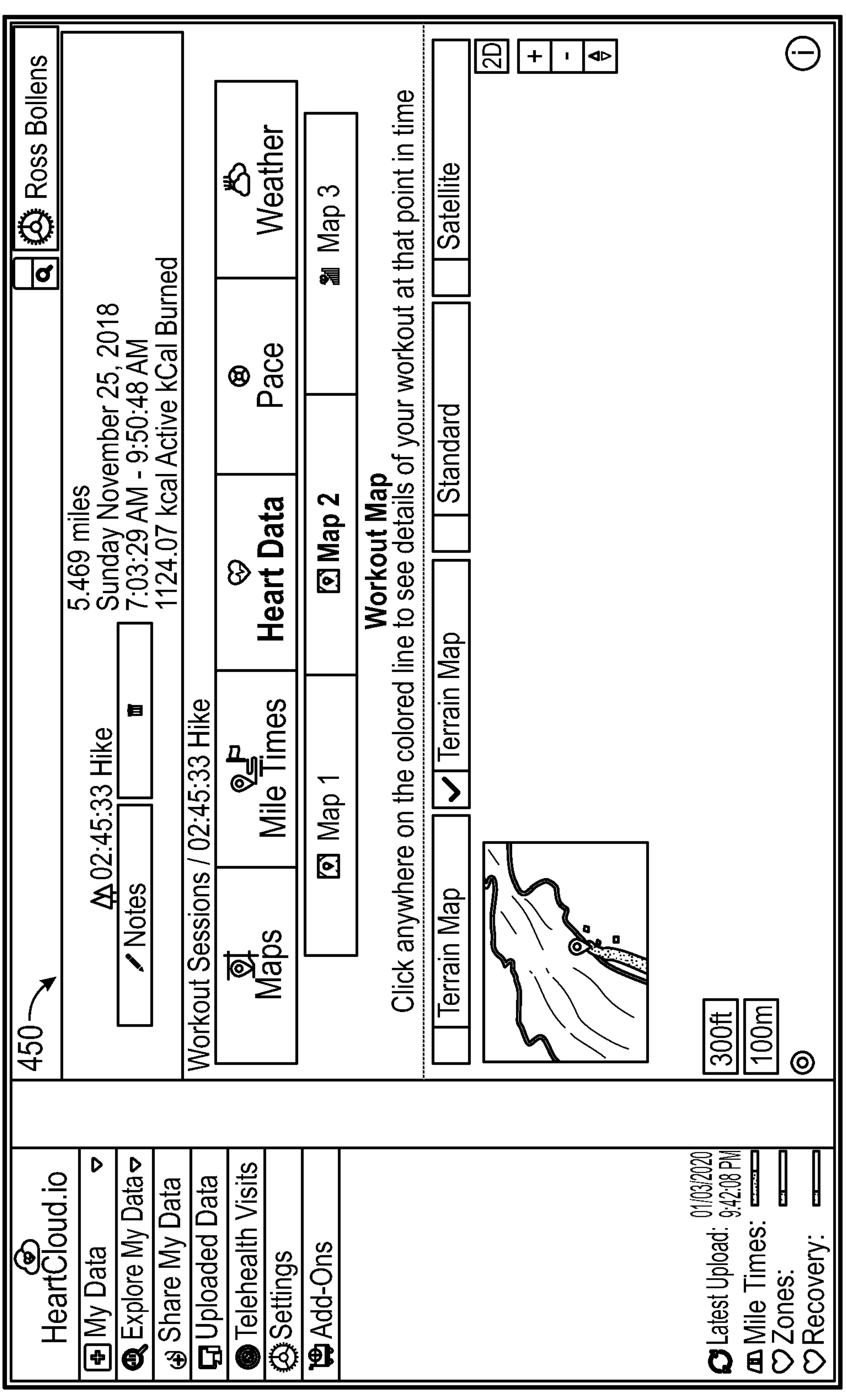
Figure 4L:
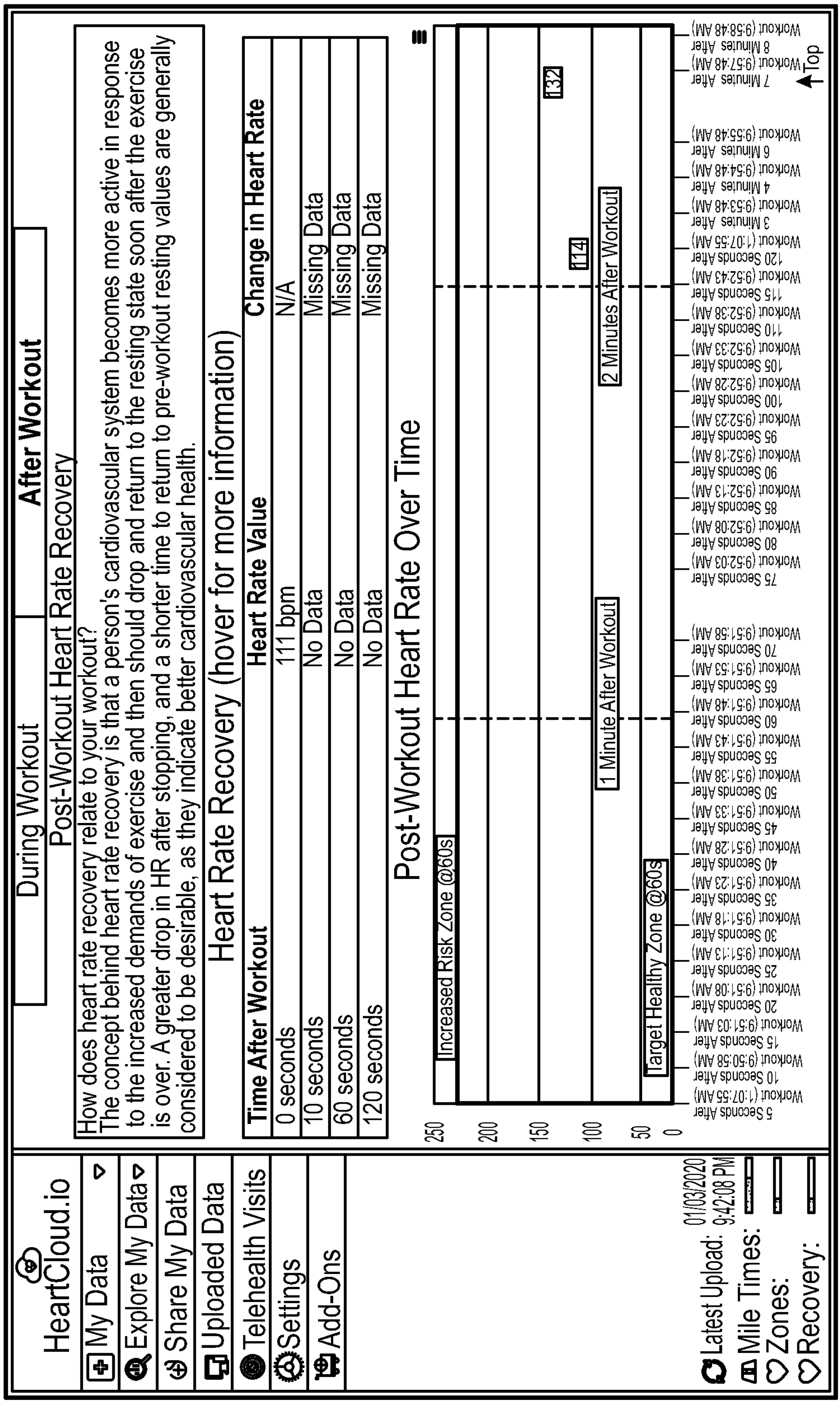

FIGS. 4I-4L illustrate example aspects of an interface 400 related to visualization of a hiking workout. As illustrated in FIG. 4I, a hiking workout may be visualized using GPS and/or terrain data. For example, a user selection of a map type visualization may cause the system to display one or more maps of the user's hike or outdoor workout based on acquired GPS data. The visualization can include one or more terrain maps, standard street maps, and/or satellite maps. FIG. 4J illustrates an example visualization of a hiking workout that may be displayed by the system upon a user selection of a mile based visualization. For example, as illustrated in FIG. 4J, a system may display graphically and/or tabularly parameters associated with each mile (or other interval) of the workout. In some examples, a graphical display can include a bar graph of mile times. In some examples, a tabular display may include rows of mile data, such as starts, stops, pauses, altitude, heartrate during a mile, the like or a combination thereof. FIG. 4K illustrates an example visualization of heart data associated a hiking workout. For example, a user may select a time range during which to visualize heart rate data, such as during or after a workout. The system may accordingly display heart rate data, such as highest, minimum, and average heart during the selected time range. Additionally or alternatively, the system may display a chart or graph of time spent in identified heart rate zones. The heart rate zones may be calculated based on user data or acquired from another source, such as a data collection device. FIG. 4L illustrates an example visualization related to heart rate recovery after a workout, such as a hiking workout. For example, the system may display heart rate recovery data. In some examples, the heart rate recovery data may be displayed tabularly and/or graphically based on time after a workout, a heart rate value, and/or a change in heart rate value.

Figure 4M:
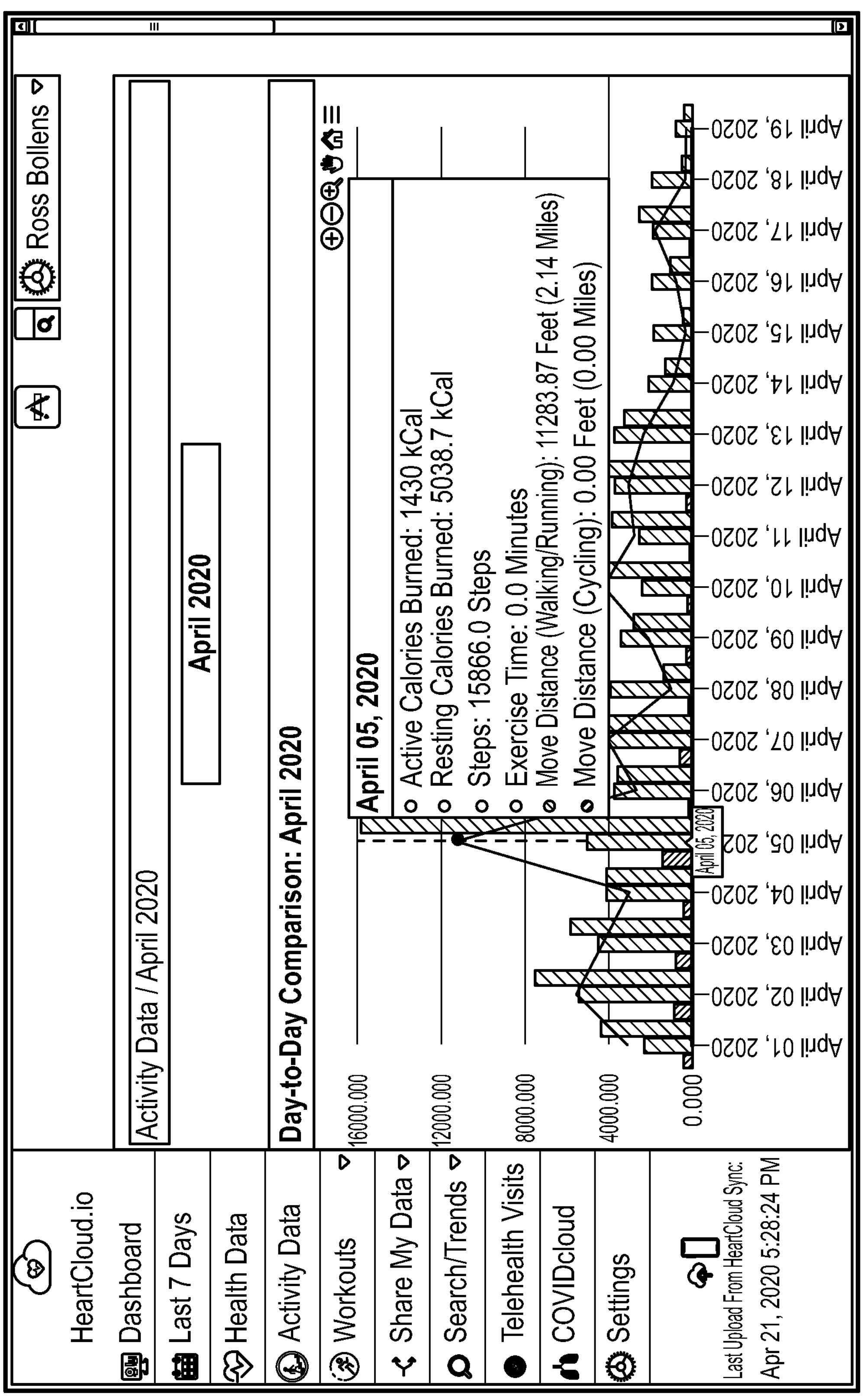

FIG. 4M illustrates an example comparison visualization aspect of an interface 400. For example, a system may display collected data, such as active calories burned, resting calories burned, steps, exercise time, move distance (such as during walking, running, or cycling), the like or a combination thereof. One or more data types may be displayed in a graph within a selected time frame, such as a month. In the illustrated example, multiple data types over the course of a month are displayed in a graph. The graph may be configured to display each data type in a different color or shading so as to enable a user to quickly perceive differences among data values while viewing a plurality of data types. In some examples, different data types may be displayed differently. For example, a move distance may be displayed as a line or line graph, which a number of steps may be illustrated as a bar or bar graph.

Figure 5A:
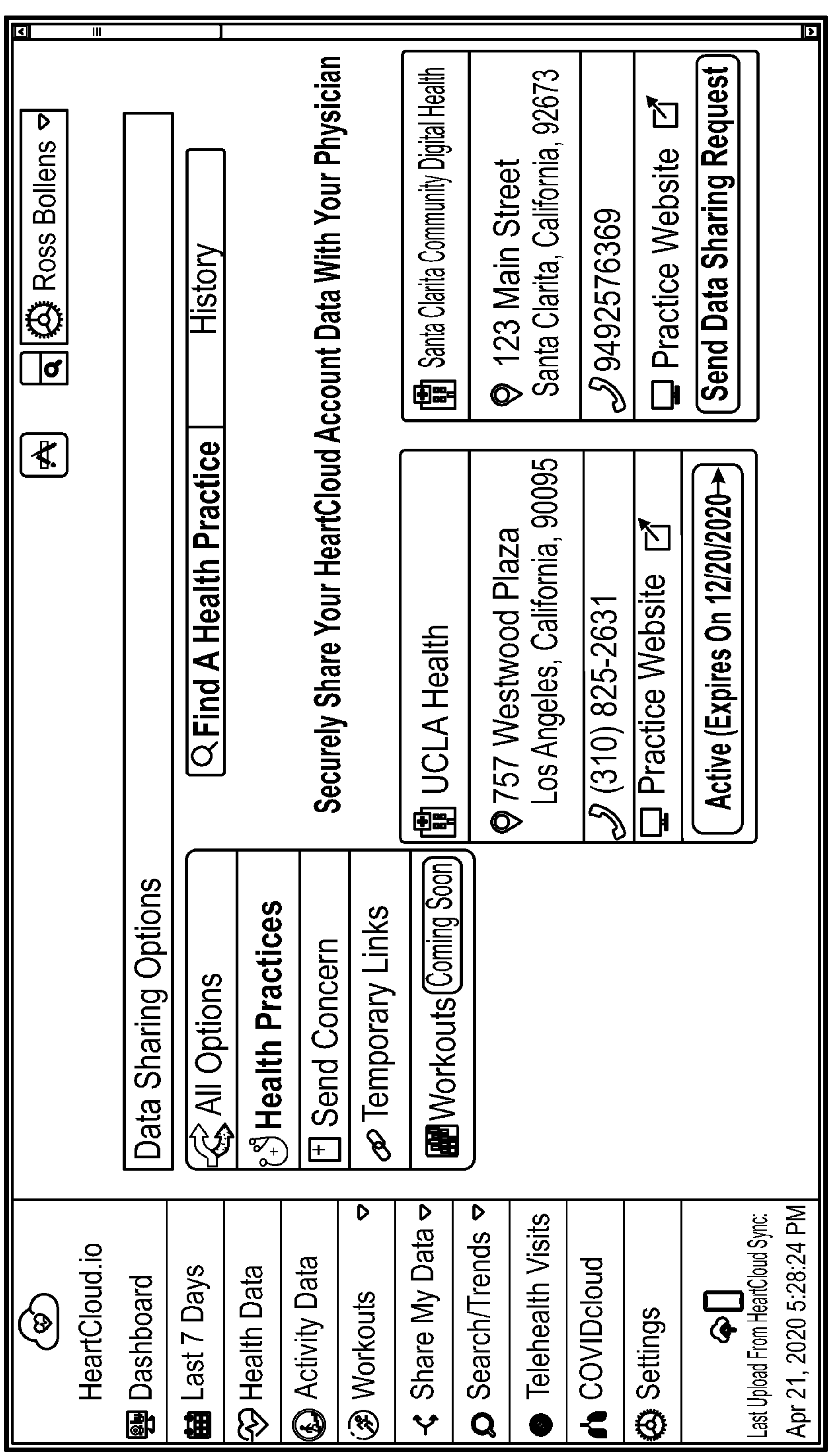
Figure 5B:
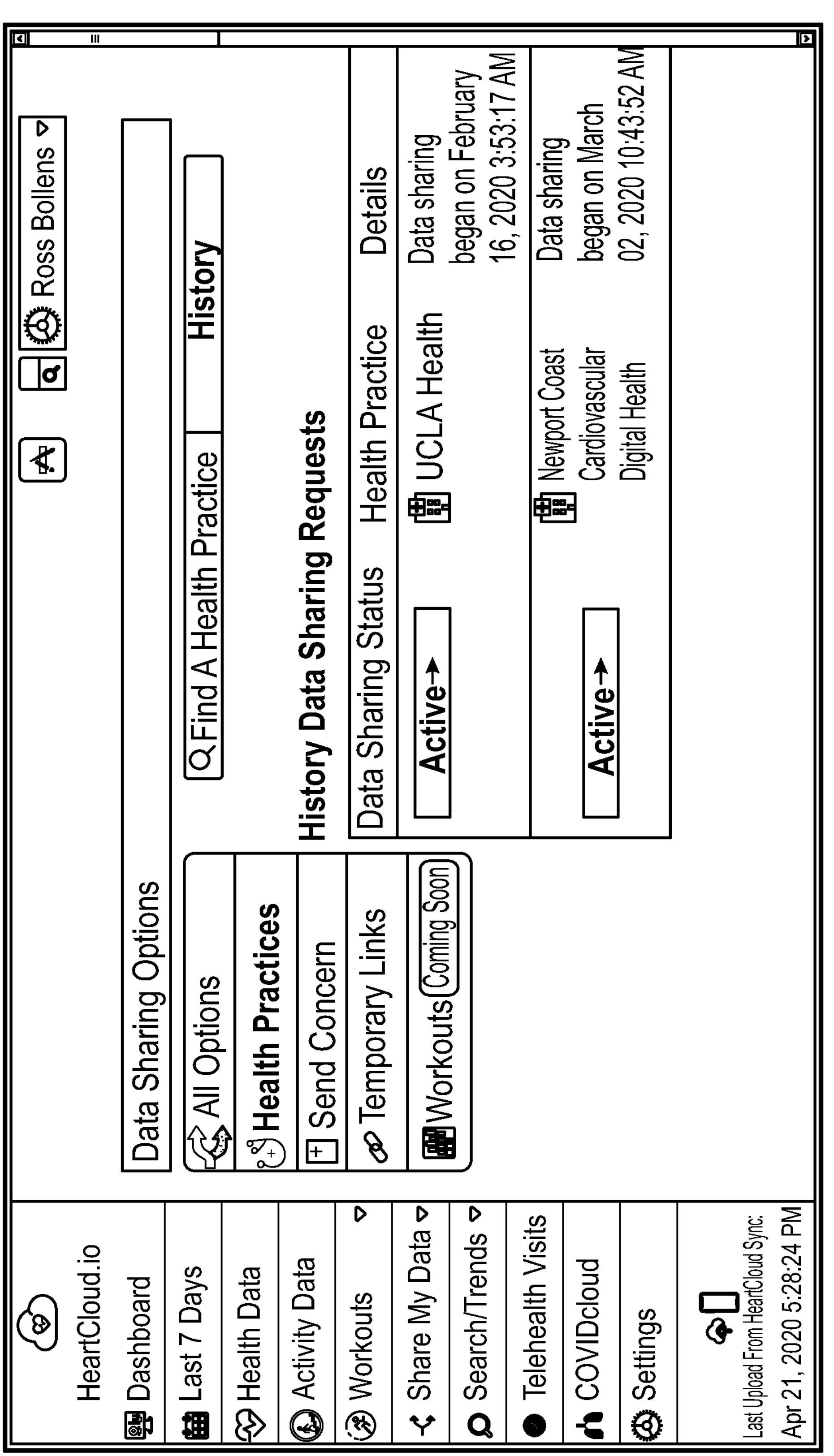

FIG. 5A-5B illustrates an example telehealth aspect of an interface 400. For example, as illustrated in FIG. 5A, a system may provide one or more options for sharing data, sending messages, or otherwise interacting with a healthcare provider. In some examples, a system may provide a search functionality in order to allow a user to find a preferred healthcare provider or allow a user to find the best health care provider based upon the measured data in the system. In some examples, the system may enable the user to send data to the healthcare provider in anticipation of a telehealth visit. For example, a system may provide authorization to one or more data types during a period of time that may coincide with the telehealth visit. In some examples, the system may facilitate the telehealth visit by connecting a user to the healthcare provider through audiovisual communication. In some examples, as illustrated in FIG. 5B the system may enable the user to view a history (past, active, and/or future) of data shares, telehealth visits, or other healthcare provider related information. The healthcare provider may also granted access to the collected data and may also have data manipulation capabilities as described in this application.

Figure 5C:
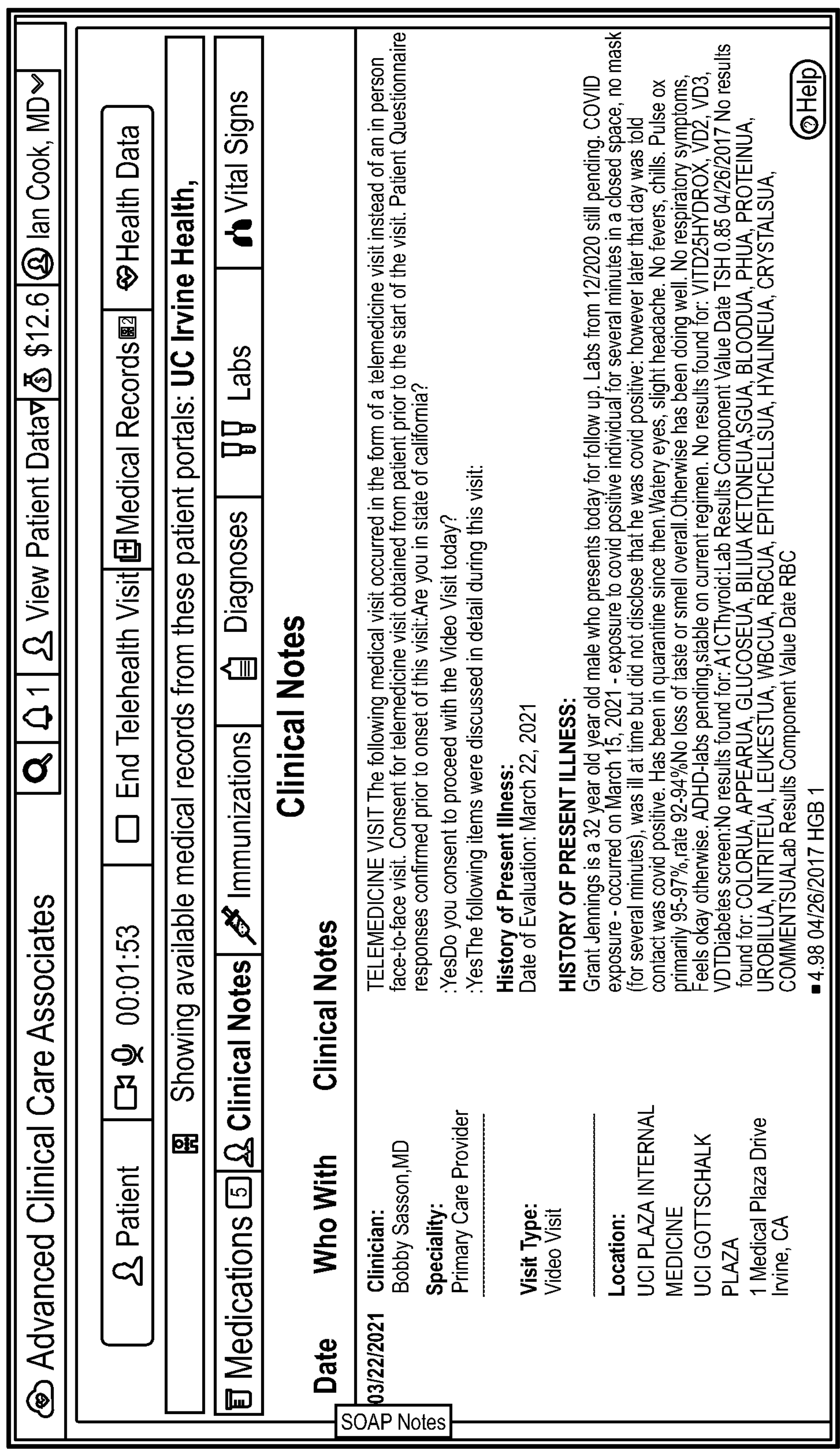

FIG. 5C illustrates an example aspect of an interface 400 that may be displayed to a healthcare provider user during a telehealth session. For example, the interface 400 may include a plurality of tabs or other interactive components configured to facilitate access by a clinician or other user to information associated with a patient. In some examples, the interface may include one or more tabs, such as a patient information tab, medical record tab, telehealth related tab(s), health data tab, medications tab, clinical notes tab, immunizations tab, diagnoses tab, labs, and vital signs tab. The patient information tab may display patient information associated with current patient in a telehealth session.

FIGS. 5C and 5D illustrates an example medical records tab display that may be part of the interface. As illustrated, a medical record may display a source of the medical record, such as a care provider or hospital. The medical records may be organized according to sub categories, such as medications, clinical notes, immunizations, diagnoses, labs, and vital signs. A medical records tab may display one or more aspects of a patient's medical record. Advantageously, the medical record information may be from varied sources or the same source. The medical record information may be formatted for consistency across data sources and case of readability. FIG. 5C illustrates an example aspect of an interface with a clinical notes tab of a medical records tab selected. The clinical notes may be organized by date, clinician associated with the note, and/or the content of the note itself. FIG. 5D illustrates an example aspect of an interface with a lab tab of a medical records tab selected. The lab results may be display or organized automatically or by physician preference. Categories for organization or display may include, but are not limited to, date, health system (or source of data), test, result, and/or reference range.

Figure 5E:
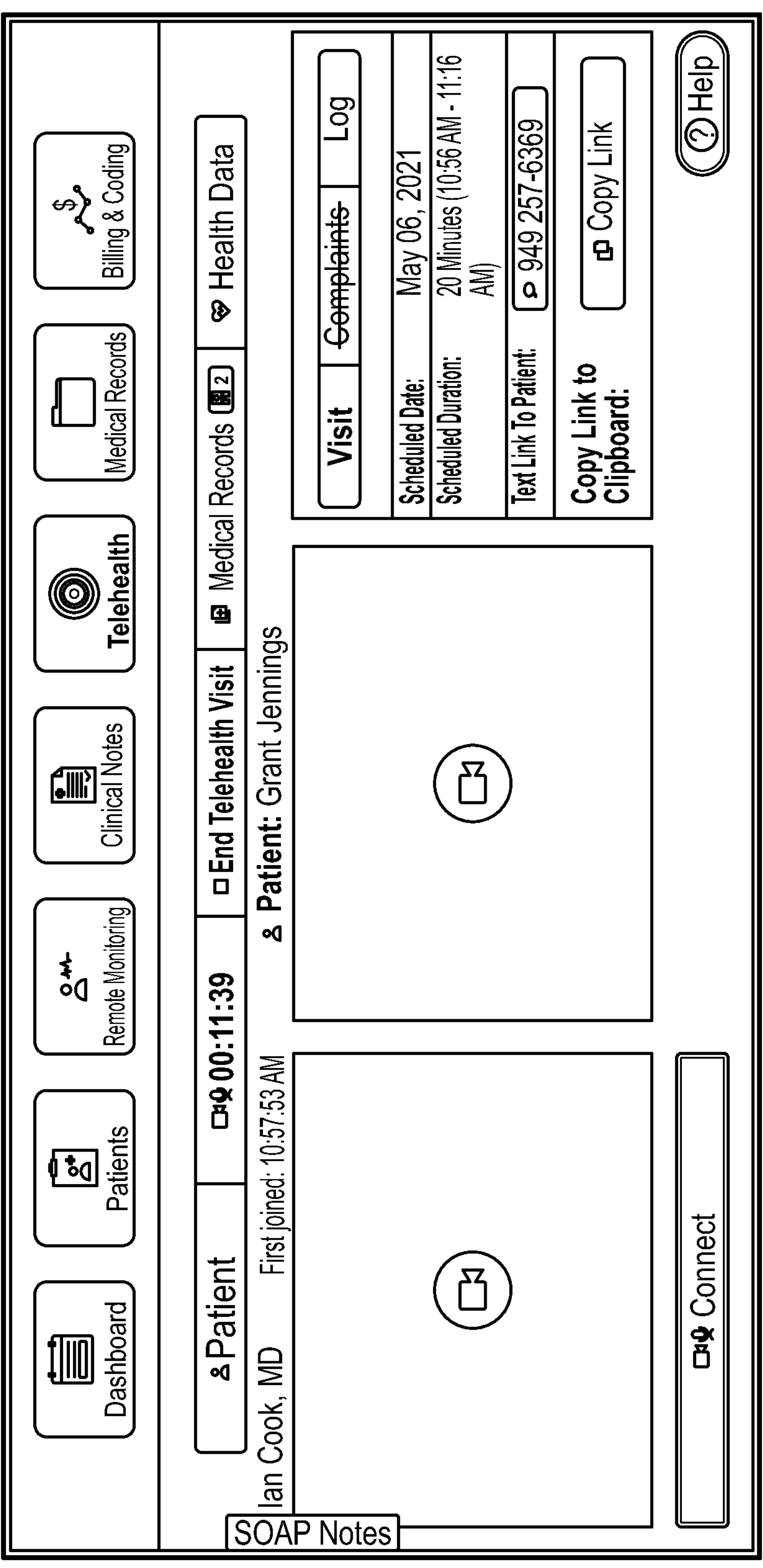

FIG. 5E illustrates an example aspect of an interface 400 that may be displayed to a healthcare provider user during a telehealth visit. Some or all of the tabs or interactive components of a telehealth aspect of the interface may be accessible during a telehealth session, which may or may not include an audiovisual connection. Other aspects of data collected and configured for display can be shown in a user dashboard or interface that includes audiovisual information associated with a telehealth session. The audiovisual information may include video and/or audio information for connected parties in the telehealth session, such as a clinician and a patient. In some examples, the interface may include an interactive component to start or connect to a patient or session, a timer to record the start time of the session, and/or an end telehealth visit interactive component. The end telehealth visit may cause the system to do one or more of: trigger an end to the audiovisual connection, record data associated with the telehealth visit, prompt a user (such as the clinician) to record notes or other information associated with the visit, and/or present other data associated with the interface, patient, or telehealth visit. In some examples, a telehealth dashboard may include one or more interactive components to view visit information, complaint information, and log information relating to the telehealth session. In some examples, the dashboard may include a link for sharing an audiovisual connection or information.

Figures 2, 5F:
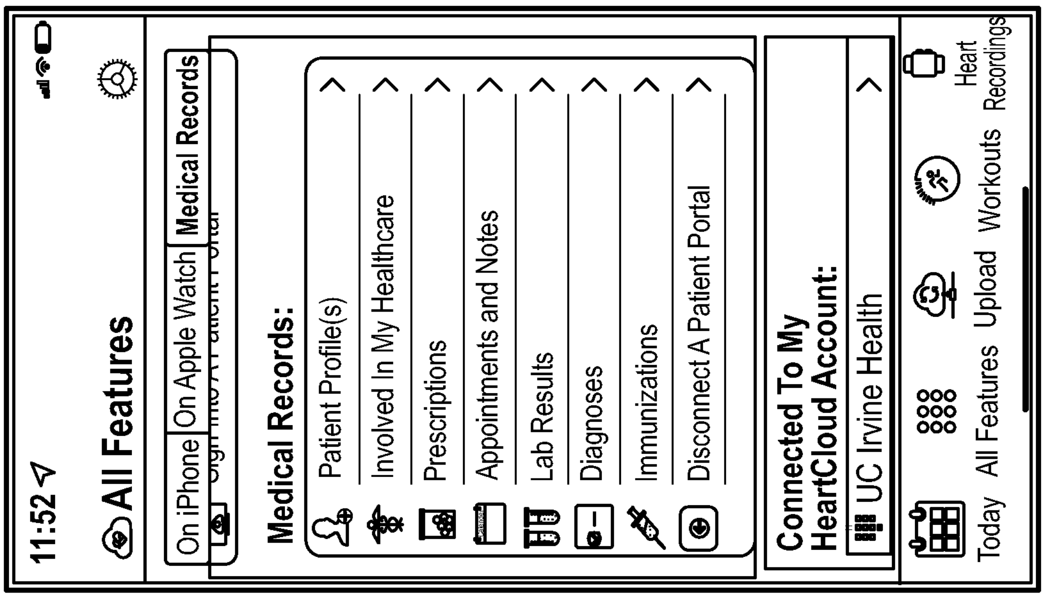
Figures 1, 5F:
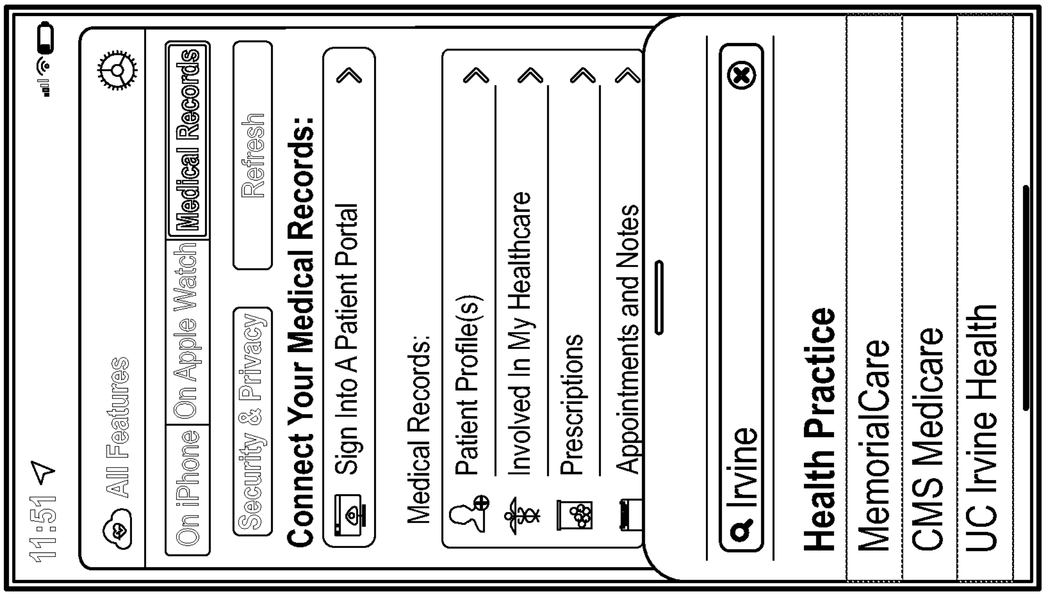

FIGS. 5F-1 and 5F-2 illustrates an example aspect of an interface 400 that may be displayed to a healthcare provider user on a mobile device. For example, in the illustrated example, a patient or clinician may access medical record data. The medical record data may be retrieved from one or more health practices or sources. As shown in FIG. 5F-1, a user may search for health practices by name or other identifier (such as location). This information may then be accessible from the interface, such as illustrated in FIG. 5F-2 . . .

Figure 5G:
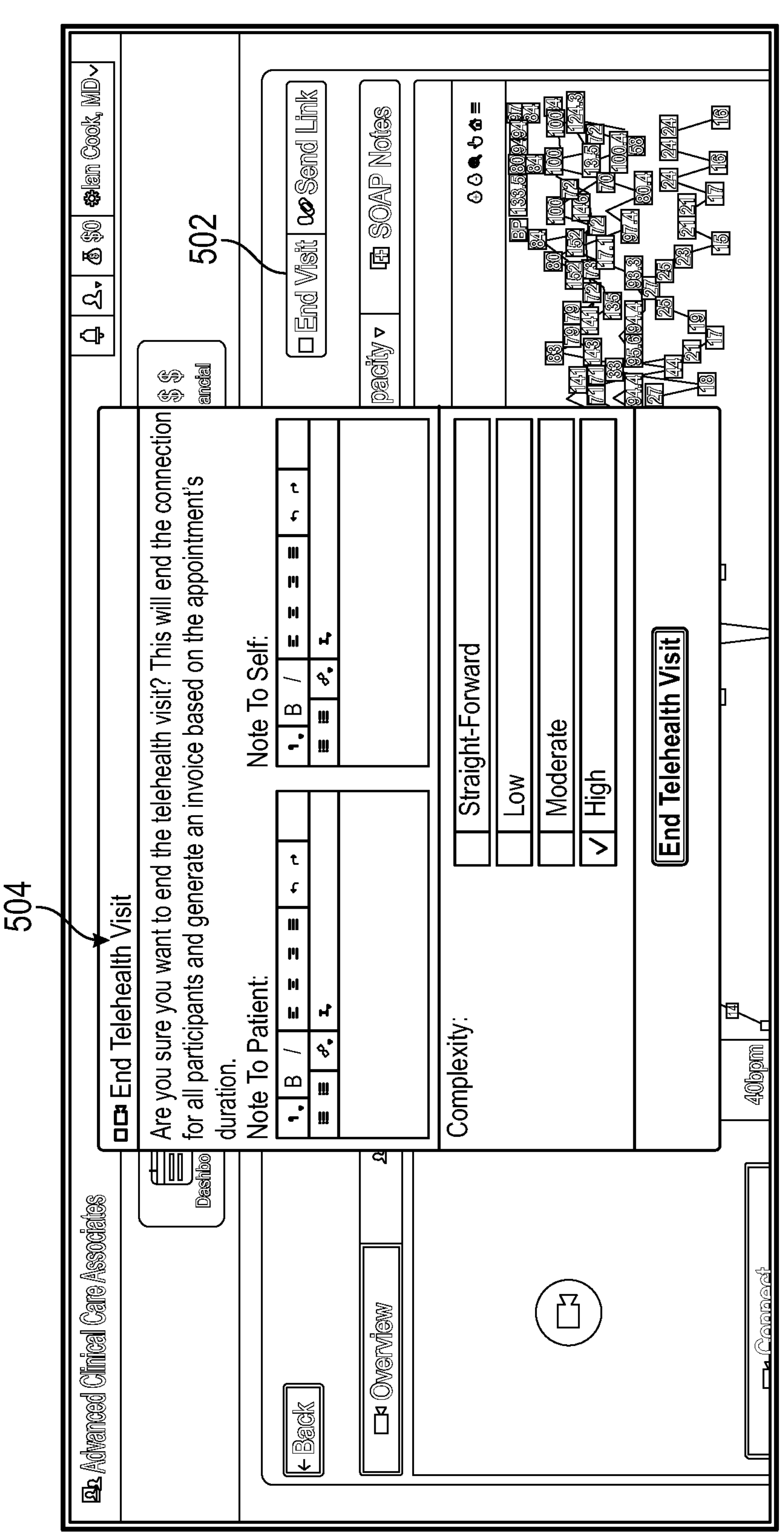

FIG. 5G illustrates an example aspect of an interface 400 that may be displayed to a healthcare provider user. For example, the interface 400 may include one or more interactive components, such as an "End Telehealth Visit" button 502. Clicking or tapping on the end telehealth button may present a window overlay 504. The window overlay 504 may present one or more input options to enable a patient or healthcare provider to input information associated with the telehealth visit. For example, the input options may include, but are not limited to text based notes for the patient, for the healthcare provider, for another user, administrative review, other reviewer, the like or some combination thereof.

In some examples, input options may include a rating associated with the telehealth visit, such as a rating associated with a complexity of the visit. For example, the interface may include a menu of selectable items associated with the complexity of the visit to enable the healthcare provider to identify if a patient interaction was straightforward, low, moderate, or high. In some examples, the patient complexity or other rating may be used for billing purposes or medical record keeping. For some medical services, the level of payment can be attached either to the amount of time on the clock for providing the service, or it may be keyed to the "Complexity of Medical Decision Making" (MDM); longer procedures and more complexity leads to higher payment. By providing the clinician with an easy way to specific MDM complexity at the time of the visit's ending, this ensures that the staff will assign the correct billing code to the visit, instead of relying on memory as to complexity or duration. The example interface may additionally or alternatively include a timer associated with the telehealth call. The time may display how long the telehealth call has been happening. This information may be passed directly into the records associated with this telehealth visit, which is desirable in the event that the records are audited.

FIG. 5H illustrates an example of another aspect of an interface 400 that may be part of a telehealth or other functionality. An interface may include a healthcare provider or clinician interface. The healthcare provider or clinician interface may include information associated with the healthcare provider's patients or clients. For example, a docket of healthcare provider patients or clients may be accessed and displayed to a healthcare provider user. The docket may include information associated with the patients or clients, such as one or more medical record numbers, patient status, age, sex, last known visit, details about a telehealth or other patient interaction (such as visit duration or visit type), healthcare provider notes, the like or a combination thereof. Advantageously, a patient status or patient relationship may be highlighted or displayed with different colors or badges so that a healthcare provider can organize their information easily. In some examples, an interface may include a dashboard page with the information organized in accordance with clinical workflows. A clinical workflow can, for example, be presented in a context that supports existing or anticipated approaches to clinician observations or method of work.

FIG. 5I illustrates another example aspect of an interface 400 that may be part of a telehealth or other functionality. The interface 400 may include information associated with different healthcare providers or clinicians. In some examples, the information may be accessible by a patient user. In some examples, the information may include a name, title, contact information, other profile information, required license for practice, the like or a combination thereof. In some examples, the information may be viewed or edited by a healthcare provider user. In some examples, the information may be sourced from an internal profile for each health care provider account. In some examples, the profile information may be used for billing purposes. This information may be accessed, for example, by a user through a profile interface. The profile may include some combination of data such as name, contact information, and related data.

FIG. 5J illustrates another example aspect of an interface 400 that may be part of a telehealth or other functionality. An interface 400 may include information associated with a telehealth visit. For example, an interface may include times when one or more participants connected or disconnected from a telehealth visit, the duration of the telehealth appointment in minutes and seconds, the identity of the participants, the date of the telehealth visit, information accessed during a telehealth visit, the connection status of video, audio, or other connectivity, the like or a combination thereof. Advantageously, this information may enable a reviewer or system to evaluate the criteria necessary for properly selecting the correct procedure code applicable to the factors of the telehealth visit. In the illustrated example, if the described telehealth visit with the physician displayed above is the first telehealth visit with the clinician, the system would select CPT code 97802 to satisfy the criteria shown in Table 1 because the data indicates a 6 minute 46 second duration of connectivity between a licensed physician and a new or established patient using a synchronous connection that included both audio and video capabilities. In some examples, this information may be accessed through a summary tab or portion of the interface.

FIG. 5K illustrates an example aspect of an interface 400 that may be associated with access of medical records. An interface may provide a connection to medical records or medical providers for display and access of information by users, including patients and healthcare providers. In some examples, accounts associated with healthcare providers may be connected so as to download, view, upload, edit, or otherwise access information associated with records of the connected healthcare provider. In some examples, the medical records may be displayed separately or together with other collected workout or health information, such as heart rate, blood pressure, the like or a combination thereof. Medical records may be displayed for patients, physicians, or other users. The system may include capabilities concerning medical records stored in electronic health records systems. The records from other practices may be displayed as text or formatted for consistency. The records may be marked as to their source in some examples.

Figure 6A:
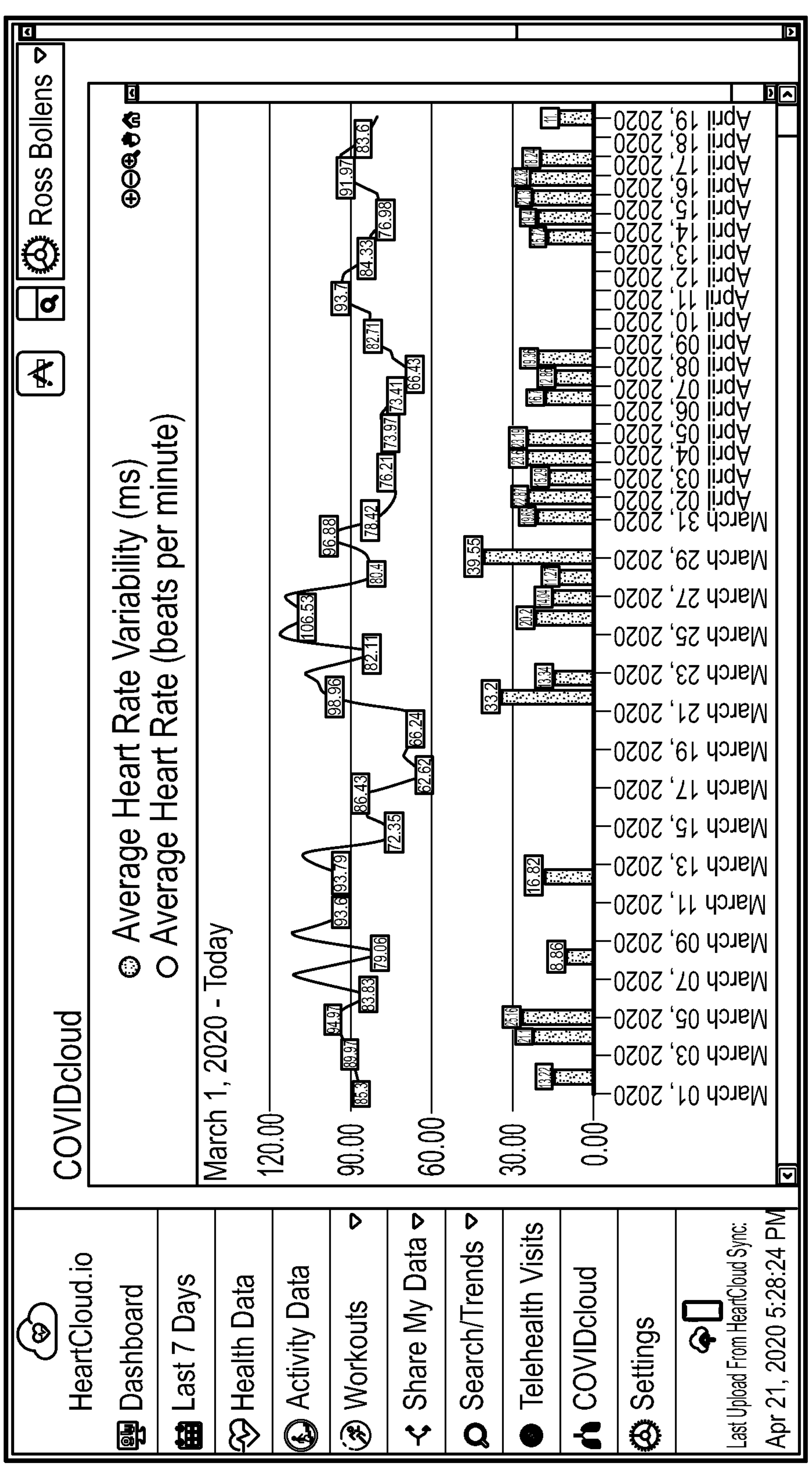
FIGS. 6A-6B illustrate example infectious disease monitoring aspects of an interface.

FIG. 6A illustrates example infectious disease monitoring aspects of an interface 400. For example, the system may graphically display one or more biometric parameters related to infectious disease monitoring, such as temperature and heart rate. In the illustrated example, a user's heart rate is plotted as well as a user's average heart rate variability. In other examples, a user's body temperature may be plotted. In some examples, different parameters may be plotted based on, for example, the type of infectious disease being monitored and/or based on physician input.

Figure 6B:
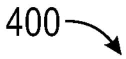
Figure 6B:
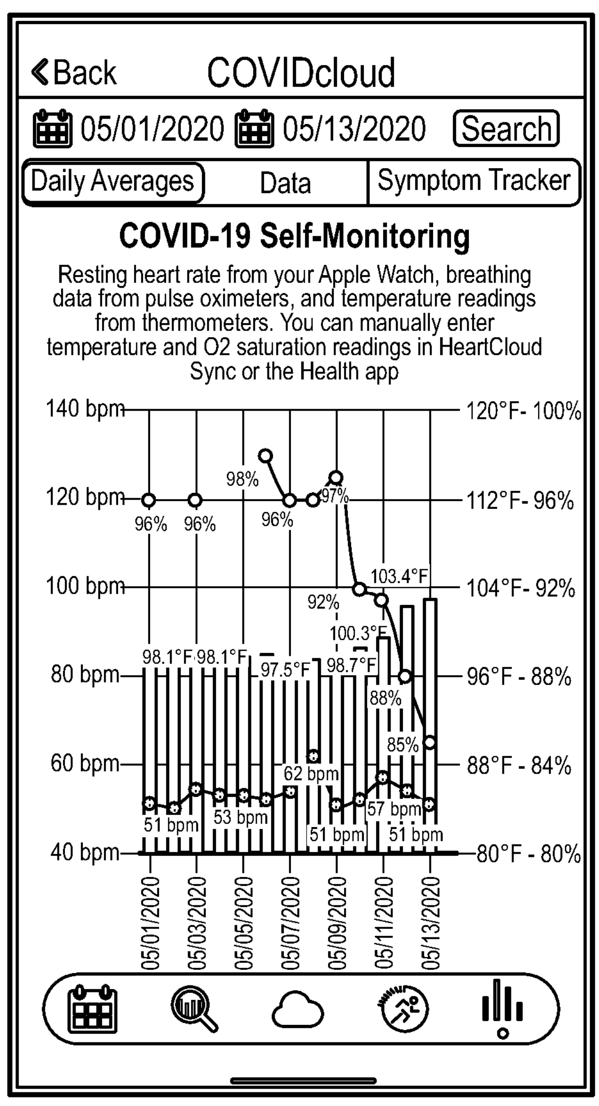

FIG. 6B illustrates another example aspect of an interface 400 as represented on an example mobile device screen. In the illustrated example, one or more of the user's biometric parameters can be displayed for visual inspection and monitoring by the user. In some examples, data relating to the presence and severity of symptoms of infection or other disorder may be displayed, allowing the user to self-monitor the progress of a potential or actual infectious disease or disorder. In some examples, user data may be displayed to show parameter progression over time, such as day by day, hour by hour, month by month, or other time progression.

For example, as illustrated in FIG. 6B, a user's temperature, heart rate, breathing data, or other parameter associated with monitoring of a disorder may be displayed in a combination plot. Advantageously, a combination plot showing over time comparisons and progression may allow a user to easily note changes in their health over the time period shown or selected as indicated by the displayed parameters.

Additionally or alternatively, in some examples, the data may be displayed tabularly. Additionally, a user may not have data supported by the system for each day. For example, a user may have forgotten to charge a pulse oximeter for 48 hours and therefore data from such a device would not have been recorded on a day when other data from other devices supported by the system was. The system may be able to compensate for this potentially common occurrence by rendering gaps in charts or in tabular form where data of one type is unavailable, but all or some others are. This is a significant advantage over traditional data retrieval and/or display systems because a physician making a medical decision based on a visualization of a patient's data stored or otherwise made available by the system may thus be able to clearly perceive periods of time where data is missing. In some examples, the system may select or suggest parameters to track for a particular disorder or disease according to a predetermined rule, a healthcare provider recommendation, or automated method of choosing a set of parameters, such as a machine learning algorithm. Additionally or alternatively, a user may select parameters record, track, monitor, and/or display. In some examples, a user may track symptoms, such as headache, nausea, dietary distress, sleep quantity or quality, mood, appetite, or other value. The tracked symptoms may additionally or alternatively be displayed with other biometric parameters on a combination plot, facilitating comparison of more qualitative metrics as well as quantitative metrics of disorder progression.

In some examples, the infectious disease monitoring functionality can be applied to tracking user movement in order to help track spread of disease by infected individuals. For example, data corresponding to disease monitoring data can be linked to building access systems which would allow individual's access to areas based on whether the individual is deemed healthy or within certain allowable health data measurements. In some embodiments, an individual who eventually displays problematic health data measurements (e.g., a sick individual) can also trigger the system to deliver notifications to other users that they have been in contact with (using GPS data). In some embodiments, the other users can then also forward notifications to their other contacts that they have been in contact with a sick individual. Advantageously, this can allow better tracking of a spreading disease. Additionally or alternatively, such disease tracking may facilitate decision making on who to allow access to a building or location or when to allow access based on current or past health conditions. Thus, safer access to shared locations, such as offices, public buildings, houses of worship, or other gathering places, may be facilitated through the systems and methods described herein.

While the visualizations described herein are described with reference to specific workouts and data parameters, a person of ordinary skill in the art will appreciate that the visualizations and aspects of the visualizations described herein may be applied to other types of collected data.

Any of the visualizations described herein may be interactive. For example, a visualization may include a graph. The system may facilitate displaying an overlay when a user interacts with a data point on the graph by, for example, hovering or clicking on the data point. A similar overlay may be available for a tabular visualization.

J. Example Data Aggregation and Storage

One or more aspects of a data communication, processing, aggregation and visualization system can be implemented by one or more hardware processors associated with a user device such as a smartphone, tablet, computer, or a thin client system. For example, one or more aspects of the data communication, processing, aggregation and visualization system can run as part of a software system on a user device. The software system can include one or more functionalities and/or may preprocess the data for display on in a graphical user interface that may be part of the software system. In some examples, the system may apply one or more filters, select data, correlate or paring data (for example, heart rate and step count data from matching periods of time) or otherwise processing the data. In some examples, a system may be designed to use minimal processing capabilities of the user device.

In another example, the system can be configured to access, retrieve, copy, or receive user data from the user device or third party system. The system may then copy or store the user data to a backend system or within local storage accessible by the system. In some examples, a user may select how data may be uploaded or stored. In some examples, a user may optionally select to upload one or more types of data. For example, a user may select health and activity data to upload or workout data to upload. In some examples, the user may filter the data to upload by, for example, selecting a time range, data type, or other parameter.

A system can prompt a user to upload a copy of their health, workout, activity data, or collected biometric data from their user device to a cloud account. The user can upload, via a user device, data based upon an arbitrary user-selected time range or upload all data. The user can, via a user device, also upload data based upon specific workout sessions. Both original, unmodified data returned from user API queries and processed data not returned by the user API queries can be uploaded to a cloud account associated with a backend system. The backend system may comprise a hosted computing environment that includes a collection of physical computing resources that may be remotely accessible and may be rapidly provisioned as needed (sometimes referred to as a "cloud" computing environment), thereby providing higher system uptime and reliability and a more flexible and dynamic allocation of computer resources. The data may be stored in a hosted storage environment that includes a collection of physical data storage devices that may be remotely accessible and may be rapidly provisioned as needed (sometimes referred to as "cloud" storage) to reduce idle resources. Section N details an example key and value pairs of a dictionary used to organize contents of an example running workout during upload and storage.

Once received by an endpoint API located at one or more user devices and uploaded to an account associated with the user, a system may be capable of generating long-term trends in user data quickly and efficiently.

Data uploaded to a backend system can be associated with a user account such that a user may have secure access to their data through a web portal and/or mobile application. The user or user device may be authenticated (e.g., via user biometrics (e.g., using facial recognition, voice recognition, fingerprint recognition, iris recognition, or the like), UserID/password, unique user device token, and/or the like) prior to being granted access to the user account and/or user data. In some examples, data may be associated with a user through a JSON web token (hereafter "JWT"). When a user signs into their account on the mobile application, the mobile application can receive a JWT from the backend system that serves as a user authentication for the user's installed instance of mobile application that may be unique to their user device. A JWT token can be stored on the user's local device and also saved to a user database based on their primary user key. That allows for a strict string literal comparison between the token stored on the user device and customer database such that the currentness of the user session can be monitored and that a mismatch could mean that the account was logged into elsewhere, which would lead to immediately closure of the session.

In some examples, a backend system can receive data via a data collection API or through user upload and exportation of their data from a user device API database.

K. Example Healthcare Provider Facing Graphical User Interface

FIGS. 7A-7I Illustrate aspects of an example healthcare provider facing interface.

A system may facilitate a healthcare provider access in some circumstances to user workout data. For example, FIG. 7A illustrates an example visualization of a pool swim workout that may be available to a healthcare provider when shared. The workout visualization may show similar data or visualizations of data as shown to the user, such as heart rate zones, lap times, the like or a combination thereof. Advantageously, access to workout data may allow a healthcare provider to analyze a user's activity for purposes of medical care.

Figure 7B:
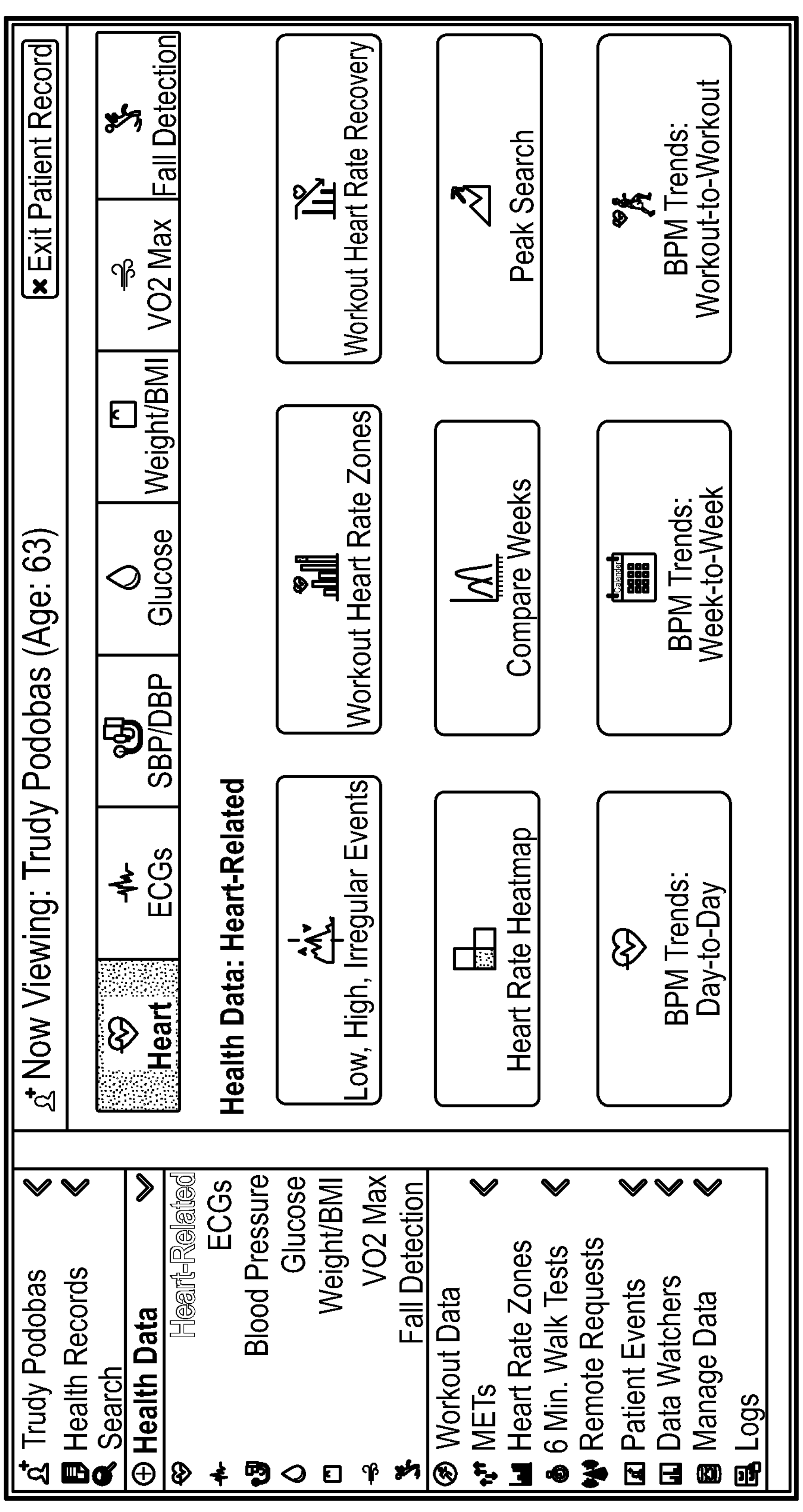

A system may provide a healthcare provider with access to one or more health parameters. Additionally or alternatively, the system may allow a healthcare provider to view events, trends, raw data, or other information relating to collected health data in one or more visualizations. FIG. 7B illustrates example options relating to health related visualizations. Such visualizations can include one or more options to display heart data, ECG data, SBP/DBP data, glucose data, weight/BMI data, VO2 max data, fall detection data, the like or a combination thereof.

Figure 7C:
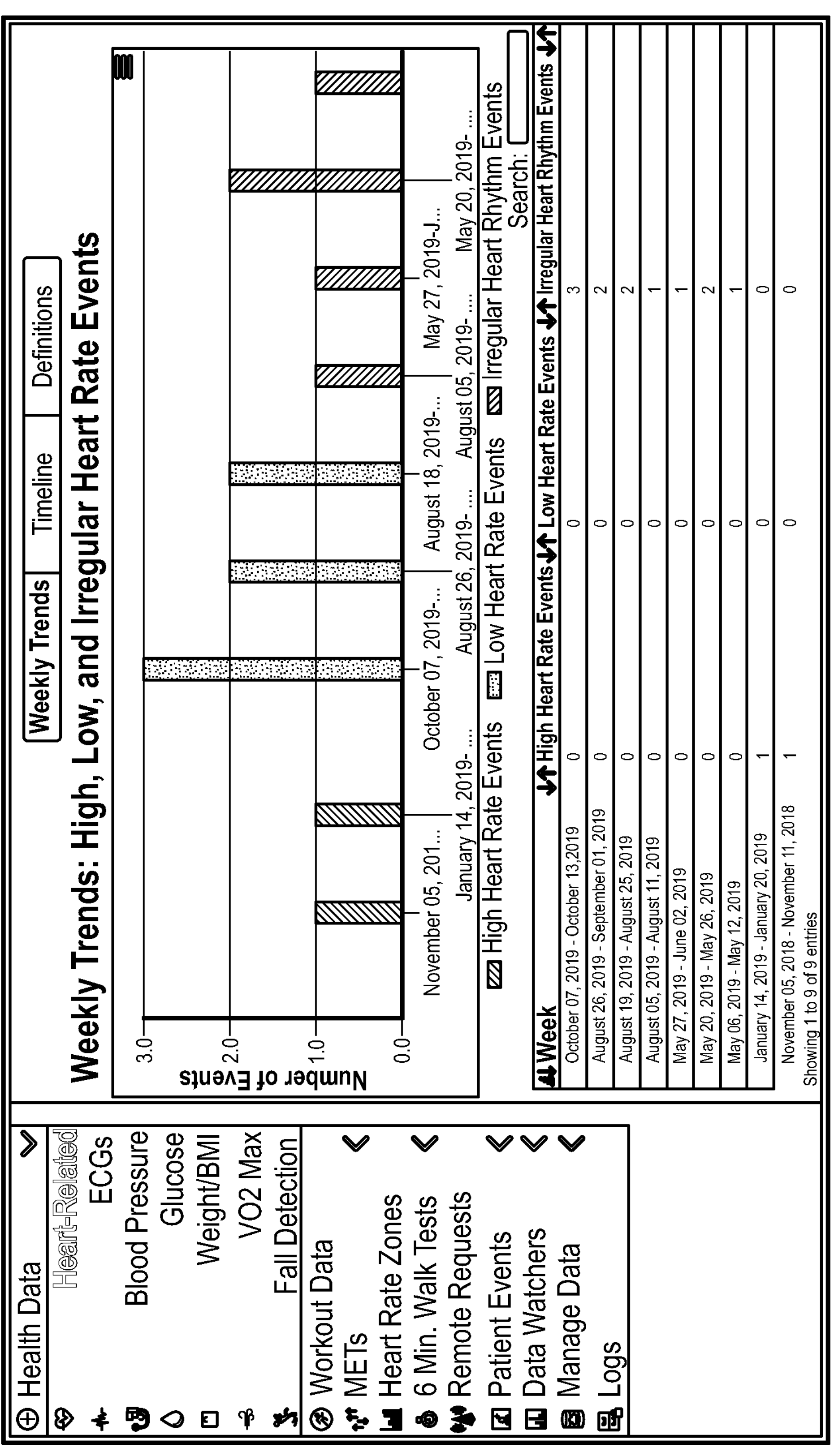
Figure 7D:
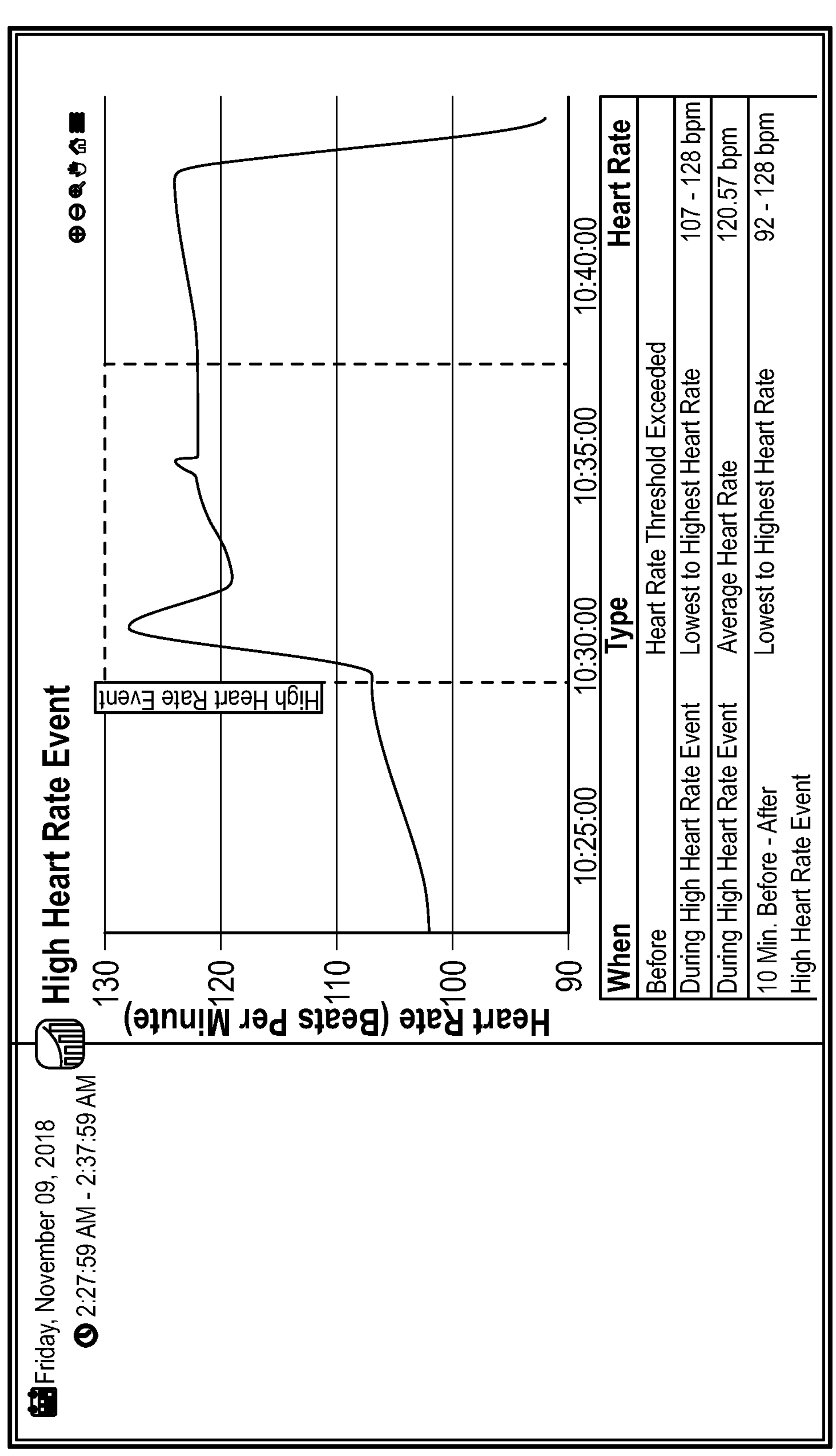
Figure 7E:
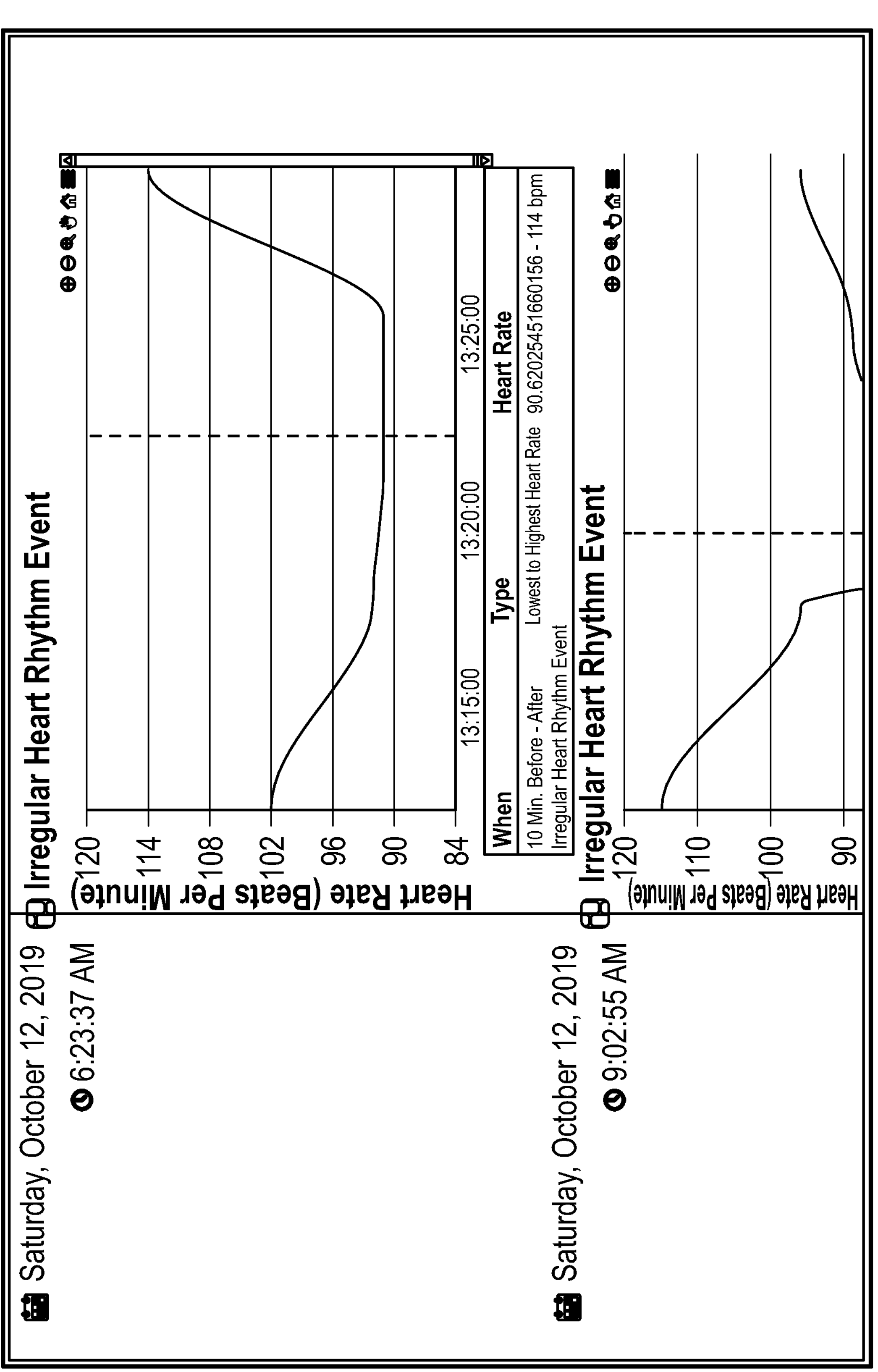

In some examples, a system may provide trend visualizations to a healthcare provider in order to facilitate easy analysis for the healthcare provider. FIG. 7C illustrates an example visualization of heart rate trend data illustrating days of high, low, and/or irregular heart events. However, other visualizations and other parameter monitoring is also possible. For heart rate may be displayed in a timeline format or other visualization format. FIGS. 7D-7E illustrate example timeline events that may be part of an example timeline visualization. For example, as illustrated in FIG. 7D, a system may note a high heart rate event on a timeline. The high heart rate event may be visualized using a graphical format, plotting heart rate against time, optionally highlighting the event within the displayed time frame. Additionally or alternatively, the high heart rate even may be displayed tabularly with rows and columns directed to beats per minute during, before, and after the event. In another example, as illustrated in FIG. 7E, an irregular heart rhythm event may be similarly visualized. Other health parameter based events may be similarly visualized or displayed by the system.

Figure 7F:
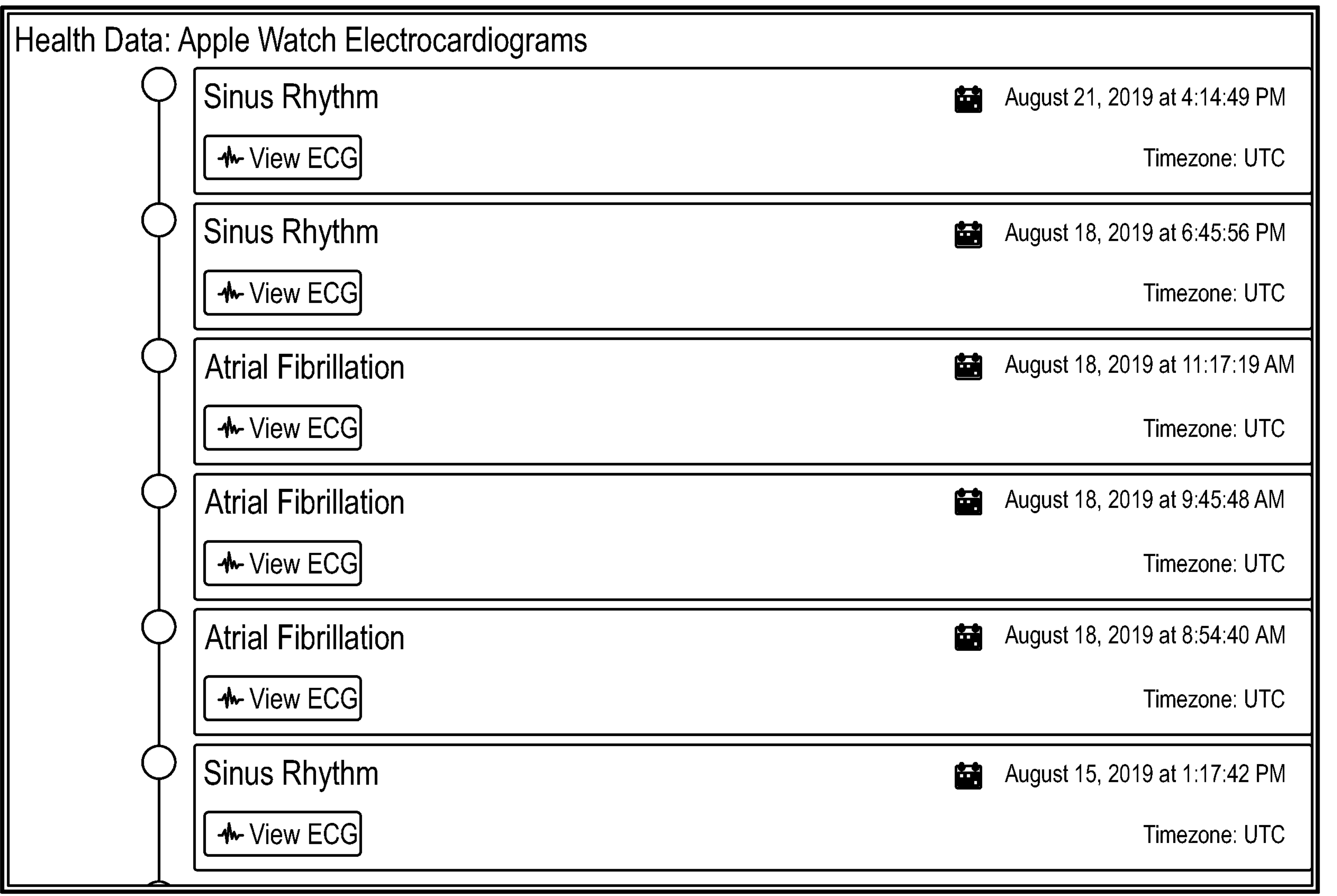

In some examples, a data collection device may collect electrocardiogram data. FIG. 7F illustrates an example electrocardiogram data visualization. For example, the data visualization may include a timeline annotated with information relating to identified ECG related events, such as sinus rhythm and atrial fibrillation. The system may provide one or more options to view or otherwise interact with ECG data associated with the identified event(s).

Figure 7G:
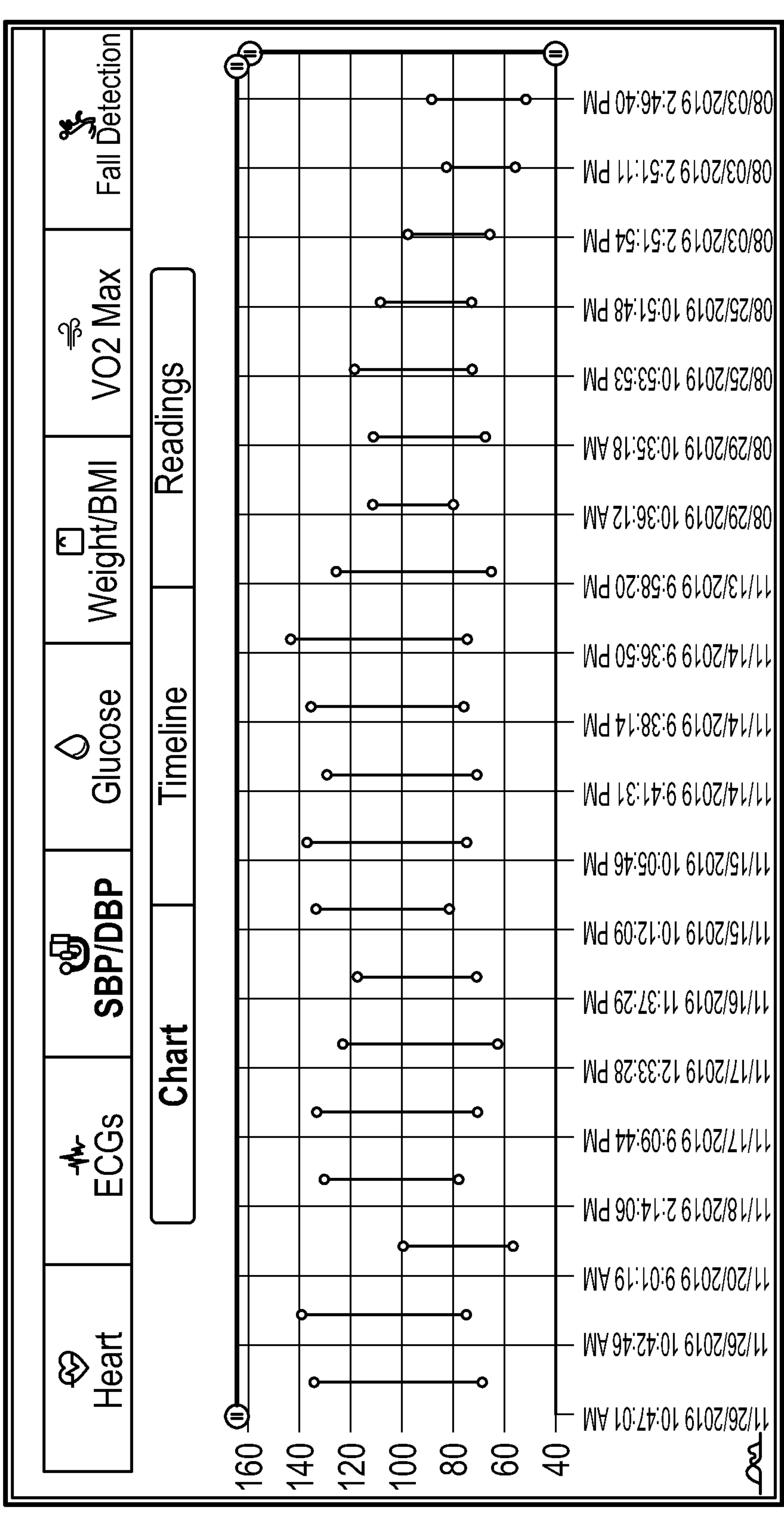
Figure 7H:
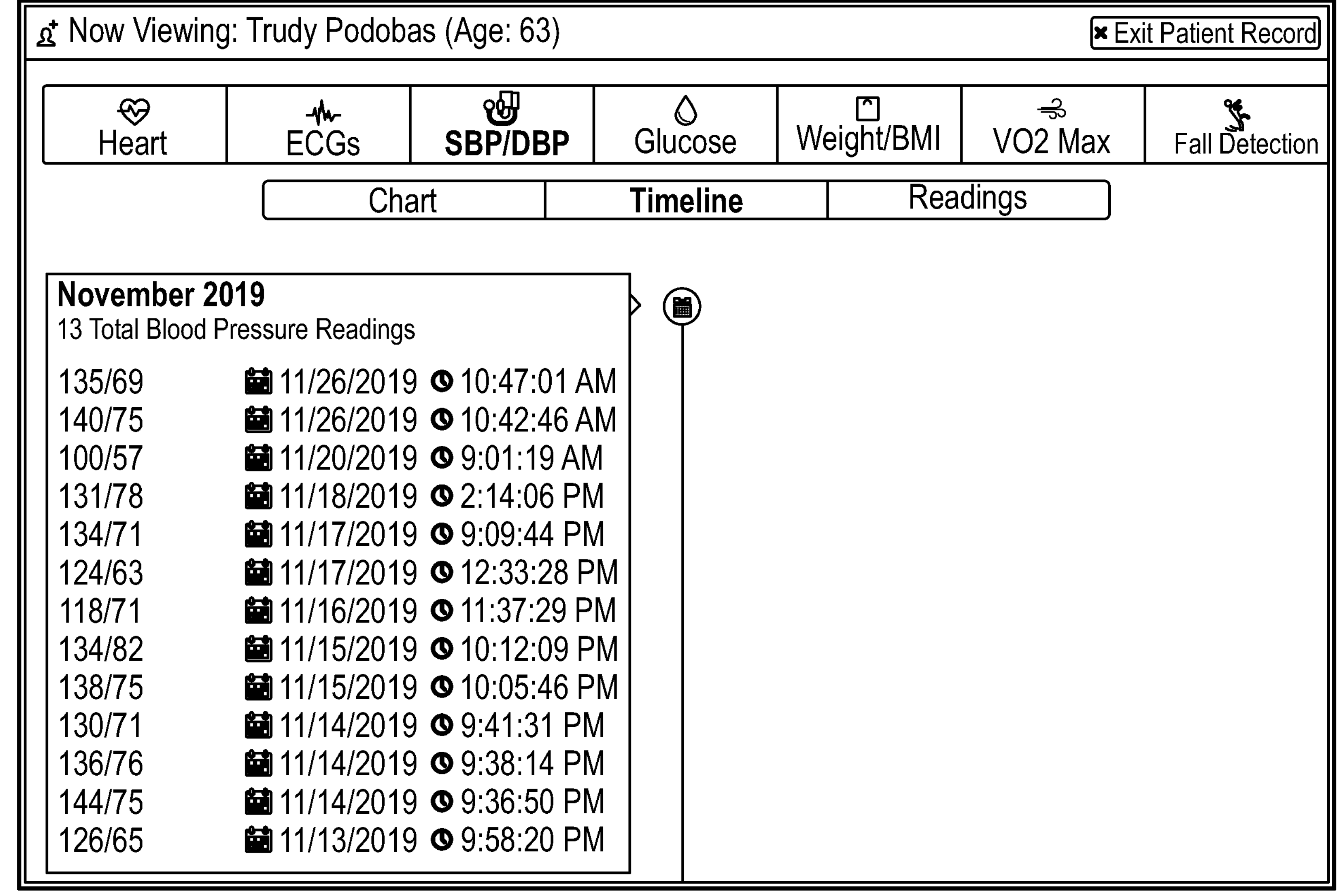

In some examples, a data collection device may collect SBP/DBP data. FIGS. 7G-7I illustrates an example visualization of SBP/DBP data. FIG. 7G illustrates an example chart visualization. FIG. 7H illustrates an example timeline visualization. FIG. 7I illustrates an example tabular visualization.

L. Additional Examples of a Graphical User Interface

Figures 8A, 8B:
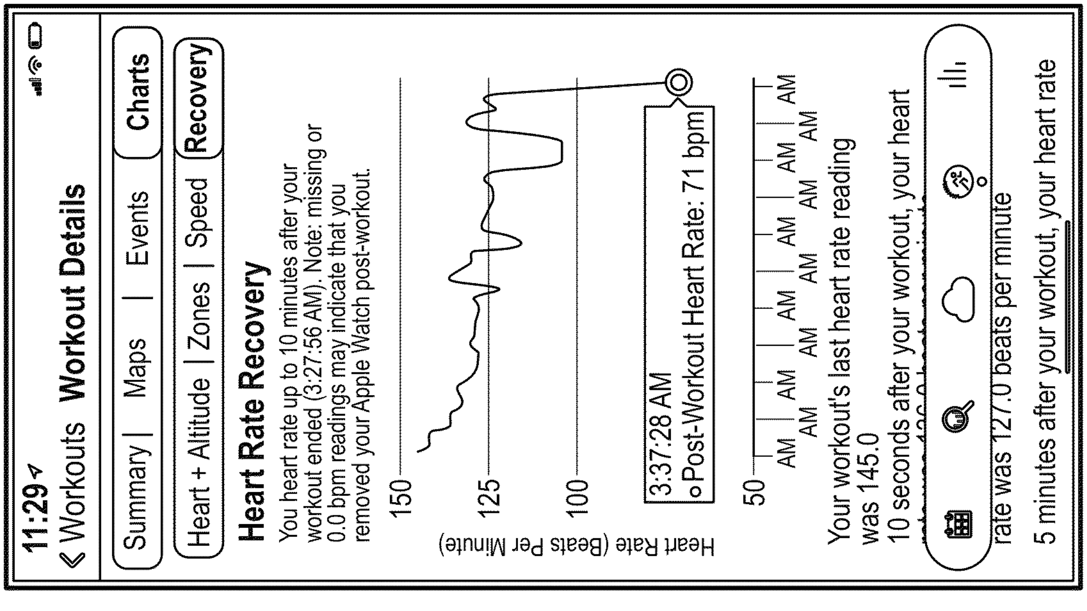
FIGS. 8A-8J illustrate additional examples of a graphical user interface associated with a system.
Figure 8D:
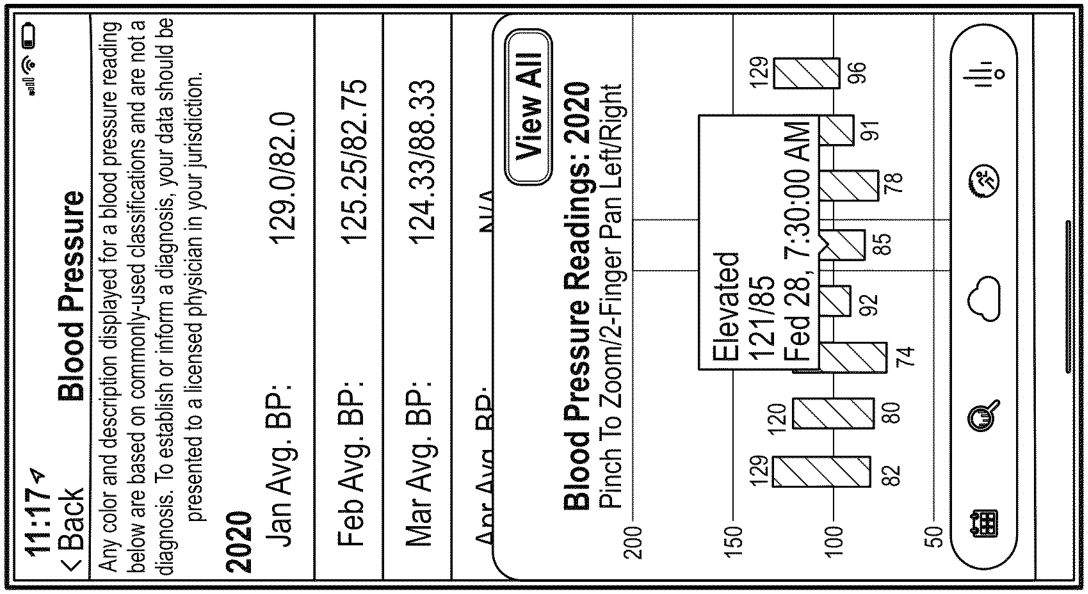
Figure 8C:
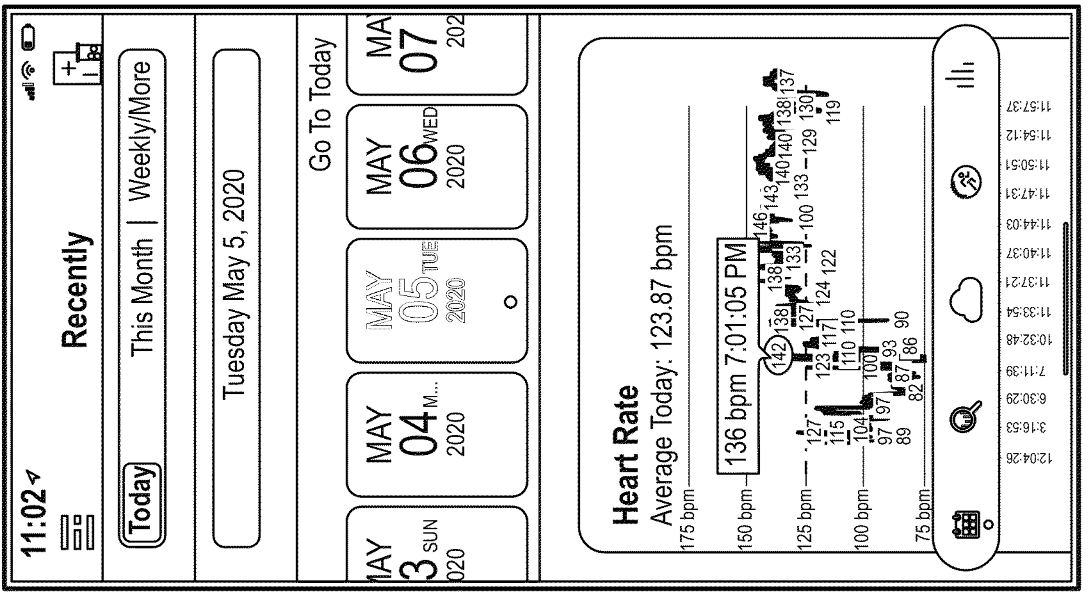

FIGS. 8A-8J illustrate additional examples of a graphical user interface configured for display on a mobile device screen. For example, FIG. 8A illustrates an example infectious disease aspect of a graphical user interface that may display daily averages of biometric parameters, such as breathing, temperature readings, and heart rate for user self-monitoring of COVID-19. FIG. 8B illustrates an example workout detail aspect of a graphical user interface that may display a chart and/or textual data related to heart rate recover associated with a selected workout. FIG. 8C illustrates an example biometric parameter display aspect of a graphical user interface that may display data associated with a selected biometric parameter having multiple measurements, such as heart rate, over the course of a selected day.

FIG. 8D illustrates an example biometric parameter display aspect of a graphical user interface that may display data associated with a selected biometric parameter, such as blood pressure, over the course of a selected month. Additionally, FIG. 8D illustrates an example overlay of more detailed biometric parameter data associated with a selected period of time, such as a selected week, month or year.

Figure 8F:
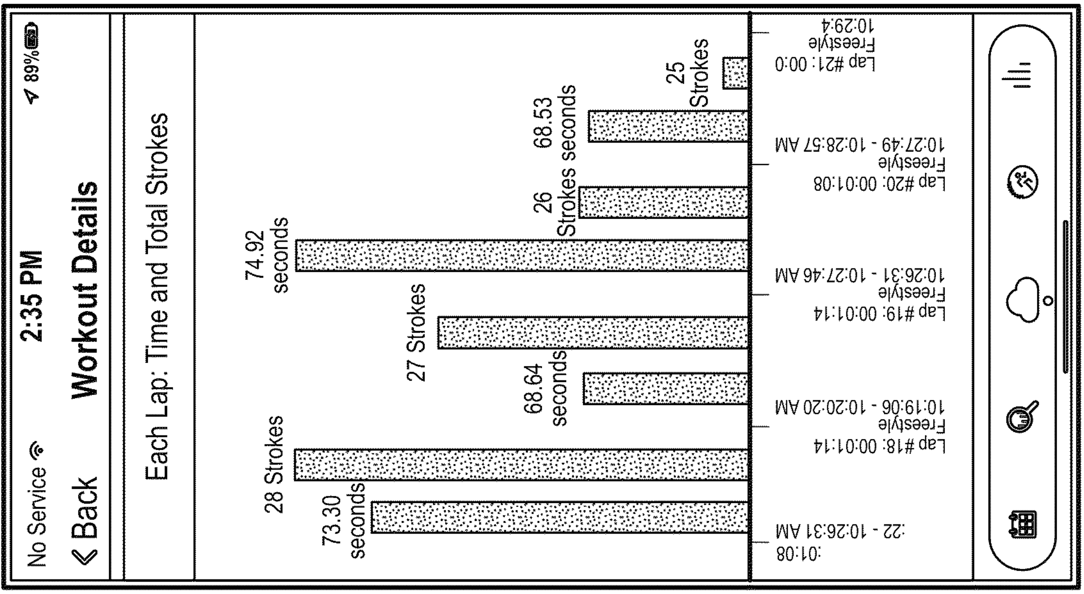
Figure 8E:
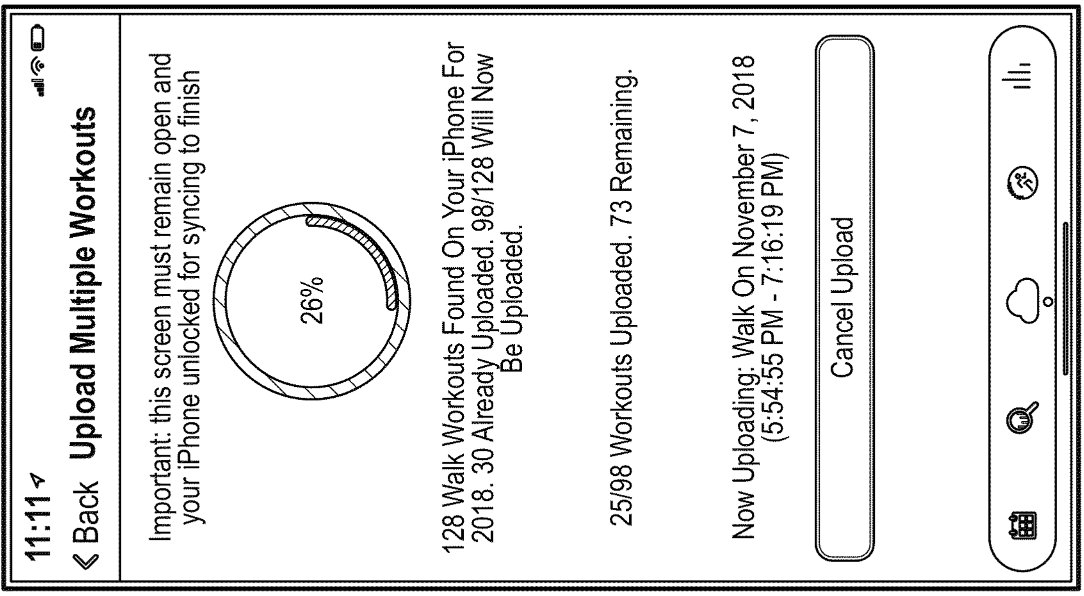

FIG. 8E illustrates an example data upload aspect of a graphical user interface that may display one or more interactive components for initiating, cancelling, or editing an upload of data, and one or more information display components for displaying identified data for potential upload, currently uploading data, or upload progress, such as a progress graph and/or textual display of information. FIG. 8F illustrates an example workout detail aspect of a graphical user interface associated with a particular workout type, such as a swimming workout. In the illustrated example, data, such as lap time and number of swimming strokes may be broken down and displayed based on lap time, real time, stroke type or other workout parameter.

Figure 8H:
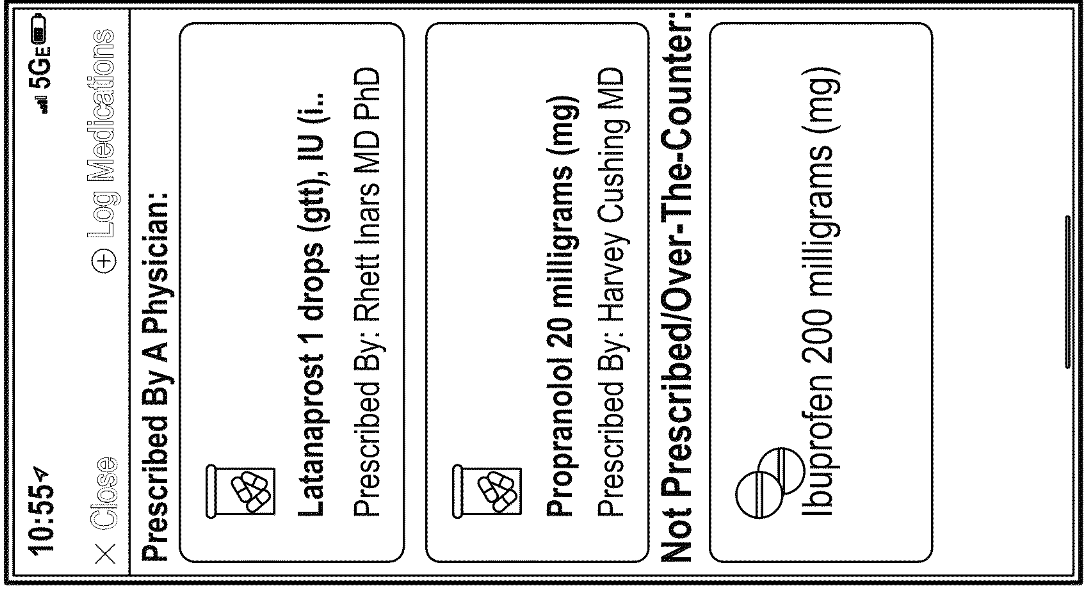
Figure 8G:
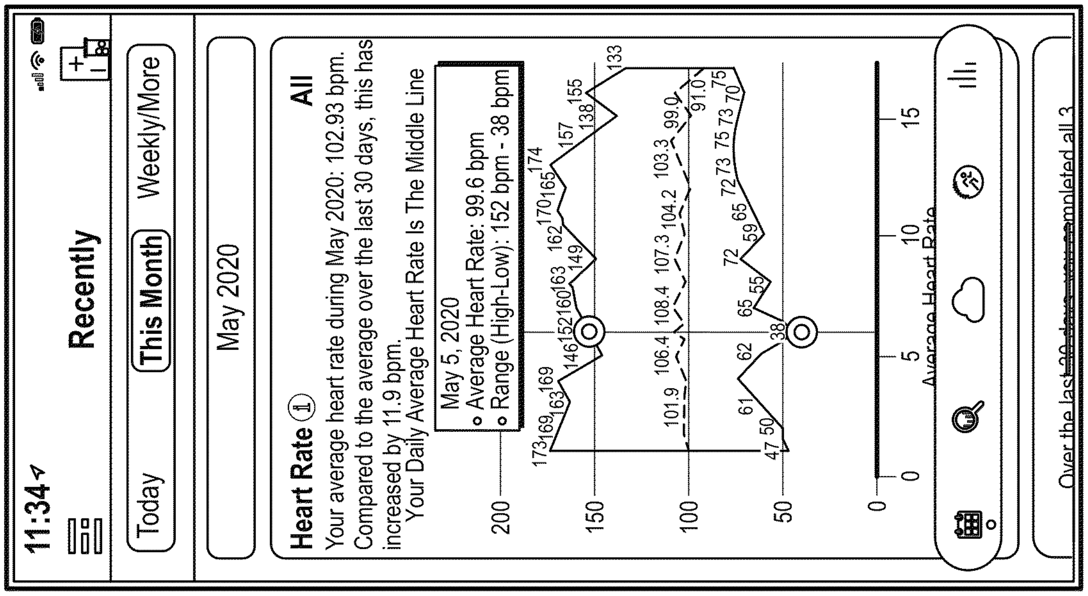

FIG. 8G illustrates an example recent biometric parameter display aspect of a graphical user interface that may display recently acquired biometric parameter data, such as heart rate data, over a selected period of time, such as today, this month, or over a weekly span. FIG. 8H illustrates an example telehealth aspect of a graphical user interface that may enable a user to log or track medications they are taking, prescribed, or otherwise want or need to keep track of due to allergies or other reason. In some examples, the medication log may be accessible and/or editable by a physician, pharmacy, or other third party associated with the user's health care. FIG. 8I illustrates an example manual user input aspect of a graphical user interface that may enable a user to manually input a biometric parameter reading. In some examples, input values may include, the biometric parameter, data, time, and/or other value.

Figure 8J:
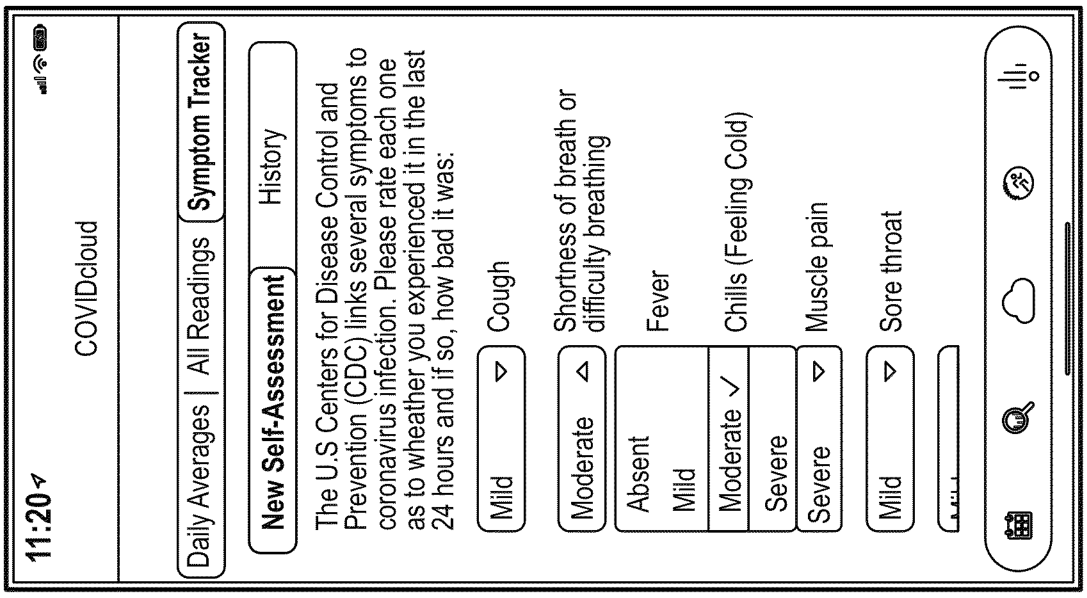
Figure 8I:
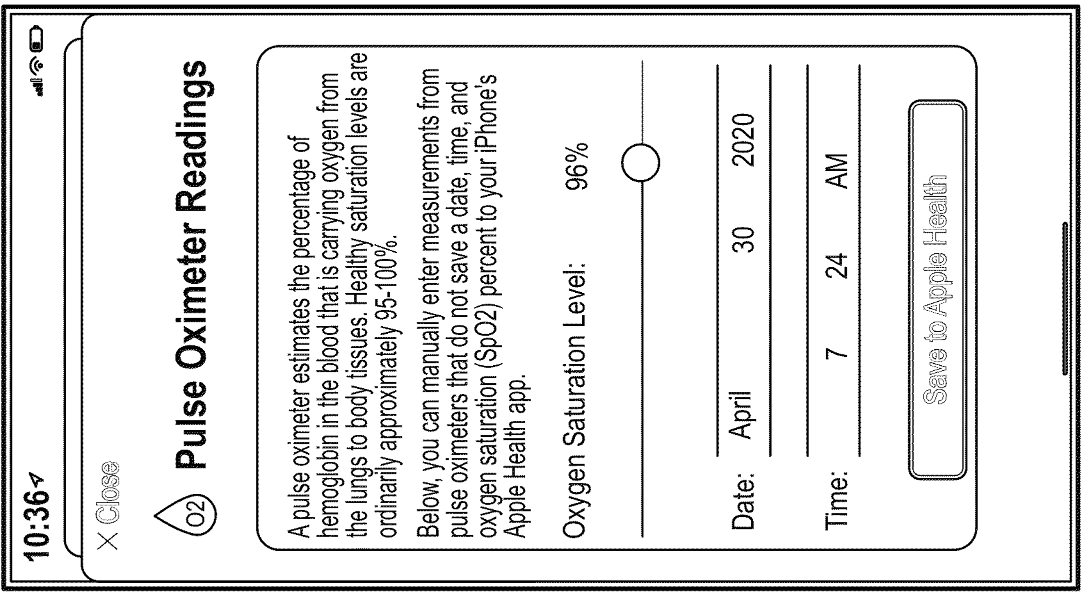

FIG. 8J illustrates an example symptom tracking aspect of a graphical user interface that may be part of an infectious disease monitoring aspect of the system described herein. For example, a user may be enabled to input one or more symptoms in a self-assessment and/or view historical symptom information. Symptoms may include parameters associated with a particular disease, such as COVID-19, including but not limited to: cough, shortness of breath, fever, chills, muscle pain, and sore throat. Other symptoms may also be possible. In some examples, a user may be given an option to identify a presence and/or severity of a symptom by selecting absent, mild, moderate, severe or other value.

While the visualizations described herein are described with reference to specific workouts and data parameters, a person of ordinary skill in the art will appreciate that the visualizations and aspects of the visualizations described herein may be applied to other types of collected data.

Any of the visualizations described herein may be interactive. For example, a visualization may include a graph. The system may facilitate displaying an overlay when a user interacts with a data point on the graph by, for example, hovering or clicking on the data point. A similar overlay may be available for a tabular visualization.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device. Some or all of the methods may alternatively be embodied in whole or in part in specialized computer hardware. The systems described herein may optionally include displays, user input devices (e.g., touchscreen, keyboard, mouse, voice recognition, camera, etc.), network interfaces, etc.

The user devices described herein may be in the form of a mobile communication device (e.g., a cell phone, a VoIP equipped mobile device, etc.), laptop, tablet computer, interactive television, game console, media streaming device, head-wearable display, virtual reality display/headset, augmented reality display/headset, networked watch, etc. The user devices may optionally include displays, user input devices (e.g., touchscreen, keyboard, mouse, voice recognition, cameras, etc.), network interfaces, etc.

The results of the disclosed methods may be stored in any type of computer data repository, such as relational databases and flat file systems that use volatile and/or nonvolatile memory (e.g., magnetic disk storage, optical storage, EEPROM and/or solid state RAM).

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user device. In the alternative, the processor device and the storage medium can reside as discrete components in a user device.

M. Additional Examples

Disclosed herein are additional examples of systems and methods for securely communicating over networks, in real time, and utilizing biometric and other data. Any of the disclosed examples or aspects of the disclosed examples may be combined or independently applied in whole or in part.

Example 1: A health data visualization system, the system comprising:

a non-transitory computer storage medium configured to at least store computer-readable instructions; and one or more hardware processors in communication with the non-transitory computer storage medium, the one or more hardware processors configured to execute the computer-readable instructions to at least:

receive a set of biometric user data from at least one of a plurality of different sources;

identify a category parameter associated with the one or more values of the set of biometric user data;

upload the biometric user data and category parameter to a remote server;

receive a query to view the biometric user data;

determine a graphical representation of the biometric user data;

cause presentation of the graphical representation within a graphical user interface on a computer screen.

Example 2: The system of Example 1, wherein the plurality of different sources comprise at least one of: a medical record database, wearable device configured to measure biometric user data, user input, or clinician input.

Example 3: The system of Examples 1 or 2, wherein the classification parameter comprises at least one of a time stamp, time zone, or data type.

Example 4: The system any one of Examples 1-3, wherein the query comprises a textual or auditory query by a user.

Example 5: The system of any one of Examples 1-4, wherein to cause presentation of the graphical representation, the one or more hardware processors are configured to:

select biometric user data of the set of biometric user data based on the category parameter and the query; and cause display of the selected biometric user data within a graphical user interface on the computer screen.

Example 6: The system of Example 5, wherein to select biometric user data, the one or more hardware processors are configured to:

determine a first range of time;

determine a representative biometric user data value for a second range of time less than the first range of time; and cause display of the representative biometric user data value.

Example 7: The system of any one of Examples 5-6, wherein the first range of time comprises a plurality of days.

Example 8: The system of any one of Examples 5-7, wherein the plurality of days comprises 30 days, 60 days, or 90 days.

Example 9: The system of any one of Examples 5-8, wherein the second range of time comprises one day.

Example 10: The system of any one of Examples 5-9, wherein the second range of time comprises one week.

Example 11: The system of any one of Examples 5-10, wherein to determine the representative biometric data value, the one or more hardware processors are configured to average a plurality of biometric user data values obtained during the second range of time.

Example 12: The system of any one of Examples 1-11, wherein the set of biometric user data comprises at least one of: workout data, biometric parameter data, or medical record data.

Example 13: A health data communication system, the system comprising:

a non-transitory computer storage medium configured to at least store computer-readable instructions; and one or more hardware processors in communication with the non-transitory computer storage medium, the one or more hardware processors configured to execute the computer-readable instructions to at least:

facilitate communication between a device of a first user and a device of a second user;

cause to display audiovisual information associated with the communication within a graphical user interface on the device of the first user;

receive a request to access health information associated with the second user from the first user; and cause to display, within the graphical user interface on the device of the first user, the health information while continuing to output audiovisual information associated with the communication.

Example 14: The system of Example 13, wherein the audiovisual information comprises audio information.

Example 15: The system of Example 13 or 14, wherein the audiovisual information comprises video and audio information.

Example 16: The system of any of Examples 13-15, wherein the request to access health information comprises an interaction of a user with an interactive component of the graphical user interface.

Example 17: The system of any of Examples 13-16, wherein the interactive component a tab associated with health information.

Example 18: The system of any of Examples 13-17, wherein the one or more hardware processors are configured to cause the device of the first user to output audio information associated with the communication while the device displays the health information.

Example 19: The system of any of Examples 13-18, wherein the health information comprises medical record data.

Example 20: The system of any of Examples 13-19, wherein the health information comprises one or more values of physiological parameters measured by at least one physiological sensor.

Example 21: The system of Example 20, wherein the at least one physiological sensor is associated with a wearable device.

Example 22: A health data communication system, the system comprising:

a non-transitory computer storage medium configured to at least store computer-readable instructions; and one or more hardware processors in communication with the non-transitory computer storage medium, the one or more hardware processors configured to execute the computer-readable instructions to at least:

facilitate communication between a device of a first user and a device of a second user;

cause to display audiovisual information associated with the communication within a graphical user interface on the device of the first user;

receive physiological data associated with the second user, the physiological data obtained during the communication by at least one sensor configured to measure one or more physiological parameters from the second user; and cause to display, within the graphical user interface on the device of the first user, the physiological data while continuing to output audiovisual information associated with the communication.

Example 23: The system of Example 22, wherein the physiological data comprises heart rate.

Example 24: The system of any one of Examples 22 or 23, wherein the at least one sensor is associated with a wearable device.

Example 25: The system of any one of Examples 22-24, wherein the one or more hardware processors are configured to receive an indication of a start of an activity and wherein to cause the display the physiological data, the one or more hardware processors are configured to cause to display the physiological data based on the activity.

Example 26: The system of Example 25, wherein the activity comprises a health diagnostic test.

Example 27: The system of any of Examples 22-26, wherein the one or more hardware processors are configured to cause the device of the first user to output audio information associated with the communication while the device displays the physiological information.

Example 28: A health data communication system, the system comprising:

a non-transitory computer storage medium configured to at least store computer-readable instructions; and one or more hardware processors in communication with the non-transitory computer storage medium, the one or more hardware processors configured to execute the computer-readable instructions to at least:

facilitate communication between a device of a first user and a device of a second user;

receive a request to end the communication;

in response to receiving the request, automatically record information associated with the communication in a database, the information associated with the communication comprising: an identify of the first user and the second user, a start time of the communication, an end time of the communication, and a duration of the communication; and format the recorded information for generation of an invoice for healthcare services provided during the communication.

Example 29: The system of Example 28, wherein the one or more hardware processors are configured to cause to display audiovisual information associated with the communication within a graphical user interface on the device of the first user.

Example 30: The system of any one of Examples 28 or 29, wherein the request originated from the device of the first user or the device of the second user.

Example 31: The system of any one of Examples 28-30, wherein the one or more hardware processors are configured to automatically record input from the first user.

Example 32: The system of any one of Examples 28-31, wherein the one or more hardware processors are configured to automatically record activity of the first user in a graphical user interface displayed on the device of the first user.

Example 33: The system of any one of Examples 28-32, wherein the first user is a health care provider and the second user is a patient.

Example 34: The system of any one of Examples 28-33, wherein the one or more hardware processors are configured to:

in response to the request to end the communication, cause to display on the device of the first user a prompt for information associated with healthcare services provided during the communication.

Example 35: The system of Example 34, wherein the one or more hardware processors are configured to: record the information associated with the healthcare services provided in the database.

Example 36: The system of any one of Examples 28-35, wherein the one or more hardware processors are configured to: generate an invoice for health services provided during the communication.

Example 37: A system comprising:

a non-transitory computer storage medium configured to at least store computer-readable instructions; and one or more hardware processors in communication with the non-transitory computer storage medium, the one or more hardware processors configured to execute the computer-readable instructions to at least:

receive a plurality of user data from a plurality of different sensors, wherein at least one sensor of the plurality of different sensors is configured to measure one or more biometric parameters associated with a user;

upload the plurality of user data to a remote server;

receive processed data based on the uploaded plurality of user data;

select data values from the processed data, the selected data values comprising:

a first data value of a first parameter type at a first time, a second data value of the first parameter type at a second time, a third data value of a second parameter type at the first time, and a fourth data value of the second parameter type at the second time;

determine a graphical representation of the selected data values, the graphical representation comprising a combination chart;

determine a tabular representation of the selected data; and cause presentation of the graphical representation and the tabular representation within a graphical user interface on a computer screen.

Example 38: A system comprising:

a non-transitory computer storage medium configured to at least store computer-readable instructions; and one or more hardware processors in communication with the non-transitory computer storage medium, the one or more hardware processors configured to execute the computer-readable instructions to at least:

receive a plurality of user data comprising at least one of:

sensor data from a plurality of different sensors, wherein at least one sensor of the plurality of different sensors is configured to measure one or more biometric parameters associated with the user that is indicative of an infectious disorder; and input data from a device of the user, the input data comprising at least one of a presence or severity of symptoms associated with the infectious disorder;

upload the plurality of user data to a remote server;

receive processed data based on the uploaded plurality of user data;

select data values from the processed data, the selected data values comprising:

a first data value of a first parameter type at a first time, a second data value of the first parameter type at a second time, a third data value of a second parameter type at the first time, and a fourth data value of the second parameter type at the second time;

determine a graphical representation of the selected data values, the graphical representation comprising a combination chart;

determine a tabular representation of the selected data; and cause presentation of the graphical representation and the tabular representation within a graphical user interface on a computer screen.

Example 39: A system comprising:

a non-transitory computer storage medium configured to at least store computer-readable instructions; and one or more hardware processors in communication with the non-transitory computer storage medium, the one or more hardware processors configured to execute the computer-readable instructions to at least:

receive a plurality of first patient data comprising:
sensor data from a plurality of different sensors, wherein at least one sensor of the plurality of different sensors is configured to measure one or more biometric parameters associated with a first patient that is indicative of an infectious disorder; and
patient input data from a device of the patient, the patient input data comprising at least one of a presence or severity of patient symptoms associated with the infectious disorder;
process the plurality of first patient data for display within a graphical user interface on a computer screen;
receive a request from a user to display at least some of the plurality of first patient data;
determine a authentication access level associated with the user;
cause, based on the authentication access level, display of the at least some of the plurality of first patient data on a device of the user.

Example 40: A system comprising:
a non-transitory computer storage medium configured to at least store computer-readable instructions; and
one or more hardware processors in communication with the non-transitory computer storage medium, the one or more hardware processors configured to execute the computer-readable instructions to at least:
receive a plurality of first patient data from a plurality of different sensors, wherein at least one sensor of the plurality of different sensors is configured to measure one or more biometric parameters associated with a first patient that is indicative of an infectious disorder;
process the plurality of first patient data for display within a graphical user interface on a computer screen;
receive a request from a user to display at least some of the plurality of first patient data;
determine a authentication access level associated with the user;
cause, based on the authentication access level, display of the at least some of the plurality of first patient data on a device of the user.

Example 41: A health data visualization system, the system comprising:
a non-transitory computer storage medium configured to at least store computer-readable instructions; and
one or more hardware processors in communication with the non-transitory computer storage medium, the one or more hardware processors configured to execute the computer-readable instructions to at least:
receive a set of biometric user data from at least one of a plurality of different sources;
preprocess the biometric user data so as to reduce a quantity of data for transmission across a network to thereby reduce network bandwidth utilization;
upload the preprocessed biometric user data to a remote server across a network;
receive a query to view the biometric user data;
receive the preprocessed biometric user data; and
cause presentation of the biometric user data within a graphical user interface on a computer screen.

Example 42: The system of claim 1, wherein the plurality of different sources comprise at least one of: a medical record database, wearable device configured to measure biometric user data, user input, or clinician input.

Example 43: The system of claim 1 or 2, wherein to preprocess the biometric user data, the one or more hardware processors are configured to:
determine a category parameter associated with at least some of the biometric user data, wherein the category parameter comprises at least one of a time stamp, time zone, or data type.

Example 44: The system any one of claims 1-3, wherein the query comprises a textual or auditory query by a user.

Example 45: The system of any one of claims 1-4, wherein to cause presentation of the biometric data, the one or more hardware processors are configured to:
select biometric user data of the set of biometric user data based on a category parameter and the query; and
cause display of the selected biometric user data within the graphical user interface on the computer screen.

Example 46: The system of claim 5, wherein to select biometric user data, the one or more hardware processors are configured to:
determine a first range of time;
determine a representative biometric user data value for a second range of time less than the first range of time; and
cause display of the representative biometric user data value.

Example 47: The system of any one of claims 5-6, wherein the first range of time comprises a plurality of days.

Example 48: The system of any one of claims 5-7, wherein the plurality of days comprises 30 days, 60 days, or 90 days.

Example 49: The system of any one of claims 5-8, wherein the second range of time comprises one day.

Example 50: The system of any one of claims 5-9, wherein the second range of time comprises one week.

Example 51: The system of any one of claims 5-10, wherein to determine the representative biometric data value, the one or more hardware processors are configured to average a plurality of biometric user data values obtained during the second range of time.

Example 52: The system of any one of claims 1-11, wherein the set of biometric user data comprises at least one of: workout data, biometric parameter data, or medical record data.

N. Example Key and Value Pairs for an Example Running Workout

The example below shows potential key and value pairs of a dictionary used to organize the contents of a running type workout.

```
let workoutEvents = workoutsync.workoutEvent
let dateFormatter_YearMonthDay = DateFormatter( )
dateFormatter_YearMonthDay.dateFormat = "yyyy-MM-dd"
let dateFormatter_YearMonth = DateFormatter( )
dateFormatter_YearMonth.dateFormat = "yyyy-MM"
let dateFormatter_Year = DateFormatter( )
dateFormatter_Year.dateFormat = "yyyy"
let strPrepend = "HKWorkoutActivityType"
```

-continued

```
let workout_to_upload = [
    "workoutType": strPrepend+workoutsync.activityType,
    "startDate": "\(dateFormatter.string(from: workoutsync.startDate))",
    "endDate": "\(dateFormatter.string(from: workoutsync.endDate))",
    "duration": workoutsync.duration,
    "durationUnit": "seconds",
    "totalDistance": workoutsync.totalDistance,
    "totalEnergyBurned": "\(workoutsync.totalEnergyBurned)",
    "metadata": "\(workoutsync.metaData)" as AnyObject,
     "timezone": metaData_timezone ,
    "temperature": metaData_temperature ,
    "humidity": metaData_humidity ,
    "elevation_ascendded": metaData_elevationAscended,
    "elevation_descended": metaData_elevationDescended ,
    "workout_type_indoor_or_outdoor": metaData_indoor_or_outdoor ,
    "average_METs": metaData_METs_average,
    "maximum_METs": metaData_METs_max,
    "year-month-day": "\(dateConvertTo_YearMonthDay)",
    "year-month": "\(dateConvertTo_YearMonth)",
    "year": "\(dateConvertTo_Year)",
    "ISOweek-year": "\(dateConvertTo_WeekOfYear)-" + "\(dateConvertTo_Year)",
    "workoutData_events": "\(workoutsync.workoutEvents)",// as AnyObject,
  "workoutData_geolocation": UserData.sharedUserData.routeSyncData,
    "workoutData_distance":UserData.sharedUserData.distanceWalkingRunningHKQ
uantitySamples,
   "workoutData_heartRate": UserData.sharedUserData.arrayHeartRate,
 "workoutData_heartRateRecovery": UserData.sharedUserData.arrayHeartRateRecovery,
  "workoutData_heartRateZones": UserData.sharedUserData.arrayHeartRateZones,
 "workoutData_metabolic_equivalents": UserData.sharedUserData.arrayMETs,
    "workoutData_mile_times": UserData.sharedUserData.arrayWorkoutMileTimes,
  ] as NSDictionary
```

O. Terminology

Many other variations than those described herein will be apparent from this disclosure. For example, depending on the embodiment, certain acts, events, or functions of any of the steps described herein can be performed in a different sequence, can be added, merged, or left out altogether (e.g., not all described acts or events are necessary for the practice of the algorithms). Moreover, in certain embodiments, acts or events can be performed concurrently. In addition, different tasks or processes can be performed by different machines and/or computing systems that can function together.

While the phrase "click" may be used with respect to a user selecting a control, menu selection, or the like, other user inputs may be used, such as voice commands, text entry, gestures, etc. For example, a click may be in the form of a user touch (via finger or stylus) on a touch screen, or in the form of a user moving a cursor (using a mouse of keyboard navigation keys) to a displayed object and activating a physical control (e.g., a mouse button or keyboard key). User inputs may, by way of example, be provided via an interface or in response to a prompt (e.g., a voice or text prompt). By way of example an interface may include text fields, wherein a user provides input by entering text into the field. By way of further example, a user input may be received via a menu selection (e.g., a drop down menu, a list or other arrangement via which the user can check via a check box or otherwise make a selection or selections, a group of individually selectable icons, a menu selection made via an interactive voice response system, etc.). When the user provides an input or activates a control, a corresponding computing system may perform a corresponding operation (e.g., store the user input, process the user input, provide a response to the user input, etc.). Some or all of the data, inputs and instructions provided by a user may optionally be stored in a system data store (e.g., a database), from which the system may access and retrieve such data, inputs, and instructions. The notifications and user interfaces described herein may be provided via a Web page, a dedicated or non-dedicated phone or wearable device application, computer application, a short messaging service message (e.g., SMS, MMS, etc.), instant messaging, email, push notification, audibly, and/or otherwise.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as “a” or “an” should generally be interpreted to include one or more described items. Accordingly, phrases such as “a device configured to” are intended to include one or more recited devices. Such one or more recited devices can also be collectively configured to carry out the stated recitations.

While the above detailed description has shown, described, and pointed out novel features as applied to various embodiments, it will be understood that various omissions, substitutions, and changes in the form and details of the apparatus or method illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method of communicating health information, the method comprising:

receiving data at a network interface from a plurality of sources associated with a patient, the plurality of sources having at least some disparate data storage application programming interfaces, the plurality of sources comprising:

a data source configured to collect physiological sensor data from the patient; and medical record data from a plurality of disparate different electronic health record data stores having respective different data storage application programming interfaces;

processing and aggregating the data from the plurality of sources having at least some disparate data storage application programming interfaces to fit a pre-determined format to generate processed data, such processing comprising at least data correlation of different types of data from different sources of the plurality of sources, having one or more common characteristics, the pre-determined format comprising a graph and/or a table;

saving the processed data to a database, the processed data generated from the data from plurality of sources having disparate data storage application programming interfaces to fit the pre-determined format;

facilitating real-time communication between a computing device of a user and a computing device of the patient, wherein the computing device of the user comprises:

a first camera, a first microphone, a first sound reproduction device, and a first display;

wherein the computing device of the patient comprises:

a second camera, a second microphone, a second sound reproduction device, and a second display;

enabling audiovisual information of the user to be captured using the first camera and the first microphone associated with the computing device of the user;

enabling a real-time audio-visual telehealth call between the computing device of the patient and the computing device of the user;

enabling a real time display of real time visual information associated with the real-time audio-visual telehealth call within a graphical user interface on the first display of the computing device of the user, and enabling audio information associated with the real-time audio-visual telehealth call to be reproduced using the second sound reproduction device;

receiving a request to access the processed data associated with the patient from the computing device of the user, the processed data generated from received data from the data source configured to collect physiological sensor data from the patient and from the plurality of disparate different electronic health record data stores having respective different data storage application programming interfaces to fit the pre-determined format;

causing to display within the graphical user interface a first navigable screen that provides access to a plurality of other navigable screens on the first display of the computing device of the user, the first navigable screen and the plurality of other navigable screens configured to display:

telehealth visit content, and respective subsets of the processed data generated from the received data from the data source configured to collect physiological sensor data from the patient and from the plurality of disparate different electronic health record data stores having respective different data storage application programming interfaces to fit the pre-determined format, while continuing to output visual information on the first display of the computing device of the user, wherein the first navigable screen, and respective other navigable screens in the plurality of other navigable screens, are respectively configured to display aspects of at least some of the data from the plurality of sources;

receiving a request to end the real-time communication between the computing device of the user and the computing device of the patient; and in response to receiving the request, automatically recording information associated with the real-time communication in a database, the information associated with the real-time communication comprising: an identity of the user, an identity of the patient, a start time of the real-time communication, an end time of the real-time communication, a duration of the real-time communication, and an alphanumeric code representative of a subject of the real-time communication.

2. The method of claim 1, wherein the request to access the processed data comprises an interaction of the user with an interactive component of the graphical user interface.

3. The method of claim 2, wherein the interactive component comprises a tab associated with health information.

4. The method of claim 1, wherein the physiological sensor data comprises at least one physiological parameter associated with heart rate.

5. The method of claim 1, wherein the data source configured to collect physiological sensor data from the patient comprises data from a dedicated physiological sensor comprising a pulse oximeter, blood pressure cuff, ECG sensor, weight sensor, or glucometer.

6. The method of claim 1 comprising formatting recorded information for generation of an invoice for healthcare provided to a subject of the real-time communication.

7. The method of claim 1 comprising:

selecting data values from the processed data, selected data values comprising:

a first data value of a first parameter type at a first time, a second data value of the first parameter type at a second time, a third data value of a second parameter type at the first time, and a fourth data value of the second parameter type at the second time;

determining a graphical representation of the selected data values, the graphical representation comprising a combination chart;

determining a tabular representation of the selected data; and causing presentation of the graphical representation and the tabular representation within the graphical user interface.

8. The method of claim 1, wherein the pre-determined format comprises time zone or time zone information.

9. The method of claim 1, wherein the pre-determined format comprises billing codes such as CPT or HCPCS.

10. A health data communication system, the system comprising:

a network interface configured to receive data from a plurality of sources:

a non-transitory computer storage medium configured to at least store computer-readable instructions; and one or more hardware processors in communication with the non-transitory computer storage medium, the one or more hardware processors configured to execute the computer-readable instructions to at least:

receive data from the plurality of sources associated with a patient, the plurality of sources having at least some disparate data storage application programming interfaces, the plurality of sources comprising:

one or more physiological data sources configured to provide physiological data from one or more sensors, and medical record data from a plurality of disparate different electronic health record data stores having respective different data storage application programming interfaces, the medical record data comprising clinical notes;

process and aggregate the data from the plurality of sources having at least some disparate data storage application programming interfaces to fit a pre-determined format to generate processed data, such processing comprising at least data correlation of different types of data from different sources of the plurality of sources, having one or more common characteristics, the pre-determined format comprising a graph and/or a table;

save the processed data to a database, the processed data generated from received data from the one or more physiological data sources and the plurality of disparate different electronic health record data stores having respective different data storage application programming interfaces to fit the pre-determined format;

facilitate real-time communication over at least one network between a computing device of a user and a computing device of the patient, wherein the computing device of the user comprises:

a first camera, a first microphone, a first sound reproduction device, and a first display;

wherein the computing device of the patient comprises:

a second camera, a second microphone, a second sound reproduction device, and a second display;

enable audiovisual information of the user to be captured using the first camera and the first microphone;

enable a real-time audio-visual telehealth call between the computing device of the patient and the computing device of the user;

enable a real time display of visual information associated with the real-time audio-visual telehealth call within a graphical user interface on the first display of the computing device of the user, and enable audio information associated with the real-time audio-visual telehealth call to be reproduced using the second sound reproduction device;

receive a request to access the processed data associated with the patient from the computing device of the user, the processed data generated from the received data from the one or more physiological data sources and from the plurality of disparate different electronic health record data stores having respective different data storage application programming interfaces to fit the pre-determined format;

cause to display, within the graphical user interface, a first navigable screen that provides access to a plurality of other navigable screens on the first display of the computing device of the user, the first navigable screen and the plurality of other navigable screens configured to display:

telehealth visit content, and respective subsets of the processed data generated from the received data from the one or more physiological data sources and from the plurality of disparate different electronic health record data stores having respective different data storage application programming interfaces to fit the pre-determined format, while continuing to output visual information on the first display of the computing device of the user, wherein the first navigable screen, and respective other navigable screens in the plurality of other navigable screens, are respectively configured to display aspects of at least some of the plurality of sources;

receive a request to end the communication between the computing device of the user and the computing device of the patient; and in response to receiving the request, automatically record information associated with the communication in a database, the information associated with the communication comprising: an identity of the user, an identity of the patient, a start time of the communication, an end time of the communication, a duration of the communication, and an alphanumeric code representative of a subject of the communication.

11. The system of claim 10, wherein the request to access the processed data comprises an interaction of the user with an interactive component of the graphical user interface.

12. The system of claim 11, wherein the interactive component comprises a tab associated with health information.

13. The system of claim 10, wherein the physiological data comprises at least one physiological parameter associated with heart rate.

14. The system of claim 10, wherein the one or more sensors comprise a dedicated physiological sensor comprising a pulse oximeter, blood pressure cuff, ECG sensor, weight sensor, or glucometer.

15. The system of claim 10, wherein the one or more hardware processors are configured to: format the recorded information for generation of an invoice for healthcare provided to a subject of the communication.

16. The system of claim 10, wherein the one or more hardware processors are configured to:

select data values from the processed data, the selected data values comprising:

a first data value of a first parameter type at a first time, a second data value of the first parameter type at a second time, a third data value of a second parameter type at the first time, and a fourth data value of the second parameter type at the second time;

determine a graphical representation of the selected data values, the graphical representation comprising a combination chart;

determine a tabular representation of the selected data; and cause presentation of the graphical representation and the tabular representation within the graphical user interface.

* * * * *